United States Patent
Lang et al.

(10) Patent No.: US 6,191,164 B1
(45) Date of Patent: Feb. 20, 2001

(54) SULFONAMIDE-SUBSTITUTED CHROMANS, PROCESSES FOR THEIR PREPARATION, THEIR USE AS A MEDICAMENT OR DIAGNOSTIC, AND MEDICAMENT COMPRISING THEM

(75) Inventors: Hans Jochen Lang, Hofheim; Uwe Gerlach, Hattersheim; Joachim Brendel, Bad Vilbel; Henrich Christian Englert, Hofheim; Heinz Gögelein, Frankfurt; Max Hropot, Flörsheim; Helmut Bohn, Schöneck; Andreas Herling, Bad Camberg; Andreas Busch, Kelkheim; Rainer Greger, Heitersheim, all of (DE)

(73) Assignee: Hoechst Aktiengesellschaft, Frankfurt am Main (DE)

( * ) Notice: Under 35 U.S.C. 154(b), the term of this patent shall be extended for 0 days.

(21) Appl. No.: 09/258,289

(22) Filed: Feb. 26, 1999

Related U.S. Application Data

(63) Continuation of application No. 09/086,466, filed on May 28, 1998, which is a continuation-in-part of application No. 08/855,414, filed on May 13, 1997, now abandoned.

(30) Foreign Application Priority Data

May 15, 1996 (DE) ................................. 196 19 614
Sep. 26, 1996 (DE) ................................. 196 39 462

(51) Int. Cl.[7] .................... A01N 43/16; C07D 311/74; C07D 34/76

(52) U.S. Cl. ............................ 514/456; 549/404

(58) Field of Search ............................. 549/404; 514/456

(56) References Cited

U.S. PATENT DOCUMENTS

| | | | |
|---|---|---|---|
| 4,882,353 | 11/1989 | Niewöhner et al. | 514/456 |
| 5,082,858 | 1/1992 | Garcia et al. | 514/456 |

FOREIGN PATENT DOCUMENTS 0 389 861 B2   10/1990   (EP) .

OTHER PUBLICATIONS

Wargh et al Chemical Abstract vol. 125 No. 191888 "The cAMP–regulated and 293B inhibited K+ conductance of rat colonic crypt base cells" (1996).*

G. Edwards et al., TIPS vol. 11, pp. 417–422 (1990).

Lohrmann, E. et al., "A new class of inhibitors of cAMP–medicated Cl⁻secretion in rabbit colon, acting by the reduction of cAMP–activated K⁺conductance," *Pflügers Archiv–European Journal of Physiology*, vol. 429, p. 517–530 (1995).

Busch, Andreas et al., "The Novel Class III Antiarrhythmics NE–10064 and NE–10133 Inhibit $I_{SK}$ Channels Expressed in *Xenopus oocytes* and $I_{KS}$ in Guinea Pig Cardiac Myocytes," *Biochemical and Biophysical Research Comnuncations*, vol. 202, No. 1, (Jul. 15, 1994).

Busch, A. E. et al., "Inhibition of $I_{Ks}$ in guinea pig cardiac myocytes and guinea pig $I_{sK}$ channels by the chromanol 293B," *Pflügers Arch—Eur. J. Physiol.*, vol. 432, pp. 1094–1096 (1996).

(List continued on next page.)

Primary Examiner—John Kight
Assistant Examiner—Raymond Covington
(74) Attorney, Agent, or Firm—Finnegan, Henderson, Farabow, Garrett & Dunner, L.L.P.

(57) ABSTRACT

Sulfonamide-substituted chromans, processes for their preparation, their use as a medicament or a diagnostic, and medicament comprising them Chromans of the formula I

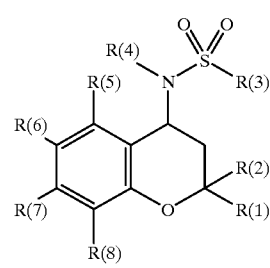

and of the formula 1a

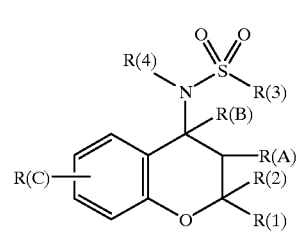

having the meanings R(A), R(B), R(C) and R(1) to R(8) indicated in the claims are outstandingly suitable for preparing a medicament for blocking the K⁺ channel which is opened by cyclic adenosine monophosphate (cAMP); and further for preparing a medicament for inhibiting gastric acid secretion; for the treatment of ulcers of the stomach and of the intestinal region, in particular of the duodenum, for the treatment of reflux esophagitis, for the treatment of diarrheal illnesses, for the treatment and prevention of all types of arrhythmias including ventricular and supraventricular arrhythmias, and for the control of reentry arrhythmias and for the prevention of sudden heart death as a result of ventricular fibrillation.

38 Claims, No Drawings

OTHER PUBLICATIONS

Colatsky, Thomas J. et al., "Channel Specificity in Antiarrhythmic Drug Action," *Circulation*, vol. 82, No. 6, pp. 2235–2242 (Dec. 1990).

Colatsky, Thomas J. et al., "Potassium Channel Blockers as Antiarrhythmic Drugs," *Drug Development Research*, vol. 33, pp. 235–249 (1994).

Lynch, Joseph J. et al., "Cardiac Electrophysiologic and Antiarrhythmic Actions of Two Long–Acting Spirobenzopyran Piperidine Class III Agents, L–702,958 and L–706,000 [MK–499]," *The Journal of Pharmacology and Experimental Therapeutics*, vol. 269, No. 2, pp. 541–554 (May 1994).

Soll, R. M. et al., "N–Sulfonamides of Benzopyran–Related Potassium Channel Openers: Conversion of Glyburide Insensitive Smooth Muscle Relaxants to Potent Smooth Muscle Contractors," *Bioorganic & Medicinal Chemistry Letters*, vol. 4, No. 5, pp. 769–773 (Mar. 10, 1994).

Spector, Peter S. et al., "Class III Antiarrhythmic Drugs Block HERG, a Human Cardiac Delayed Rectifier $K^+$ Channel," *Circulation Research*, vol. 78, No. 3, pp. 499–503 (Mar. 1996).

Süssbrich, H. et al., "Putative Physiological Role of $I_{sK}$ Channels in cAMP–mediated $Cl^-$ Secretion of Epithelial Cells," *Pflügers Archiv–European Journal of Physiology*, Supplement to vol. 431, No. 6, p. R22 (Mar. 24–27, 1996).

Süssbrich, H. et al., "Blockade of $I_{sK}$ Channels by Cromanols—Putative Role of $I_{sK}$ in cAMP–mediated $Cl^-$ Secretion of Epithelial Cells," *Archiv of Pharmacology*, Supplement to vol. 353, No. 4, p. R72 (Mar. 12–14, 1996).

* cited by examiner

SULFONAMIDE-SUBSTITUTED CHROMANS, PROCESSES FOR THEIR PREPARATION, THEIR USE AS A MEDICAMENT OR DIAGNOSTIC, AND MEDICAMENT COMPRISING THEM

This is a continuation of application Ser. No. 09/086,466, filed May 28, 1998, which is a continuation-in-part of application Ser. No. 08/855,414 filed May 13, 1997, now abandoned.

SUMMARY OF THE INVENTION

The invention relates to chromans of the formula I

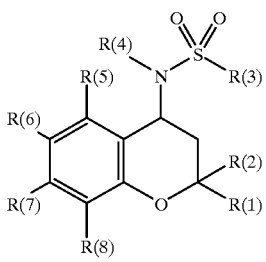

in which:
R(1) and R(2) independently of one another are hydrogen, $C_2F_{2p-1}$, alkyl having 1,2,3,4,5 or 6 carbon atoms or phenyl,
which is unsubstituted or substituted by 1 or 2 substituents selected from the group consisting of F, Cl, Br, I, $CF_3$, methyl, methoxy, sulfamoyl, methylsulfonylamino and methylsulfonyl;
p is 1,2 or 3;
or
R(1) and R(2) together are an alkylene chain having 2,3,4,5,6,7,8,9 or 10 carbon atoms;
R(3) is $R(9)$—$C_nH_{2n}[NR(11)]_m$—:
R(9) is hydrogen or cycloalkyl having 3,4,5,6,7 or 8 carbon atoms;
n is zero, 1, 2, 3, 4, 5, 6, 7, 8, 9 or 10;
m is zero or 1;
R(11) is hydrogen or alkyl having 1, 2, 3, 4, 5 or 6 carbon atoms; or
R(11), together with R(9), is an alkylene group having from 1,2,3,4,5,6,7 or 8 carbon atoms:
where one $CH_2$ group of the group $C_nH_{2n}$ can be replaced by —O—, —$SO_q$— or —NR(10)—;
q is zero, 1 or 2;
R(10) is hydrogen, methyl or ethyl;
R(4) is $R(12)$—$C_rH_{2r}$—;
R(12) is hydrogen, cycloalkyl having 3, 4, 5, 6, 7 or 8 carbon atoms, piperidyl, 1-pyrrolidinyl, N-morpholine, N-methylpiperazino, $C_pF_{2p+1}$, pyridyl, thienyl, imidazolyl or phenyl,
which is unsubstituted or substituted by 1 or 2 substituents selected from the group consisting of F, Cl, Br, I, $CF_3$, methyl, methoxy, sulfamoyl, methylsulfonyl and methylsulfonylamino;
r is 1, 2, 3, 4, 5, 6, 7, 8, 9, 10, 11, 12, 13, 14, 15, 16, 17, 18, 19 or 20;
where one $CH_2$ group of the group $C_rH_{2r}$ can be replaced by —O—, —C=C—, —C≡C—, —CO—, —CO—O—, —$SO_q$— or —NR(10)—;
q is zero, 1 or 2;
R(10) is hydrogen, methyl or ethyl;

R(5), R(6), R(7) and R(8) independently of one another are hydrogen, F, Cl, Br, I, alkyl having 1, 2, 3 or 4 carbon atoms, cycloalkyl having 3, 4, 5, 6, 7 or 8 carbon atoms, —CN, —$CF_3$, —$C_2F_5$, —$C_3F_7$, —$N_3$, —$NO_2$, —$NO_2$, —CONR(13)R(14), —COOR(15), $R(16)$—$C_sH_{2s}$—Y— or phenyl,
which is unsubstituted or substituted by 1 or 2 substituents selected from the group consisting of F, Cl, Br, I, $CF_3$, methyl, methoxy, sulfamoyl and methylsulfonyl;
R(13) and R(14) independently of one another are hydrogen or alkyl having 1, 2 or 3 carbon atoms;
R(15) is hydrogen, methyl, ethyl, phenyl or —$C_uH_{2u}$—NR(13)R(14);
u is 2 or 3;
R(16) is hydrogen, cycloalkyl having 3, 4, 5, 6, 7 or 8 carbon atoms, —COOR(15), thienyl, imidazolyl, pyridyl, quinolyl, isoquinolyl, piperidyl, 1-pyrrolidinyl, N-morpholino, N-methylpiperazino, $C_tF_{2t+1}$ or phenyl,
which is unsubstituted or substituted by 1 or 2 substituents selected from the group consisting of F, Cl, Br, I, $CF_3$, methyl, methoxy, sulfamoyl or methylsulfonyl;
s is zero, 1, 2, 3, 4, 5 or 6;
t is 1, 2 or 3;
Y is $SO_q$, —CO—, —$SO_2$—NR(10)—, —O—, —NR(10)— or —$CO_{13}$NR(10);
but where R(6) cannot be —$OCF_3$ or —$OC_2F_5$;
and their physiologically tolerable salts.

Preferred compounds of the formula I are those in which:
R(1) and R(2) independently of one another are hydrogen, $C_{F3}$, alkyl having 1, 2 or 3 carbon atoms, jointly an alkylene chain having 4 or 5 carbon atoms or phenyl,
which is unsubstituted or substituted by 1 or 2 substituents selected from the group consisting of F, Cl, Br, I, $CF_3$, methyl, methoxy, sulfamoyl and methylsulfonyl;
R(3) is $R(9)$—$C_nH_{2n}[NR(11)]_m$—;
R(9) is hydrogen;
n is zero, 1, 2, 3, 4, 5 or 6;
m is zero or 1;
R(11) is hydrogen or alkyl having 1, 2, 3 or 4 carbon atoms;
R(4) is $R(121)$—$C_rH_{2r}$;
R(12) is hydrogen, cycloalkyl having 5, 6, 7 or 8 carbon atoms, $CF_3$, pyridyl or phenyl,
which is unsubstituted or substituted by 1 or 2 substituents selected from the group consisting of F, Cl, $CF_3$, sulfamoyl or methylsulfonyl;
r is 1,2,3,4,5,6,7,8,9 or 10;
where one $CH_2$ group of the group $C_rH_{2r}$ can be replaced by —O—, —$CO_{13}$, —CO—O— or —$SO_q$—;
q is zero, 1 or 2;
R(5), R(6), R(7) and R(8) independently of one another are hydrogen, F, Cl, Br, I, alkyl having 1 or 2 carbon atoms, —CN, —$CF_3$, —$NO_2$, —CONR(13)R(14), —COOR(15), $R(16)$—$C_sH_{2s}$—Y— or phenyl,
which is unsubstituted or substituted by a substituent selected from the group consisting of F, Cl and $CF_3$;
R(13) and R(14): independently of one another are hydrogen or alkyl having 1,2 or 3 carbon atoms;
R(15) is methyl, ethyl, phenyl or —$C_uH_{2u}$—NR(13)R(14);
u is 2 or 3;

R(16) is hydrogen, cycloalkyl having 5 or 6 carbon atoms, $C_tF_{2t+1}$ or phenyl, which is unsubstituted or substituted by a substituent selected from the group consisting of F, Cl, Br, $CF_3$, methyl, methoxy, sulfamoyl or methylsulfonyl;

t is 1, 2 or 3;

s is zero, 1, 2, 3 or 4;

Y is $SO_q$, —CO—, —$SO_2$—NR(10)—, —O—, —NR(10)— or —CO—NR(10);

q is zero, 1 or 2;

R(10) is hydrogen or methyl;

but where R(6) cannot be —$OCF_3$ or —$OC_2F_5$;

and their physiologically tolerable salts.

Particularly preferred compounds of the formula I are those in which:

R(1) and R(2) independently of one another are $CF_3$, methyl or phenyl, which is unsubstituted or substituted by 1 or 2 substituents selected from the group consisting of F, Cl, Br, I, $CF_3$, methyl, methoxy, sulfamoyl and methylsulfonyl;

R(3) is alkyl having 1, 2, 3 or 4 carbon atoms, dimethylamino or diethylamino;

R(4) is R(12)—$C_rH_{2r}$;

R(12) is hydrogen, cycloalkyl having 5 or 6 carbon atoms or $CF_3$;

is 1, 2, 3, 4, 5, 6, 7 or 8;

where one $CH_3$ group of the group $C_rH_{2r}$ can be replaced by —O—, —CO—, —CO—O— or —$SO_q$—;

q is zero, 1 or 2;

R(5), R(6), R(7) and R(8) independently of one another are hydrogen, F, Cl, Br, I, alkyl having 1 or 2 carbon atoms, —CN —$NO_2$, —COOR(15), R(16)—$C_sH_{2s}$—Y— or phenyl, which is unsubstituted or substituted by a substituent selected from the group consisting of F or Cl;

R(15) is methyl, ethyl, phenyl or —$C_uH_{2u}$—NR(13)R(14);

u is 2 or 3;

R(13) and R(14) independently of one another are hydrogen or alkyl having 1, 2 or 3 carbon atoms;

R(16) is hydrogen, $CF_3$ or phenyl, s is zero, 1, 2, 3 or 4;

y is $SO_q$, —CO—, —$SO_2$—NR(10)—, —NR(10)— or —CO—NR(10);

q is zero, 1 or 2;

R(10) is hydrogen or methyl;

but where R(6) cannot be —$OCF_3$, and their physiologically tolerable salts.

Very particularly preferred compounds of the formula I are the following:

4-(N-ethylsulfonyl-N-methyl)amino-6-fluoro-2,2-dimethylchroman, 6-cyano-4-(N-ethylsulfonyl-N-methyl)amino-2,2-dimethylchroman, 4-(N-ethylsulfonyl-N-methyl)amino-6-methoxycarbonyl-2,2-dimethyl-chroman, 6-cyano-4-[N-ethylsulfonyl-N-(4,4,4-trifluorobutyl)]amino-2,2-dimethyl-chroman, 4-(N-butyl-N-ethylsulfonyl)amino-6-cyano-2,2-dimethylchroman, 4-(N-ethylsulfonyl-N-methyl)amino-2,2,6-trimethylchroman, 7-chloro-4-(N-ethylsulfonyl-N-methyl)amino-6-flouro-2,2-dimethylchroman, 6,7-dichloro-4-(N-ethylsulfonyl-N-methyl)amino-2,2-dimethylchroman, 4-(N-butyl-N-ethylsulfonyl)amino-6-fluoro-2,2-dimethylchroman, 4-(N-ethylsulfonyl-N-methyl)amino-6-fluoro-2,2-tetramethylenechroman, 4[N-ethylsulfonyl-N-(4,4,4-trifluorobutyl)]amino-6-fluoro-2,2-dimethyl-chroman, 4-(N-ethylsulfonyl-N-hexyl)amino-6-fluoro-2,2-dimethylchroman, 6-ethyl-4-[N-ethylsulfonyl-N-(4,4,4-trifluorobutyl)]amino-2,2-dimethyl-chroman.

DETAILED DESCRIPTION OF THE INVENTION

The disclosures of German Application Nos. 19619614.0 filed May 15, 1996 and 19639462.7 filed Sep. 26, 1996 are hereby incorporated by reference.

If the compounds I contain an acidic or basic group or a basic heterocycle, the corresponding, pharmacologically and toxicologically tolerable salts are also a subject of the invention. Thus the compounds I which carry one or more —COOH groups, for example as alkali metal salts, can preferably be used as sodium or potassium salts. Compounds I which carry a basic, protonatable group or a basic heterocyclic radical can also be used in the form of their organic or inorganic, pharmacologically and toxicologically tolerable acid addition salts, for example as hydrochlorides, methanesulfonates, acetates, lactetes, maleates, fumarates, malates, gluconates etc. If the compounds I contain an acidic and basic group in the same molecule, the invention also includes, beside the salt forms described internal salts, so-called betaines.

If the substituents of the compounds of the formula I or alternatively of the formula Ia contain groups with different stereochemical possibilities, the invention also includes the individual possible stereoisomers. Thus the compounds I and Ia contain a chiral center in position 4 of the chroman system, so the individual pure optical antipodes and any desired mixtures of the optical isomers are part of the invention.

The compounds of the formula I can be prepared by different chemical processes, which are likewise part of the invention.

Thus a compound of t he formula I is obtained by a) reacting a compound of the formula II

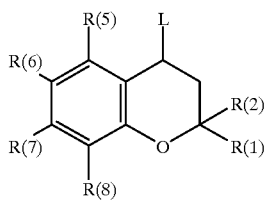

II in which R(1), R(2), R(5), R(6), R(7) and R(8) have the meaning indicated and L is the nucleofugic leaving group customary for an alkylation, in particular Cl, Br, l, $MeSO_2$—O—, a p-toluenesulfonyloxy radical, with a sulfonamide or its salt of the formula III

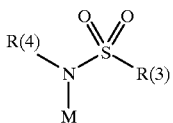

III in a manner known per se, in which R(3) and R(4) have the meaning indicated, but r in the substituent R(4) also has the meaning zero, and M is hydrogen or preferably a metal atom, particularly preferably lithium, sodium or potassium, or by b) reacting a compound of the formula IV

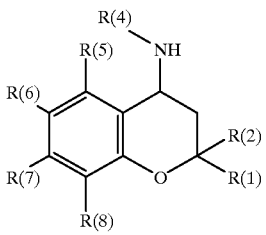

IV in which R(1), R(2), R(4), R(5), R(6), R(7) and R(8) have the meaning indicated, but r in the substituent R(4) also has the meaning zero, with a sulfonic acid derivative of the formula V

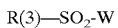

V in which R(3) has the meaning indicated and W is a nucleofugic leaving group, such as fluorine, bromine, 1-imidazolyl, but in particular chlorine;

or by c) reacting a compound of the formula VI

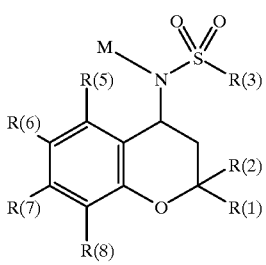

VI in which R(1), R(2), R(5), R(6), R(7), R(8) and M have the meaning indicated, in a manner known per se with an alkylating agent of the formula VII

VII in the sense of an alkylation reaction, in which R(4), with the exception of hydrogen, and L have the meaning indicated;

or by carrying out, d) in a compound of the formula I

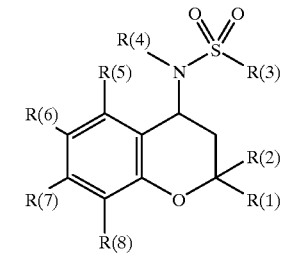

I in which R(1) to R(4) have the meaning indicated, an electrophilic substitution reaction in at least one position R(5) to R(8), if this position is hydrogen and the remaining substituents R(5) to R(8) have the meaning indicated.

Procedure a) describes the alkylation, which is known per se, of a sulfonamide or of one of its salts of the formula III by a chroman derivative of the formula II having alkylating action. As the alkylation of a sulfonamide is carried out from the salt form, when using a free sulfonamide (formula III, M=H) a sulfonamide salt (formula III, m=cation), which is distinguished by higher nucleophilicity and thus by higher reactivity, must be produced by action of a base. If free sulfonamide (M=H) is employed, the deprotonation of the sulfonamide to the salt is carried out in situ with preferred use of those bases which are themselves not alkylated or only slightly alkylated, such as sodium carbonate, potassium carbonate, a sterically strongly hindered amine, e.g. dicyclohexyamine, N,N,N-dicyclohexylethylamine or other strong nitrogen bases of low nucleophilicity, for example DBU, N,N', N'''-trisopropylguanidine etc. However, other bases customarily used for the reaction can also be employed, such as potassium tert-butoxide, sodium methoxide, alkali metal hydrogen carbonates, alkali metal hydroxides, such as, for example, LiOH, NaOH or KOH, or alkali metal hydroxides, for example Ca(OH)$_2$.

In this case, the reaction is preferably carried out in aprotic polar solvents such as dimethylformamide, dimethylacetamide, tetramethylurea, hexamethylphosphoramide, tetrahydrofuran etc. in principle, however, the reaction can also be carried out in polar protic solvents, such as water, menthanol, ethanol, isopropanol, ethylene glycol or its oligomers and their corresponding semithers and ethers. The reaction is carried out in a preferred temperature range from 20°–140° C., particularly preferably from 40° to 100° C. Conveniently, procedure a) can also be carried out under the conditions of a two-phase catalysis. The compounds of the formula II are obtained by methods known from the literature, for example from the corresponding alcohols (formula III, L=—OH) by action of hydrogen halide HL L=Cl, Br, I) or by action of an inorganic acid halide (POCl$_3$, PCl$_3$, PCl$_5$, SOCl$_2$, SOBr$_2$) or by free-radical halogenation of the corresponding chroman derivatives (formula II, L=H) with elemental chlorine or bromine, or with free radical-activatable halogenating agents such as N-bromo-succinimide (NBS) or SO$_2$Cl$_2$ (sulfuryl chloride) in the presence of a free radical chain initiator such as energy-rich light of the visible or ultraviolet wave range or by use of a chemical free-radical initiator such as azobisisobutyronitrile.

Procedure b) describes the reaction, which is known per se and frequently used, of an activated sulfonyl compound of the formula V, in particular of a chlorosulfonyl compound (W=Cl), with an amine of the formula IV to give the corresponding sulfonamide derivative of the formula I, in principle, the reaction can be carried out with a solvent, but reactions of this type are in most cases carried out using a solvent.

The reaction procedure is preferably carried out using a polar solvent, preferably in the presence of a base which itself can be used as a solvent, e.g. when using triethylamine, pyridine and its homologs. Solvents preferably used are, for example, water, aliphatic alcohols, e.g. methanol, ethanol, isopropanol, sec-butanol, ethylene glycol and its monomeric and oligomeric monoalkyl and dialkyl ethers, tetrahydrofuran, dioxane, dialkylated amides such as DMF, DMA, and also TMU and HMPT. The reaction is in this case carried out at a temperature from 0° to 160° C., preferably from 20° to 100° C.

The amines of the formula IV are obtained in a manner known per se from the literature, preferably from the corresponding carbonyl compounds of the formula X

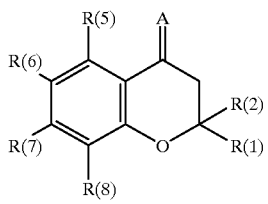

X in which R(1), R(2), R(5), R(6), R(7) and R(8) have the meaning indicated and A is oxygen, either using ammonia or an amine of the formula XI

XI with R(4) having the meaning indicated, but in which r in the substituent R(4) also has the meaning zero, under reductive catalytic conditions, preferably at relatively high temperature in an autoclave. In this case, the Schiff bases of the formula X where A is equal to R(4)—N= are formed primarily by condensation reaction of the ketones X (where A=oxygen) and amines (XI) in situ and immediately converted reductively without isolation thereof into the amine of the formula IV. Correspondingly, the Schiff bases intermediately resulting from X and XI in this reaction (formula X, A: R(4)—N=) can be prepared and isolated in order to convert them subsequently in a separate step with a suitable reductant such as $NaBH_4$, $LiAlH_4$, $NaBH_3CN$ or by catalytic hydrogenation into the compounds of the formula IV. The compounds IV where R(4) is equal to hydrogen can advantageously be obtained in a manner known from the literature by reduction of oximes or oxime ethers (formula X, A is equal to RO—N=), hydrazones (formula X, A: R(18)R(19)N—N=) by use of a complex metal hydride or by catalytic hydrogenation. The necessary oximes and hydrazones are preferably prepared conveniently and in a manner known per se from the ketones of the formula X (A is equal to oxygen) using hydrazine or one of its derivatives or, for example, using hydroxylamine hydrochloride under dehydrating conditions.

Procedure c) describes, like procedure a), the alkylation reaction of a sulfonamide, which is known per se, or of one of its salts VI with an alkylating agent of the formula VII. Corresponding to this reaction analogy, the reaction conditions already described in detail under procedure a) apply for procedure c).

The preparation of the sulfonamide derivatives VI and their precursors have already been described in procedure b).

The preparation of the alkylating agents VII is carried out according to analogous procedures of the literature or as described under procedure a), preferably from the corresponding hydroxyl compounds (formula VII where L is equal to —OH).

Procedure d) describes the further chemical conversion of compounds of the formula I according to the invention into other compounds of the formula I by electrophilic substitution reactions in one or in more of the positions designated by R(5) to R(8), which in each case are hydrogen.

Preferred substitution reactions are 1. aromatic nitration to introduce one or more nitro groups, and their subsequent reduction to $NH_2$—.
2. aromatic halogenation, in particular to introduce chlorine, bromine or iodine,
3. chlorosulfonation to introduce a chlorosulfonyl group by action of chlorosulfonic acid,
4. the Friedel-Crafts acylation reaction to introduce an acyl radical $R(16)$—$C_5H_{2s}$—CO— or a sulfonyl radical $R(16)$—$C_3H_{2s}$—$SO_2$— by action of the corresponding acid chlorides $R(16)$—$C_5H_{2s}$—CO—Cl or $R(16)$—$C_5H_{2s}$—$SO_2$—Cl in the presence of a Lewis acid as a Friedel-Crafts catalyst, preferably or anhydrous aluminum chloride.

The compounds I and Ia are related to the class of 4-acylaminochroman derivatives, in particular of 2,2-dialkyl-4-acylamino-3-chromanols, worked on intensively in pharmaceutical chemistry in the last decade. The most prominent representative of 4-acylaminochromans of this type is chromakalim of the formula XII

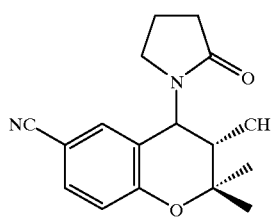

XII and numerous secondary preparations derived from this preparation (e.g. Edwards and Weston, TIPS 11, 417–422 (1990), "Structure Activity Relationships of $K^+$ channel openers".

Chromakalim and other related 4-acylaminochroman derivatives are compounds having a relaxant action on smooth muscular organs, so that they are used for lowering increased blood pressure as a result of vascular muscle relaxation and in the treatment of asthma as a result of the relaxation of the smooth musculature of the airways. It is common to all these preparations that they act at the cellular level, for example, of smooth muscle cells and lead there to an opening of specific ATP-sensitive $K^+$ channels. The increase in negative charge in the cell ("hyperpolarization") induced by the efflux of $K^+$ ions counteracts by means of secondary mechanisms the increase of intracellar $Ca^{2+}$ and thus cell activation, e.g. muscle contraction.

In contrast to these 4-acylaminochroman derivatives which, as mentioned, were identified as openers of the ATP-sensitive $K^+$ channel, the compounds of the formula I and the compounds of the formula Ia according to the invention

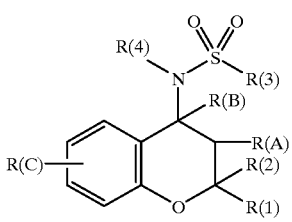

where
- R(A) is hydrogen, OH, —O(CO)alkyl having 1, 2, 3 or 4 carbon atoms or —O—SO$_2$-alkyl having 1, 2, 3 or 4 carbon atoms;
- R(B) is hydrogen;
or
- R(A) and R(B) together are a bond;
- R(1) to R(4) are as indicated above.
- R(C) is CN, acyl having 1, 2, 3, 4, 5 or 6 carbon atoms, F, Cl, Br, I, NO$_2$ or alkyl having 1, 2, 3, 4, 5 or 6 carbon atoms;

with the 4-sulfonylamino structure surprisingly show a strong and specific blocking (closing) action on a K$^+$ channel which is opened by cyclic adenosine monophosphate (cAMP) and differs fundamentally from the K$^+$ (ATP) channel mentioned. More recent investigations on the contrary show that this K$^+$ (cAMP) channel identified in the large intestine appears to be very similar, perhaps even identical, to the I$_{sK}$ channel identified in cardiac muscle. As a result of this blocking of the K$^+$ (cAMP) channel (=I$_{sK}$ channel), the compounds develop in the living body pharamcological actions of high therapeutic utility.

The preparation of compounds of the formula Ia from suitable 3,4-epoxychromans and sulfonamides of the formula III is described in Lohrmann et al., Pflügers Arch.—Eur. J. Physiol. (1995) 429: 517–530.

Thus the compounds I and Ia are distinguished as a novel active compound class of potent inhibitors of stimulated gastric acid secretion. The compounds of the formula I or Ia are thus useful medicaments for the treatment of ulcers of the stomach and of the intentional region, for example of the duodenum. On account of their strong gastric secretion-inhibiting action, they are also suitable as excellent therapeutics for the treatment of reflux esophagitis.

The compounds I and Ia are furthermore distinguished by an antidiarrheal action and are therefore suitable as pharmaceuticals for the treatment of diarrheal illnesses.

The compounds I and Ia can furthermore be used as pharmaceuticals for the treatment and prevention of all types of arrhythmias including atrial, ventricular and superaventricular arhythmias. They can be used in particular for the control of reentry arrhythmias and for the prevention of sudden heart death as a result of ventricular fibrillation.

Meanwhile, publications exist from which a correlation between I$_{sK}$ channel-inhibitory action and the suppression of life-threatening cardiac arrhythmias is described, such as are caused, for example, by β-adren-ergic hyperstimulation (e.g. T. J. Colatsky, C. H. Follmer and C. F. Starmar: "Channel Specificity in Antiarrhythmic Drug Action: Mechanism of potassium channel block and its role in suppressing and aggravating cardiac arrhythmias", Circulation (1990) 82: 2235–2242; A. E. Busch, K. Malloy, W. J. Groh, M. D. Varnum, J. P. Adelman and J. Maylie; "The novel class III antiarrhythmics NE-10064 and NE-10133 inhibit I$_{sK}$ channels in xenopus oocytes and I$_{Ks}$ in guinea pig cardiac myocytes", Biochem. Biophy. Res. Commun. (1994) 202: 265–270).

Beside the above-mentioned chromakalim and acylaminochroman derivatives, in the course of the last years compounds of 4-sulfonyl-aminochroman structure have also been described in the literature, which either differ markedly in structure or in biological action from the compounds of the formula I and the compounds of the formula Ia according to the invention. Thus, European Offenlengungsschrift 315 009 describes chroman derivatives of 4-phenylsulfonylamino structure, which are distinguished by antithrombotic and antiallergic properties.

European Offenlegungsschrift 370 901 describes 3-hydroxychroman derivatives having a 4-phenylsulfonylamino group, in which the remaining valency of the nitrogen atom carries a hydrogen atom. These compounds are thus substituted differently in essential groups of the formula I or Ia. Accordingly, actions on the central nervous system are found for these compounds of European Offenlengungsschrift 370 901, so that they also differ in a pharmacological respect.

European Offenlegungsschrift 389 861 describes 3-hydroxychroman derivatives having a 4-sulfonylamino group. In this case, the benzopyran derivatives described in the EP Offenlengungsschrift are activators or openers of the so-called adenosine triphosphate-sensitive K$^+$ channel [K$^+$ (ATP) channel]. Now, as is known, the pharmacological actions of K$^+$ (ATP) channel openers are completely different from the blockers of the I$_{sK}$ channel described here. Thus for the K$^+$ (ATP) channel openers, typical vasodilating and hypotensive properties were demonstrated for this mechanism. As expected, the described K$^+$ (ATP) channel openers synthesized by the authors show typical, specific antiarrhythmic properties for this mechanism of K$^+$ channel opening. In a basic study, Lucchesi et al. (J. Cardiovasc. Pharmacol. 15, 452–464 [1990)] were impressively able to show that K$^+$ (ATP) channel openers do not have an antiarrhythmic action on the diseased heart which is undersupplied with oxygen or in sudden ischemias, but in contrast even cause life-threatening profibrillatory effects. These dangerous conditions are caused as a consequence of the reductions in the repolarization period resulting from the activation of the K$^+$ (ATP) channel. Unlike these life-threatening profibrillatory effects on the diseased, defectively supplied heart due to the action of K$^+$ (ATP) channel openers, blockers of the K+ (cAMP) channel should show antifibrillatory action under these conditions. As a prominent representative of the compounds of the formula Ia synthesized by us, in the meantime 6-cyano-4-(n-ethylfulsonyl-N-methyl)amino-2,2-dimethyl-3-chromanol found its way into the most recent literature under the name 293B as an example of a highly specific I$_{Ks}$ or I$_{sX}$ channel blocker having a corresponding lengthening of the action potential on the heart (Süβbrich et al., Naunyn Schiedebergs Arch. Pharm. [1996]353 (4, Suppl, R72; Pflügers Arch.-Eur. J. Physiol. 431 (6) [Suppl], R 22 [1996], A. Busch et al., Pflügers Arch.-Eur. J. Physiol. 432 (6) [Suppl], 1094–1096 [1996]).

On the basis of specific structural knowledge, a few compounds were synthesized and investigated by us which admittedly are already disclosed in the Offenlengungsschrift mentioned (EP Offenlengungsschrift 389 861), but were not described, synthesized or recognized in their therapeutic action by the authors. For these specific 3-hydroxy-substituted chromans prepared and investigated by us, a potent blockade of the K$^+$(cAMP) channel (Pflügers Arc.-Eur. J. Physiol. [1995] 429: 517–530 A new class of inhibitors of cAMP-mediated Cl$^+$ secretion in rabbit colon, acting by the reduction of cAMP-activated K$^+$ conductance) has now surprisingly been found and the inhibition of the $I_{Ks}$ channel on the heart. The $I_{sX}$ channel-blocking action of the 3-hydroxy-substituted chromans, however, is markedly less pronounced than that of the corresponding hydroxyl group-free chromans of the formula I.

The invention therefore also relates to the use of compounds of the formula Ia for the treatment of sudden cardiac death, ventricular fibrillations and generally of arrhythmias of the diseased heart which are to be attributed to the $I_{Ks}$ channel.

The publication "N-Sulfonamides of benzopyran-related potassium channel openers: conversion of glyburyde insensitive smooth muscle relaxants to potent smooth muscle contractors" in Bioorg. Med. Chem. Lett. (1994) 4: 769–773 describes specific trifluoromethyl-substituted 4-sulfonyl-aminochroman derivatives which, however, in contrast to the structurally different $K^+$(cAMP) channel blockers described here have biologically different pharmacological actions and thus other therapeutic application areas.

Most recently, spiro[2H-1-benzopyran-2,4'-piperidines] having an essential basic side group have additionally been described in the literature, e.g. MK-499 "Cardiac electrophysiology and antiarrhythmic actions of two long-acting spirobenzopyran piperidine class III agents, L-702,958 and L-706,000 (MK 499)"J. Pharmakol. Exp. Ther. (1994) 269: 541–554; T. J. Colatsky and T. M. Argentieri, "Potassium channel blockers as antiarrhythmic drugs"; Drug Develop. Res. (1994) 33: 235–249.

These "spirobenzopyran piperidine class III agents" are, however, very clearly characterized in the literature with respect to their mode of action [P. S. Spector, M. E. Curran, M. T. Keating, M. C. Sanguinetti, Circulation Res. (1996) 78: 499–503; J. J. Lynch et al., J. Pharmacol Exp. Ther. (1994) 259: 541–554]. IN this case, it is clearly described and shown in the literature cited that the antiarrhythmic action of these compounds is caused by the inhibition of the HERG channel and of the rapidly activating component of the delayed rectifier $K^+$ channel, of the $I_{Kr}$ channel. Thus the spirobenzopyran piperidines are characterized as substances having a proarrhythmic component and having the danger of an increased mortality compared to placebo, as has been shown for this active compound class in the Sword study. This is in clear contrast to the compounds according to the invention, whose advantage consists in the blocking of the slow-activating component of the delayed rectifier $K^+$ channel, of the $I_{Ks}$ channel, which compounds do not have this proarrhythmic component.

The compounds of the formula I or Ia can also be combined with other active compounds to achieve an advantageous therapeutic action. But in the treatment of cardiovascular disorders, advantageous combinations with cardiovascular substances are conceivable. Possible advantageous combination components of this type for cardiovascular disorders can be, for example, other antiarrhythmics, i.e. class I, II or III antiarrhythmics, such as, for example, so-called $I_{Ks}$ channel blockers, e.g. dofetilide, furthermore hypotensive substances such as ACE inhibitors (for example enalapril, captopril, ramipril), angiotensin antagonists, $K^+$ channel activators, and also alpha- and β-receptor blockers, but also sympathomimetic compounds and compound having an adrenergic action, as well as $Na^+/H^+$ exchange inhibitors, calcium channel antagonists, phosphodiesterase inhibitors and other substances having positive inotropic action such as digitalis glycosides and diuretics.

A combination with substances having antibiotic action and with antiulcer agents, for example with $H_2$ antagonists (ranitidine, cimetidine, famotidine etc.) can furthermore be advantageous, such as, in particular, in the application for the treatment of gastrointestinal illnesses.

Pharmaceuticals which contain a compound I or a compound of the formula Ia according to the invention can be administered orally, parenterally, intravenously, rectally or by inhalation, the preferred administration being dependent on the particular clinical picture of the illness. The compounds I and Ia can in this case be used on their own or together with pharmaceutical auxiliaries, namely both in veterinary and in human medicine.

The auxiliaries which are suitable for the desired pharmaceutical formulation are familiar to the person skilled in the art on the basis of his expert knowledge. Beside solvents, gel-forming agents, suppository bases, tableting auxiliaries and other active compound excipients, it is possible to use, for example, antioxidants, dispersants, emulsifiers, antifoams, flavor corrigents, preservatives, solubilizers or colorants.

For a form for oral use, the active compounds I and Ia are mixed with the additives suitable for this purpose, such as excipients, stabilizers or inert diluents, and are brought by means of the customary methods into the suitable administration forms, such as tablets, coated tablets, hard gelatin capsules, aqueous, alcoholic or oily solutions. Inert excipients which can be used are, for example, gum arabic, magnesia, magnesium carbonate, potassium phosphate, lactose, glucose or starch, in particular corn starch. In this case, preparation can be carried out both as dry and as moist granules. Suitable oily excipients or solvents are, for example, vegetable or animal oils, such as sunflower oil or cod-liver oil.

For subcutaneous or intravenous administration, the active compounds of the formula I or of the formula Ia are brought into solution, suspension or emulsion, if desired with the substances customary for this purpose such as solubilizers, emulsifiers or other auxiliaries. Possible solvents are, for example: water, physiological saline solution or alcohols, e.g. ethanol, propanol, glycerol, and in addition also sugar solutions such as glucose or mannitol solutions, or alternatively a mixture of the various solvents mentioned. As solubilizers, for example, oligosaccharides such as cyclodextrins are also used.

Suitable pharmaceutical formulations for administration in the form of aerosols or sprays are, for example, solutions, suspensions or emulsions of the active compound of the formula I or of the formula Ia in a pharmaceutically acceptable solvent, such as, in particular, ethanol or water, or a mixture of such solvents. If required, the formulation can also contain other pharmaceutical auxiliaries such as surfactants, emulsifiers and stabilizers as well as a propellant. Such a preparation customarily contains the active compound in a concentration of approximately 0.1 to 10, in particular of approximately 0.3 to 3% by weight.

The dose or effective amount of the active compound of the formula I or of the formula Ia to be administered to a patient and the frequency of administration to the patient is readily determined by one or ordinary skill in the art, by the use of known techniques and by observing results obtained under analogous circumstances. In determining the effective amount or dose, a number of factors are considered by the attending diagnostician, including but not limited to, the potency and duration of action of the compounds used; the nature and severity of the illness to be treated as well as on the sex, age, weight, general health and individual responsiveness of the patient to be treated, and other relevant circumstances.

The term "Patient" means a mammal such as a dog, cat, guinea pig, mouse, rat or human being.

The terms "Treating" or "to treat" means to alleviate symptoms, eliminate the causation either on a temporary or permanent basis, or to prevent or slow the appearance of symptoms.

On average, the daily dose or effective amount of a compound of the formula I in the case of a patient of weight approximately 75 kg is at least 0.1 mg, preferably 10 mg to at most 100 mg, preferably at most 1 g; or for compounds of the formula Ia at least 1 mg, preferably 50 mg, up to at most 300 mg, preferably 1 g.

Explanation of the abbreviations used in the text

| | |
|---|---|
| DMA | Dimethylacetamide |
| HMPT | Hexamethylphosphoramide |
| TMU | Teetramethylurea |
| hr | Hour(s) |
| mol | Mole |
| mmol | Millimole |
| min | Minutes |
| TEA | Triethylamine |
| THF | Tetrahydrofuran |

EXAMPLES

Example 1

4-(N-Ethylsulfonyl-N-methyl)amino-2,2-dimethylchroman

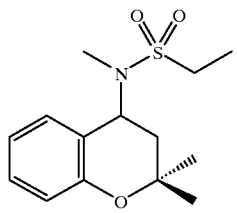

a) 2,2-Dimethyl-4-chromanone oxime

A reaction mixture prepared from 10 mmol of 2,2-dimethyl-4-chromanone, 12 mmol of hydroxylamine hydrochloride in 5 ml of methanol and 5 ml of pyridine is heated with stirring over the course of 2 hours to 80–85° C., the solvent is distilled off on a rotary evaporator and the oily residue is crystallized under water.

Crystalline substance, melting point 115–118° C.

b) 4-Amino-2,2-dimethylchroman hydrochloride

A solution of 10 mmol of 2,2-dimethyl-4-chromanone oxime and 75 ml of methanol is hydrogenated, after addition of Raney nickel as a catalyst, in an autoclave with hydrogen at 60° C., 100 atm. pressure for a period of 6 hours. After filtration and the removal of the solvent by distillation, the amorphous residue is dissolved in ethyl acetate and the solution is treated with diethyl ether saturated with HCl gas until it has a strongly acidic reaction. The crystalline precipitate of 2,2-dimethyl-4-aminochroman hydrochloride is filtered off, washed several times with ethyl acetate and dried.

Colorless crystals, melting point 268° C.

c) 4-N-Ethylsulfonylamino-2,2-dimethylchroman

Variant 1: a solution of 4.5 mmol of ethanesulfonyl chloride in 5 ml of THF is added at 0° C. in portions to a stirred solution prepared from 4.3 mmol of 4-amino-2,2-dimethylchroman hydrochloride, 15 ml of THF and 1.25 ml of TEA. The mixture is stirred for about 2 hours at 0° C. and for 1 hour further at room temperature, the precipitate is filtered and the solvent is distilled off on a rotary evaporator. The residual oil crystallizes under petroleum ether.

Colorless crystals, melting point 106–108° C.

Variant 2: 0.83 g (0.0065 mol) of ethanesulfonyl chloride is added in portions between 0 and 5° C. to a suspension of 1.06 g (0.005 mol) of 4-amino-2,2-dimethylchroman hydrochloride and 2.0 g (0.02 mol) of TEA in 25 ml of DMA and the mixture is stirred at room temperature for 2 days. After removal of the solvent by distillation on a rotary evaporator, the residue is treated with water, whereupon the oil which separates solidifies in crystalline form after a short time.

Melting point 106–109° C.

d) 4-N-Ethylsulfonyl-N-methylamino-2,2-dimethylchroman

A solution of 0.0111 mol of 4-N-ethylsulfonylamino-2,2-dimethylchroman in 15 ml of anhydrous methanol is slowly added to a sodium methoxide solution, prepared from 0.0166 gram atom of sodium in 20 ml of anhydrous methanol. A solution of 0.014 mol of methyl iodide in 5 ml of anhydrous methanol is then added in portions to this mixture and it is heated for 6 hours at 50° C. under a reflux condenser. The solvent is distilled off on a rotary evaporator, and the residue is treated with ethyl acetate and extracted with 2 N NaOH. The organic phase is dried over anhydrous sodium sulfate and 4-N-ethylsulfonyl-N-methylamino-2,2-dimethylchroman is obtained by again removing the solvent by distillation.

Colorless crystalline substance, melting point: 90–92° C.

Example 2

4-(N-Ethyl-N-ethylsulfonyl)amino-2,2-dimethylchroman

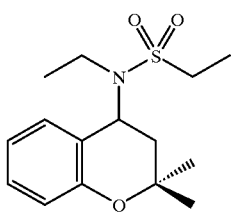

0.0111 mol of 4-N-ethylsulfonylamino-2,2-dimethylchroman is added with stirring in portions to a suspension of 0.0122 mol of sodium hydride in 30 ml of anhydrous dimethylacetamide under an argon atmosphere and the mixture is stirred at room temperature for a further hour. After subsequent addition of 0.0122 mol of ethyl bromide, the mixture is stirred at room temperature for a further 24 hours. The solvent is distilled off under reduced pressure, the residue is then treated with ethyl acetate and extracted with water and the organic phase is distilled off in a rotary evaporator after separation and drying over anhydrous sodium sulfate. 4-(N-Ethyl-N-ethylsulfonylamino-2,2-dimethylchroman is obtained by crystallization under petroleum ether as a colorless crystalline substance, melting point 85° C.

Example 3

4-(N-Benzyl-N-ethylsulfonyl)amino-2,2-dimethylchroman

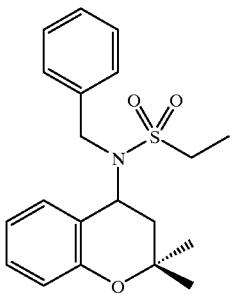

is obtained analogously to the procedure indicated in Example 2 from 4-N-ethylsulfonylamino-2,2-dimethylchroman and benzyl bromide.

Colorless crystals, melting point 59–97° C.

Example 4

4-[N-Ethylsulfonyl-N-(2-dimethylaminoethyl)]amino-2,2-dimethylchroman

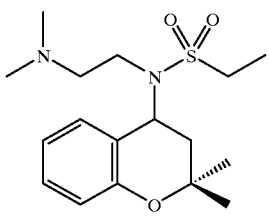

is obtained analogously to the procedure indicated in Example 2 from 4-N-ethylsulfonylamino-2,2-dimethylchroman and 2-chloroethyldimethylamine hydrochloride using double the amount of sodium hydride.

Colorless crystals, melting point 90–93° C.

Example 5

4-N-Ethylsulfonylamino-2,2-dimethyl-6,8-dinitrochroman

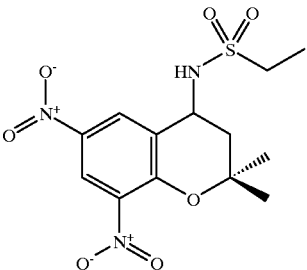

3.71 mmol 4-N-ethylsulfonylamino-2,2-dimethylchroman are added in portions with stirring to 4.3 ml of 100% strength nitric acid cooled to −15 to −20° C. and the mixture is stirred for a further 20 minutes while maintaining the cooling. The reaction mixture is poured into 50 ml of ice water and filtered, and the yellow crystals are washed several times with water. The compound is purified by chromatography on silica gel using a mixture of 3 parts of ethanol and 7 parts of ethyl acetate and subsequently crystallized using petroleum ether.

Yellow crystalline compound, melting point 140–142° C.

Example 6

4-N-Ethylsulfonylamino-2,2-dimethyl-6-nitrochroman

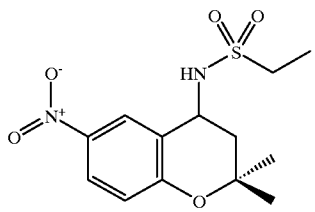

0.54 ml of 100% strength nitric acid is added in portions at −20° C. to a mixture of 3.71 mmol of 4-N-ethylsulfonylamino-2,2-dimethylchroman in 2.54 ml of acetic acid and the mixture is stirred at −20° C. for a further 5 min. The reaction mixture is poured into 50 ml of ice water, and the violet-colored precipitate is filtered and washed several times with cold water on the filter. The crystals are dissolved in a little ethyl acetate and chromatographed on silica gel using a mixture of 3 parts of petroleum ether and 2 parts of ethyl acetate.

Pale yellow crystals, melting point 198–201° C.

Example 7

4-(N-Ethyl-N-ethylsulfonyl)amino-2,2-dimethyl-6-nitrochroman

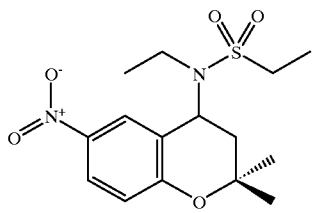

is obtained analogously to the procedure indicated in Example 2 from 4-N-ethylsulfonylamino-2,2-dimethyl-6-nitrochroman and ethyl bromide.

Pale yellow crystals, melting point 180–185° C.

Example 8

4-(N-Ethylsulfonyl-N-methyl)amino-2,2-dimethyl-6-nitrochroman

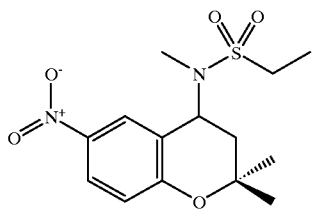

is obtained analogously to the procedure indicated in Example 2 from 4-N-ethylsulfonylamino-2,2-dimethyl-6-nitrochroman and methyl iodide.

Pale yellow crystals, melting point 190–192° C.

Example 9

6-Amino-4-(N-ethylsulfonyl-N-methyl)amino-2,2-dimethylchroman Hydrochloride

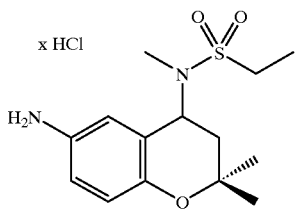

is obtained by catalytic hydrogenation of 7.21 mmol of 4-N-ethylsulfonyl-N-methylamino-2,2-dimethyl-6-nitrochroman with hydrogen gas in 150 ml of methanol using Raney nickel as a catalyst until the theoretical amount of hydrogen has been absorbed over a period of approximately 1.5 hr at 760 torr. After filtration and evaporation of the solvent, the amorphous residue is dissolved in ethyl acetate and the product is purified, by addition of a saturated solution of HCl gas in diethyl ether, by precipitation of the hydrochloride.

Colorless crystals, melting point 75–78° C.

Example 10

6-Amino-4-(N-ethyl-N-ethylsulfonyl)amino-2,2-dimethyl-chroman Hydrochloride

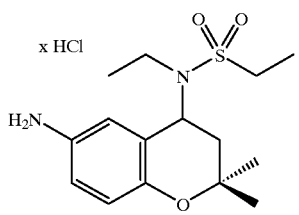

is obtained analogously to the procedure indicated in Example 9 from 4-N-ethyl-N-ethylsulfonylamino-2,2-dimethyl-6-nitrochroman by catalytic hydrogenation with Raney nickel.

Colorless crystals, melting point 95–100° C.

Example 11

4-N-(Dimethylaminosulfonyl)amino-2,2-dimethylchroman

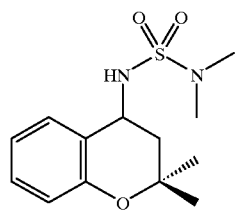

A solution of 0.03 mmol of TEA in 30 ml of DMA is added to a suspension of 10 mmol of 4-amino-2,2-dimethylchroman hydrochloride in 75 ml of anhydrous THF. The mixture is stirred at room temperature for approximately 30 min and a solution of 12 mmol of N,N-dimethylsulfamoyl chloride in 10 ml of anhydrous THF is added dropwise to the suspension with cooling at approximately 10° C. After removing the cooling bath, the mixture is stirred at room temperature for a further 24 hr. The solvent is then distilled off on a rotary evaporator and the residue is stirred under water, crystallization taking place after some time. After filtering off the crystals and washing with water, 4-N-(dimethylaminosulfonyl)amino-2,2-dimethylchroman is obtained as colorless crystals, melting point 77–79° C.

Example 12

4-N-Methyl-N-(dimethylaminosulfonyl)amino-2,2-dimethyl-chroman

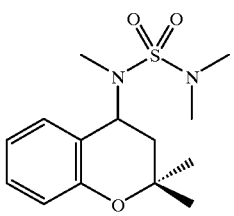

is obtained analogously to the procedure indicated in Example 2 from 4-N-(dimethylaminosulfonyl)amino-2,2-dimethylchroman and methyl iodide.

Colorless crystals, melting point 146–148° C.

Example 13

4-N-Ethylsulfonylamino-6-fluoro-2,2-dimethylchroman

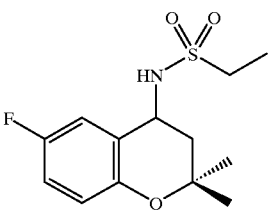

a) 4-Fluorophenyl acetate is obtained as an oily residue by boiling 4-fluorophenol in acetic anhydride and then evaporating the solvent.

b) 5-Fluoro-2-hydroxyacetophenone is obtained from 0.03676 mol of 4-fluorophenyl acetate and 0.083 mol of anhydrous $AlCl_3$ (for Friedel-Crafts reactions) at 120° C. for 2 to 3 hours and by then decomposing with ice water after cooling. The mixture is extracted with ethyl acetate and, after drying over sodium sulfate, the solvent is removed by distillation and the amorphous viscous residue is crystallized under cyclohexane.

Colorless crystalline substance, melting point 46–47° C.

c) 6-Fluoro-2,2-dimethyl-4-chromanone is obtained analogously to the procedure indicated in Example 18 b) from 5-fluoro-2-hydroxyacetophenone and acetone in the presence of pyrrolidine.

Colorless to slightly yellow amorphous residue.

d) 6-Fluoro-2,2-dimethyl-4-chromanone oxime is obtained analogously to the procedure indicated in Example 1 a) from 6-fluoro-2,2-dimethyl-4-chromanone and hydroxylamine hydrochloride, by crystallization of the product under water and recrystallization from cyclohexane using activated carbon.

Colorless crystals, melting point 108–110° C.

e) 4-Amino-6-fluoro-2,2-dimethyl-4-chroman hydrochloride is obtained analogously to the procedure indicated in Example 1 b) by catalytic hydrogenation in an autoclave from 6-fluoro-2,2-dimethyl-4-chromanone oxime, Raney nickel and hydrogen.

Colorless crystals, melting point 226° C., sublimation from 296° C.

f) 4-N-Ethylsulfonylamino-6-fluoro-2,2-dimethylchroman 5.5 mmol of ethanesulfonyl chloride are added to a suspension of 5 mmol of 4-amino-6-fluoro-2,2-dimethyl-4-chroman hydrochloride in 20 ml of DMA and 15 mmol of TEA with stirring and cooling to 10° C. The mixture is stirred for a further 24 hours at room temperature, then the solvent is distilled off on a rotary evaporator and the residue is stirred under 75 ml of water. The oil which separates is extracted with ethyl acetate, and the organic phase is separated off and dried over anhydrous sodium sulfate. After distilling off the solvent in a rotary evaporator, 4-ethylsulfonylamino-6-fluoro-2,2-dimethylchroman is obtained as an amorphous product.

Example 14

4-(N-Ethylsulfonyl-N-methyl)amino-6-fluoro-2,2-dimethyl-chroman

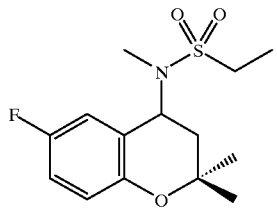

is obtained analogously to the procedure indicated in Example 2 from 4-N-ethylsulfonylamino-6-fluoro-2,2-dimethylchroman and methyl iodide.

Amorphous oily product.

Example 15

6-Fluoro-4-N-(dimethylaminosulfonyl)amino-2,2-dimethyl-chroman

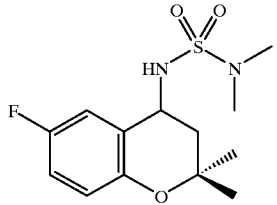

is obtained analogously to the procedure indicated in Example 11 from 4-amino-6-fluoro-2,2-dimethylchroman and N,N-dimethylsulfamoyl chloride in anhydrous DMA.

Colorless crystals, melting point 86–88° C.

Example 16

6-Fluoro-4-[N-methyl-N-(dimethylaminosulfonyl)]amino-2,2-dimethylchroman

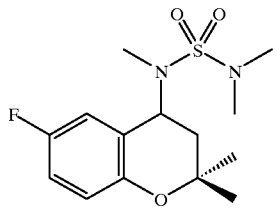

is obtained analogously to the procedure indicated in Example 2 from 6-fluoro-4-N-(dimethylaminosulfonyl)amino-2,2-dimethylchroman and methyl iodide.

Amorphous oily product.

Example 17

6-Cyano-4-(N-ethylsulfonyl-N-methyl)amino-2,2-dimethyl-chroman

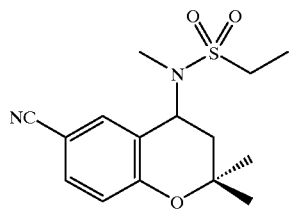

a) 6-Cyano-2,2-dimethylchroman

A suspension consisting of 10 mmol of 6-cyano-2,2-dimethyl-3,4-chromene, 50 ml of methanol and about 500 mg of palladium catalyst on barium sulfate(10% strength) is shaken in a shaking duck under a hydrogen atmosphere at 1 atm and at 20° C. until the theoretical amount of hydrogen has been absorbed. After filtration of the catalyst, the solvent is distilled off on a rotary evaporator and 6-cyano-2,2-dimethylchroman is obtained as a colorless to slightly yellowish oil.

b) 4-Bromo-6-cyano-2,2-dimethylchroman 11 mmol of N-bromosuccinimide and 0.22 g of azobisisobutyronitrile (Aldrich) are added to a solution of 10 mmol of 6-cyano-2,2-dimethyl-chroman in 30 ml of carbon tetrachloride and the suspension thus obtained is heated to boiling under a reflux condenser for 3 hours. Insoluble succinimide is then filtered off, the solvent is distilled off and the residue is crystallized under a mixture of n-hexane and diisopropyl ether.

Slightly yellow crystals, melting point 93–94° C.

c) 6-Cyano-4-[N-ethylsulfonyl-N-methyl]amino-2,2-dimethylchroman

A solution of 11 mmol of ethanesulfonic acid N-methylamide is added dropwise under a protective gas atmosphere of argon to a suspension of 11 mmol of sodium hydride (as an 80% strength oil suspension) in 5 ml of anhydrous DMA and the mixture is stirred for about one hour at room temperature. It is then treated with a solution of 10 mmol of 4-bromo-6-cyano-2,2-dimethylchroman in 7 ml of anhydrous DMA and stirred for 72 hours at 70° C. The reaction mixture is poured with stirring into 75 ml of water, the oily amorphous precipitate is extracted with ethyl acetate and the organic phase is dried over anhydrous sodium sulfate. The solvent is distilled off on a rotary evaporator and the amorphous residue is separated by column chromatography on the silica gel column using a solvent mixture consisting of 1 part of toluene and 1 part of ethyl acetate as eluent. After distilling off the elution liquid in the rotary evaporator, the 6-cyano-4-[N-ethylsulfonyl-N-methyl]amino-2,2-dimethylchroman is obtained as a colorless crystalline product.

Melting point 166–168° C.

Example 18

4-N-Ethylsulfonylamino-6-methoxycarbonyl-2,2-dimethyl-chroman

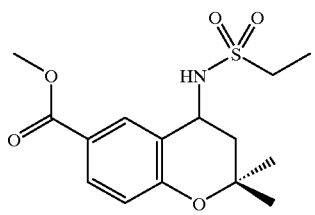

a) 3-Acetyl-4-hydroxybenzoic Acid 36.6 g (0.274 mol) of $AlCl_3$ are suspended in 50 ml of 1,2,4-trichloro-benzene and treated with 9 g (50 mmol) of 4-acetoxybenzoic acid. After dropwise addition of 7.84 g (0.1 mol) of acetyl chloride, the reaction mixture is heated to 130–140° C., the evolution of HCl gas occurring from approximately 60° C. The mixture is stirred for approximately 1 hour at 130° C. and then allowed to cool to 60–70° C., and the mixture is poured cautiously into stirred ice water. It is extracted several times with ethyl acetate, then the combined organic phases are extracted with saturated aqueous sodium bicarbonate solution and the combined aqueous phases are adjusted carefully to pH<1 using concentrated HCl, the 3-acetyl-4-hydroxybenzoic acid separating as sparingly soluble material.

Colorless crystalline substance, melting point 228–233° C.

b) 6-Carboxy-2,2-dimethyl-4-chromanone 13.8 g of pyrrolidine and 40 ml of acetone are added to a suspension of 14.7 g (0.0815 mol) of 3-acetyl-4-hydroxybenzoic acid in 200 ml of acetonitrile. The slowly discoloring solution is allowed to stand at room temperature for 2 days, the solvent is distilled off on a rotary evaporator, the residue is treated with water and adjusted to acidic pH<1 using conc. hydrochloric acid and the crystalline substance is filtered off.

Colorless crystals, melting point 154–150° C.

c) 6-Carboxy-2,2-dimethyl-4-chromanone Oxime 14.9 g of 6-carboxy-2,2-dimethyl-3-chromanone are dissolved in 100 ml of ethanol and 100 ml of pyridine, and after addition of 5.16 g of hydroxylamine hydrochloride the mixture is heated at 80° C. with stirring for 6 hours. The solvent is distilled off on a rotary evaporator. The residue is treated with water and adjusted to pH<1 using conc. hydrochloric acid, and the colorless crystals are filtered off.

Melting point 223–225° C.

d) 4-Amino-6-carboxy-2,2-dimethylchroman 35.2 g (0.15 mol) of 6-carboxy-2,2-dimethyl-4-chromanone oxime are dissolved in 300 ml of methanol by addition of 600 ml of concentrated aqueous ammonia and, after addition of a few grams of Raney nickel catalyst, hydrogenated at 80° C. for 10 hours under 100 atm hydrogen pressure. After filtering off the catalyst, approximately ¾ of the solvent is distilled off in a rotary evaporator. The crystalline precipitate of 4-amino-6-carboxy-2,2-dimethylchroman is filtered off.

Colorless crystals, melting point 307–310° C.

e) 4-Amino-6-methoxycarbonyl-2,2-dimethylchroman 0.05 mol of 4-amino-6-carboxy-2,2-dimethylchroman is treated with 9.5 ml of conc. sulfuric acid in 200 ml of methanol and the dark solution is heated to reflux for 6 hours. The reaction mixture is adjusted to pH 9 with ice cooling by addition in portions of saturated aqueous potassium carbonate solution and the precipitated salt is filtered off. The solvent is distilled off on a rotary evaporator, the oily residue is treated with water and the mixture is extracted several times with diethyl ether. After removing the solvent by distillation, the oily amorphous residue is crystallized under n-heptane.

Colorless crystalline substance, melting point 62–65° C.

f) 4-N-Ethylsulfonylamino-6-methoxycarbonyl-2,2-dimethylchroman is obtained analogously to the procedure indicated in Example 1 c) from 0.0184 mol of 4-amino-6-methoxycarbonyl-2,2-dimethylchroman with 0.021 mol of ethanesulfonyl chloride in THF using excess TEA.

Colorless crystals, melting point 111–113° C.

Example 19

4-(N-Ethylsulfonyl-N-methyl)amino-6-methoxycarbonyl-2,2-dimethylchroman

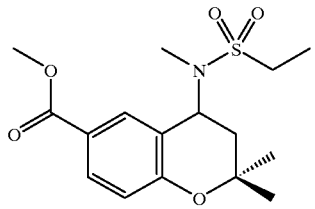

is obtained analogously to the procedure indicated in Example 2 from 0.0155 mol of 4-N-ethylsulfonylamino-6-methoxycarbonyl-2,2-dimethyl-chroman, 0.0232 mol of NaH (as an 80% strength suspension in oil) and 0.0217 mol of methyl iodide in anhydrous DMA.

Colorless crystalline substance, melting point 184–187° C.

Example 20

6-Methoxycarbonyl-4-N-(dimethylaminosulfonyl)amino-2,2-dimethylchroman

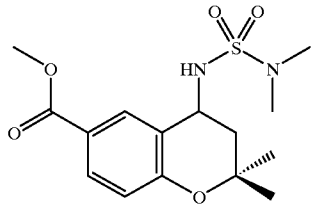

is obtained analogously to the procedure indicated in Example 11 from 4-amino-6-carboxy-2,2-dimethylchroman, dimethylamidosulfonyl chloride and triethylamine in THF.

Colorless crystals, melting point 127–129° C.

Example 21

6-Methoxycarbonyl-4-[N-methyl-N-(dimethylaminosulfonyl)]-amino-2,2-dimethylchroman

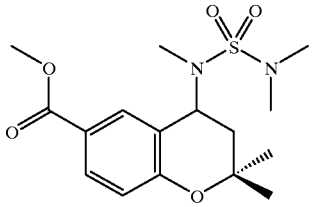

is obtained analogously to the procedure indicated in Example 2 from 6-methoxycarbonyl-4-N-(dimethylaminosulfonyl)amino-2,2-dimethylchroman, NaH and methyl iodide in DMA.

Colorless crystalline substance, melting point 125–129° C.

Example 22

4-(N-Butyl-N-ethylsulfonyl)amino-6-methoxycarbonyl-2,2-dimethylchroman

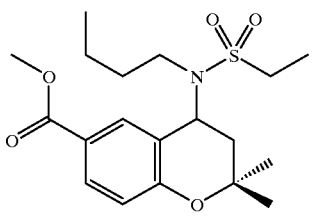

obtained analogously to the procedure indicated in Example 2 from 4-N-ethylsulfonylamino-6-methoxycarbonyl-2,2-dimethylchroman, NaH and 1-butyl iodide in DMA.

Colorless to slightly yellow oily amorphous product.

Example 23

6-Carboxy-4-(N-ethylsulfonyl-N-methyl)amino-2,2-dimethylchroman

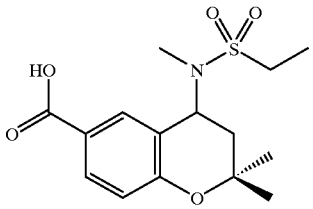

A suspension consisting of 1 g (0.00305 mol) of 4-N-ethylsulfonyl-N-methylamino-6-methoxycarbonyl-2,2-dimethylchroman, 30 ml of methanol and a solution of 0.36 g (0.0091 mol) of NaOH in 20 ml of water is stirred under reflux conditions for approximately 10 hours until the formation of a solution. The solvent is distilled off on a rotary evaporator, the residue is treated with water, the mixture is adjusted to pH 0 to 1 using HCl and the colorless crystals are filtered off.

Melting point 235–237° C.

Example 24

6-Aminocarbonyl-4-(N-ethylsulfonyl-N-methyl)amino-2,2-dimethylchroman

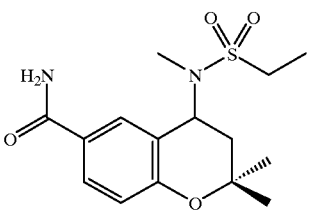

0.38 g (0.0023 mol) of carbonyldiimidazole is added to a solution of 0.7 g of 6-carboxy-4-(N-ethylsulfonyl-N-methyl)amino-2,2-dimethylchroman (0.0021 mol) in 25 ml of anhydrous THF, and the mixture is stirred for 3 hours at room temperature and then treated with 10 ml of conc. aqueous ammonia solution (25% strength). After stirring at room temperature for about 15 hours, the solvent is largely distilled off on a rotary evaporator, the residue is treated with water and the white crystalline substance is filtered off.

Melting point 202–204° C.

Example 25

6-Cyano-4-(N-ethylsulfonyl-N-methyl)amino-2,2-dimethyl-chroman

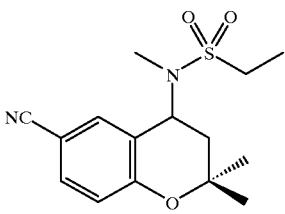

0.5 g (0.0015 mol) of 6-aminocarbonyl-4-(N-ethylsulfonyl-N-methyl)amino-2,2-dimethylchroman is treated, as a mixture with 0.72 g (0.0045 mol) of N-trimethylsilylpyrrolidone, with 0.0013 g (0.000075 mol) of sodium bis(trimethylsilyl)amide under an argon atmosphere and the mixture is heated to 90° C. (bath temperature). From the initial solid mixture is formed a solution, which is stirred at 90° C. for 4 hours and then allowed to stand overnight at room temperature. After removing the inert gas protection and stirring with water, crystallization of the oil occurs. The crystals are filtered off with suction and purified from still-present starting material by chromatography on silica gel using a mixture of 10 parts of methylene chloride and 1 part of methanol as elution medium.

Melting point 164–167° C.

Example 26

6-Carboxy-4-N-ethylsulfonylamino-2,2-dimethylchroman

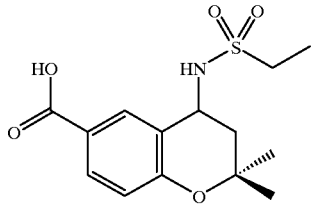

is obtained analogously to the procedure indicated in Example 1 a) from 4-amino-6-methoxycarbonyl-2,2-dimethylchroman with isopropylsulfonyl chloride in THF using excess TEA.

Colorless crystals, melting point 112–115° C.

Example 27

4-[N-Ethylsulfonyl-N-(4,4,4-trifluorobutyl)amino]-6-methoxy-carbonyl-2,2-dimethylchroman

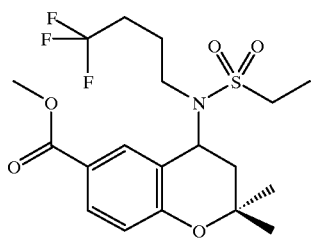

is obtained analogously to the procedure described in Example 2 from 4-N-ethylsulfonylamino-6-methoxycarbonyl-2,2-dimethylchroman and 4,4,4-trifluoro-1-iodobutane in DMA.

Pale yellow to colorless oily amorphous product.

Example 28

6-Carboxy-4-[N-ethylsulfonyl-N-(4,4,4-trifluorobutyl)amino]-2,2-dimethylchroman

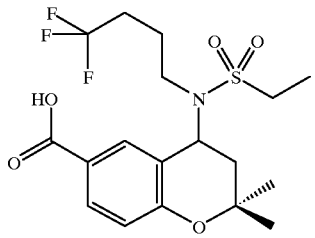

is obtained analogously to the procedure described in Example 23 by alkaline hydrolysis of 4-N-ethylsulfonyl-N-(4,4,4-trifluorobutyl)amino-6-methoxycarbonyl-2,2-dimethylchroman.

Colorless crystalline substance, melting point 189–192° C.

Example 29

4-(N-Butyl-N-ethylsulfonyl)amino-6-methoxycarbonyl-2,2-dimethylchroman

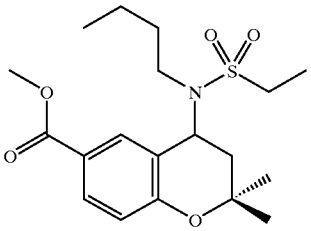

is obtained analogously to the procedure described in Example 2 from 4-N-ethylsulfonylamino-6-methoxycarbonyl-2,2-dimethylchroman and butyl iodide in DMA. Colorless crystalline substance, melting point 81–84° C.

Example 30

6-Methoxycarbonyl-4-N-methylsulfonylamino-2,2-dimethylchroman

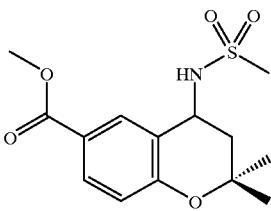

is obtained analogously to the procedure described in Example 1 c) from 4-amino-6-methoxycarbonyl-2,2-dimethylchroman with methanesulfonyl chloride.

Colorless crystalline substance, melting point 159–163° C.

Example 31

6-Aminocarbonyl-4-[N-ethylsulfonyl-N-(4,4,4-trifluorobutyl)-amino]-2,2-dimethylchroman

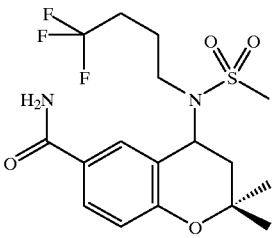

is obtained analogously to the procedure described in Example 24 from 6-carboxy-4 -N-ethylsulfonyl-N-(4,4,4-trifluorobutyl)amino-2,2-dimethyl-chroman, carbonyldiimidazole and ammonia.

Colorless crystalline substance, melting point 170–174° C.

Example 32

6-Carboxy-4-[N-methyl-N-(dimethylaminosulfonyl)amino]-2,2-dimethylchroman

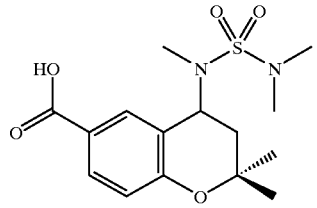

is obtained analogously to the procedure indicated in Example 23 from 6-methoxycarbonyl-4-[N-methyl-N-(dimethylaminosulfonyl)amino]-2,2-dimethylchroman.

Colorless crystalline compound, melting point 245–248° C.

Example 33

6-Cyano-4-[N-ethylsulfonyl-N-(4,4,4-trifluorobutyl)amino]-2,2-dimethylchroman

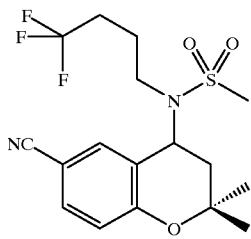

is obtained analogously to the procedure indicated in Example 25 from 6-aminocarbonyl-4-N-ethylsulfonyl-N-(4,4,4-trifluorobutyl)amino-2,2-dimethylchroman and by subsequent purification by column chromatography on silica gel using a mixture of 10 parts of methylene chloride and 1 part of methanol as eluent.

Colorless to pale yellow crystalline substance, melting point 172–176° C.

Example 34

6-Aminocarbonyl-4-[N-methyl-N-(dimethylamino)-sulfonylamino]-2,2-dimethylchroman

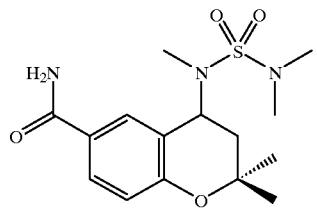

is obtained analogously to the procedure indicated in Example 24 from 6-carboxy-4-[N-methyl-N-(dimethylaminosulfonyl)amino]-2,2-dimethyl-chroman.

Colorless crystalline substance, melting point 215–218° C.

Example 35

6-Cyano-4-[N-methyl-N-(dimethylaminosulfonyl)amino]-2,2-dimethylchroman

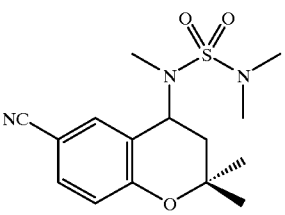

is obtained analogously to the procedure indicated in Example 25 from 6-aminocarbonyl-4-[N-methyl-N-(dimethylaminosulfonylamino]-2,2-dimethylchroman.

Colorless crystalline substance, melting point 100–102° C.

Example 36

4-(N-Butyl-N-ethylsulfonyl)amino-6-carboxy-2,2-dimethylchroman

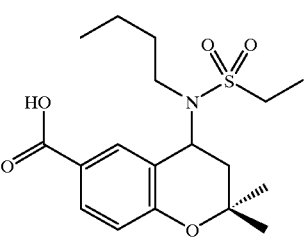

is obtained analogously to the procedure indicated in Example 23 from 4-N-(butyl-N-ethylsulfonyl)amino-6-methoxycarbonyl-2,2-dimethylchroman.

Colorless crystalline compound, melting point 148–151° C.

Example 37

6-Aminocarbonyl-4-(N-butyl-N-ethylsulfonyl)amino-2,2-dimethylchroman

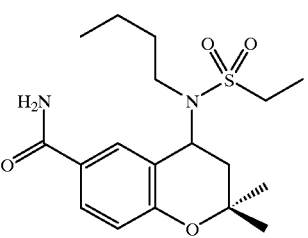

is obtained analogously to the procedure indicated in Example 24 from 4-(N-butyl-N-ethylsulfonyl)amino-6-carboxy-2,2-dimethylchroman.

Colorless crystalline substance, melting point 195–199° C.

Example 38

4-(N-Butyl-N-ethylsulfonyl)amino-6-cyano-2,2-dimethyl-chroman

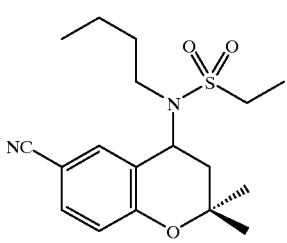

is obtained analogously to the procedure indicated in Example 25 from 6-aminocarbonyl-4-N-butyl-N-ethylsulfonylamino-2,2-dimethylchroman.
Colorless crystalline substance, melting point 96–98° C.

Example 39

4-[N-Ethylsulfonyl-N-(4-picolyl)amino]-6-methoxycarbonyl-2,2-dimethylchroman

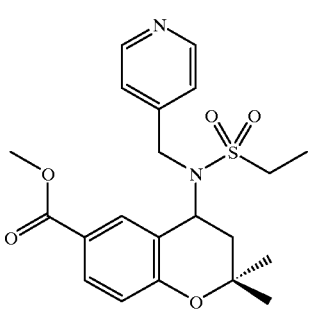

is obtained analogously to the procedure indicated in Example 2 from 0.005 mol of 4-N-ethylsulfonylamino-6-methoxycarbonyl-2,2-dimethylchroman, 0.015 mol of NaH and 0.007 mol of 4-picolyl chloride hydrochloride.
Dark-colored, oily amorphous substance.

Example 40

6-Carboxy-4-[N-ethylsulfonyl-N-(4-picolyl)amino]-2,2-dimethylchroman

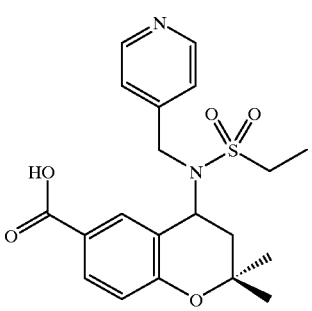

is obtained analogously to the procedure indicated in Example 23 from 4-[N-ethylsulfonyl-N(4-picolyl)amino]-6-methoxycarbonyl-2,2-dimethyl-chroman.
Colorless crystalline substance, melting point 210–212° C.

Example 41

6-Aminocarbonyl-4-[N-ethylsulfonyl-N-(4-picolyl)amino]-2,2-dimethylchroman

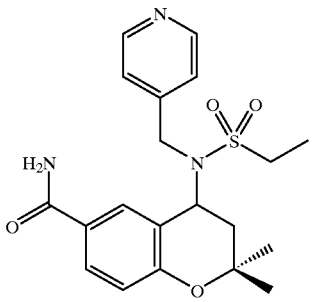

is obtained analogously to the procedure indicated in Example 24 from 6-carboxy-4-N-ethylsulfonyl-N-(4-picolyl)amino-2,2-dimethylchroman.
Colorless crystalline substance, melting point 193–196° C.

Example 42

6-Piperidinocarbonyl-4-N-ethylsulfonyl-N-methylamino-2,2-dimethylchroman

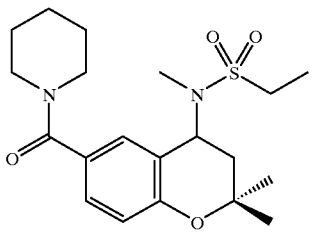

is obtained analogously to the procedure indicated in Example 24 from 0.003 mol of 6-carboxy-4-[N-ethylsulfonyl-N-methylamino]-2,2-dimeth-ylchroman, 0.0033 mol of N,N-carbonyldiimidazole and 0.012 mol of piperdine.
Colorless crystalline substance, melting point 184° C.

Example 43

4-N-Isopropylsulfonylamino-6-methoxycarbonyl-2,2-dimethylchroman

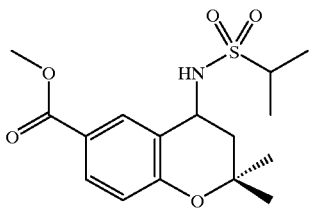

is obtained analogously to the procedure indicated in Example 1c) from 0.024 mol of 4-amino-6-methoxycarbonyl-2,2-dimethylchroman with 0.0319 mol of ethanesulfonyl chloride using excess TEA in THF under reflux conditions in the course of 12 hours and by additional purification of the product by column chromatography on silica gel using a mixture of 1 part of ethyl acetate and 3 parts of toluene as eluent.
Colorless crystals, melting point 111–113° C.

Example 44

4-(N-isopropylsulfonyl-N-methyl)amino-6-methoxycarbonyl-2,2-dimethylchroman

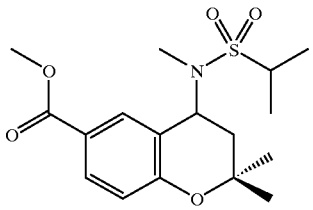

is obtained analogously to the procedure described in Example 2 from 4-N-isopropylsulfonylamino-6-methoxycarbonyl-2,2-dimethylchroman and methyl iodide.

Colorless crystals, melting point 115–119° C.

Example 45

6-Carboxy-4-(N-isopropylsulfonyl-N-methyl)amino-2,2-dimethylchroman

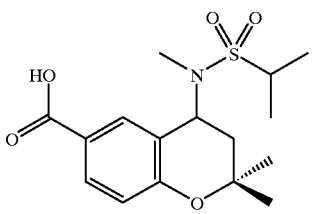

is obtained analogously to the procedure described in Example 23 from 4-(N-isopropylsulfonyl-N-methyl)amino-6-methoxycarbonyl-2,2-dimethylchroman.

Colorless crystals, melting point 228–233° C.

Example 46

6-Aminocarbonyl-4-(N-isoproylsulfonyl-N-methyl)amino-2,2-dimethylchroman

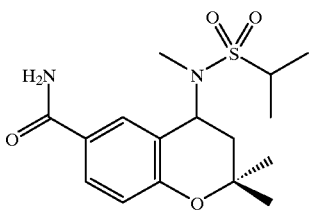

is obtained analogously to the procedure described in Example 24 from 6-carboxy-4-(N-isoproylsulfonyl-N-methyl)amino-2,2-dimethylchroman.

Colorless crystals, melting point 216–220° C.

Example 47

6-Cyano-4-(N-isopropylsulfonyl-N-methyl)amino-2,2-dimethylchroman

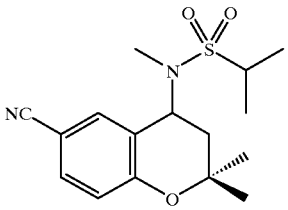

is obtained analogously to the procedure described in Example 25 from 6-aminocarbonyl-4-(N-isopropylsulfonyl-N-methyl)amino-2,2-dimethylchroman. After isolation of the product by filtration, it is purified by chromatography on silica gel using a mixture of 10 parts of methylene chloride and 1 part of methanol and the substance is crystallized under diisopropyl ether after removing the solvent by distillation.

Colorless crystals, melting point 129–135° C.

Example 48

4-N-Butylsulfonylamino-6-methoxycarbonyl-2,2-dimethyl-chroman

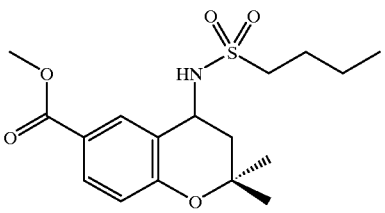

is obtained analogously to the procedure described in Example 1c) from 4-amino-2,2-dimethylchroman hydrochloride and 1-butylsulfonyl chloride.

Melting point 117–120° C.

Example 49

4-(N-Butylsulfonyl-N-methyl)amino-6-methoxycarbonyl-2,2-dimethylchroman

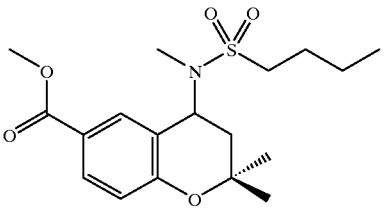

is obtained analogously to the procedure described in Example 2 from 4-N-butylsulfonylamino-6-methoxycarbonyl-2,2-dimethylchroman and methyl iodide.

Colorless to pale yellow amorphous oily product.

Example 50

4-(N-Butylsulfonyl-N-methyl)amino-6-carboxy-2,2-dimethylchroman

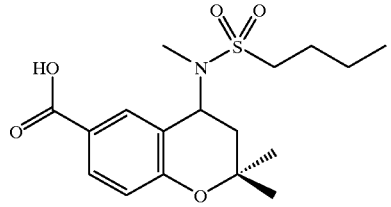

is obtained analogously to the procedure described in Example 23 from 4-(N-butylsulfonyl-N-methyl)amino-6-methoxycarbonyl-2,2-dimethyl-chroman.

Colorless crystalline product, melting point 200–205° C.

Example 51

6-Aminocarbonyl-4-(N-butylsulfonyl-N-methyl)amino-2,2-dimethylchroman

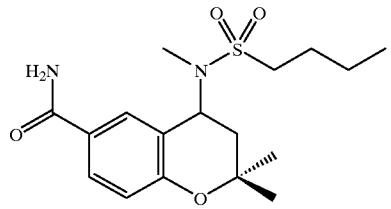

is obtained analogously to the procedure described in Example 24 from 4-(N-butylsulfonyl-N-methyl)amino-6-carboxy-2,2-dimethylchroman.

Colorless crystalline product, melting point 162–165° C.

Example 52

6-Cyano-4-N-butylsulfonyl-N-methylamino-2,2-dimethyl-chroman

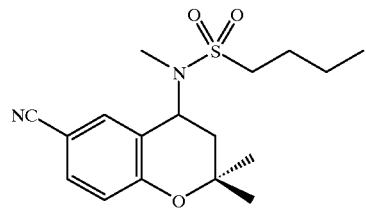

is obtained analogously to the procedure described in Example 25 from 6-aminocarbonyl-4-(N-butylsulfonyl-N-methyl)amino-2,2-dimethylchroman. After isolation of the product by filtration, it is purified by chromatography on silica gel using a mixture of 10 parts of methylene chloride and 1 part of methanol and the substance is crystallized under diisopropyl ether after removing the solvent by distillation.

Colorless crystals, melting point 57–62° C.

Example 53

6-Methyloxycarbonyl-4-(N-methyl-N-methylsulfonyl)amino-2,2-dimethylchroman

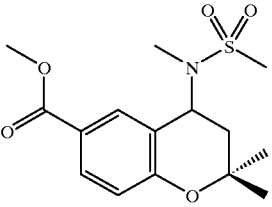

is obtained analogously to the procedure described in Example 2 from 6-methoxycarbonyl-4-N-methylsulfonylamino-2,2-dimethylchroman and methyl iodide.

Colorless crystalline substance, melting point 160–164° C.

Example 54

6-Carboxy-4-(N-methyl-N-methylsulfonyl)amino-2,2-dimethylchroman

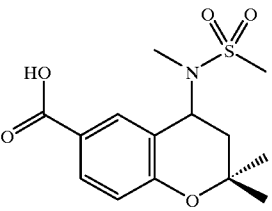

is obtained analogously to the procedure described in Example 23 from 6-methoxycarbonyl-4-N-methyl-N-methylsulfonylamino-2,2-dimethylchroman by alkaline hydrolysis.

Colorless crystalline compound of melting point 214–216° C.

Example 55

6-Aminocarbonyl-4-(N-methyl-N-methylsulfonyl)amino-2,2-dimethylchroman

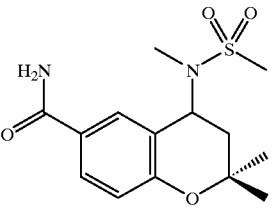

is obtained analogously to the procedure described in Example 24 from 6-carboxy-4-(N-methyl-N-methylsulfonyl)amino-2,2-dimethylchroman.

Colorless crystalline substance, melting point 179–182° C.

Example 56

6-Cyano-4-(N-methyl-N-methylsulfonyl)amino-2,2-dimethylchroman

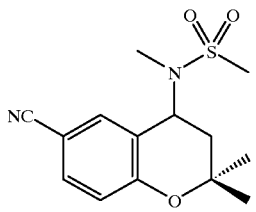

is obtained analogously to the procedure described in Example 25 from 6-aminocarbonyl-4-(N-methyl-N-methylsulfonyl)amino-2,2-dimethyl-chroman. After isolation of the product by filtration, it is purified by chromatography on silica gel using a mixture of 10 parts of methylene chloride and 1 part of methanol and the substance is crystallized under diisopropyl ether after removing the solvent by distillation.

Colorless crystals, melting point 196–200° C.

Example 57

4-(N-Ethylsulfonyl-N-ethyl)amino-6-methoxycarbonyl-2,2-dimethylchroman

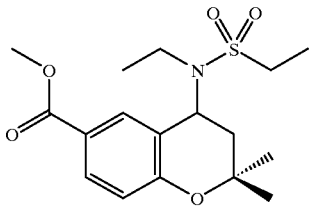

is obtained analogously to the procedure indicated in Example 2 from 0.0091 mol of 4-N-ethylsulfonylamino-6-methoxycarbonyl-2,2-dimethyl-chroman, 0.013 mol of NaH (as an 80% strength suspension in oil) and 0.0125 mol of ethyl iodide in anhydrous DMA.

Colorless crystalline substance, melting point 114–116° C.

Example 58

4-(N-Ethylsulfonyl-N-propyl)amino-6-methoxycarbonyl-2,2-dimethylchroman

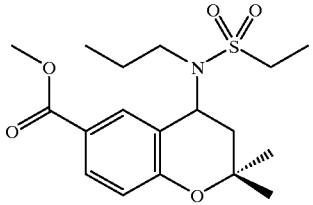

is obtained analogously to the procedure indicated in Example 2 from 0.0091 mol of 4-N-ethylsulfonylamino-6-methoxycarbonyl-2,2-dimethyl-chroman, 0.013 mol of NaH (as an 80% strength suspension in oil) and 0.0126 mol of 1propyl iodide in anhydrous DMA.

Colorless crystalline substance, melting point 106–108° C.

Example 59

4-(N-Ethylsulfonyl-N-cyclopropyl)amino-6-methoxycarbonyl-2,2-dimethylchroman

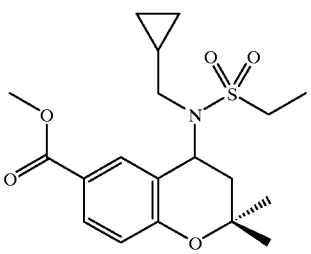

is obtained analogously to the procedure indicated in Example 2 from 0.0091 mol of 4-N-ethylsulfonylamino-6-methoxycarbonyl-2,2-dimethyl-chroman, 0.013 mol of NaH (as an 80% strength suspension in oil) and 0.0126 mol of bromomethylcyclopropane in anhydrous DMA.

Colorless crystalline substance, melting point 108–110° C.

Example 60

4-(N-Ethylsulfonyl-N-1-pentyl)amino-6-methoxycarbonyl-2,2-dimethylchroman

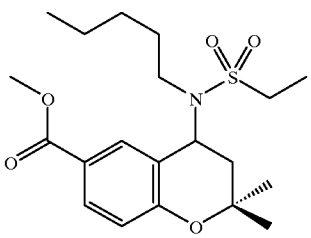

is obtained analogously to the procedure indicated in Example 2 from 0.0091 mol of 4-N-ethylsulfonylamino-6-methoxycarbonyl-2,2-dimethyl-chroman, 0.013 mol of NaH (as an 80% strength suspension in oil) and 0.0126 mol of pentyl iodide in anhydrous DMA.

Oily amorphous product.

Example 61

4-(N-Ethylsulfonyl-N-1-hexyl)amino-6-methoxycarbonyl-2,2-dimethylchroman

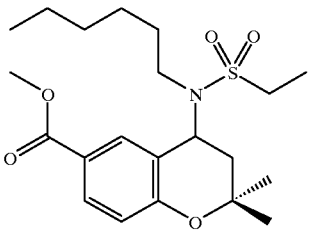

is obtained analogously to the procedure indicated in Example 2 from 0.0091 mol of 4-N-ethylsulfonylamino-6-methoxycarbonyl-2,2-dimethyl-chroman, 0.013 mol of NaH (as an 80% strength suspension in oil) and 0.0126 mol of hexyl iodide in anhydrous DMA.

Oily amorphous product.

Example 62

4-(N-Ethylsulfonyl-N-methyl)amino-6,7-dimethoxy-2,2-dimethylchroman

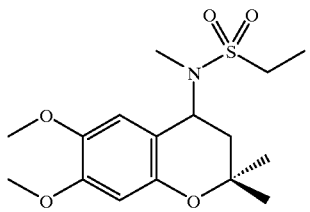

a) 6,7-Dimethoxy-2,2-dimethyl-4-chromanone oxime is obtained by reaction of 0.0189 mol of 6,7-dimethoxy-2,2-dimethyl-4-chromanone with 0.02 mol of hydroxylamine hydrochloride in a mixture of 20 ml of methanol and 20 ml of pyridine for 20 hours at 60–80° C. After removing the solvent by distillation, the colorless crystalline product is obtained by treating the residue with water, melting point 110° C.

b) 4-Amino-6,7-dimethoxy-2,2-dimethyl-4-chroman hydrochloride is obtained analogously to the procedure indicated in Example 1b) by catalytic hydrogenation of 6,7-dimethoxy-2,2-dimethyl-4-chromanone oxime and subsequent work-up in the presence of hydrochloric acid. Colorless crystals substance of melting point 210–215° C.

c) 4-N-Ethylsulfonylamino-6,7-dimethoxy-2,2-dimethylchroman is obtained analogously to the procedure indicated in Example 1c) (variant 1) from 4-amino-6,7-dimethoxy-2,2-dimethyl-4-chroman hydrochloride and ethanesulfonyl chloride in THF in the presence of triethylamine.

Colorless crystalline product, melting point 132–135° C.

d) 4-(N-Ethylsulfonyl-N-methyl)amino-6,7-dimethoxy-2,2-dimethylchroman is obtained analogously to the procedure indicated in Example 2 from 0.0036 mol of 4-N-ethylsulfonylamino-6,7-dimethoxy-2,2-dimethylchroman, 0.00504 mol of NaH (as an 80% strength suspension in oil) and 0.0054 mol of methyl iodide in anhydrous DMA.

Amorphous viscous oil.

Example 63

7-Chloro-4-(N-ethylsulfonyl-N-methyl)amino-6-fluoro-2,2-dimethylchroman

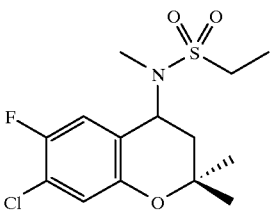

a) 2-Fluoro-5-acetoxychlorobenzene is obtained by reaction of 3-chloro-4-fluorophenol in acetic anhydride at 80° C. for 6 hours.

Colorless, crystalline product, melting point 42–46° C.

b) 4-Chloro-5-fluoro-2-hydroxyacetophenone is obtained by heating a mixture of 0.0705 mol of 2-fluoro-5acetoxychlorobenzene with 0.148 mol of anhydrous aluminum chloride with mechanical stirring at 120° C. for about 3 hours, decomposition of the reaction mixture with an ice water/ice mixture and filtration of the precipitate. Colorless crystalline substance by treatment with activated carbon in methanol and, after distillation of the solvent, by subsequent digestion with a mixture of n-heptane and diidopropyl ether.

Colorless crystals,
melting point 66–71° C.

c) 7-Chloro-6-fluoro-2,2-dimethyl-4-chromanone is obtained analogously to the procedure indicated in Example 18 b) from 4-chloro-5fluoro-2-hydroxyacetophenone and acetone in the presence of pyrrolidine in acetonitrile as solvent.

Colorless to slightly yellow amorphous residue.

d) 7-Chloro-6-fluoro-2,2-dimethyl-4-chromanone oxime is obtained analogously to the procedure indicated in Example 1 a) from 7-chloro-6-fluoro-2,2-dimethyl-4-chromanone and hydroxylamine hydrochloride Crystalline product,
melting point 120–125° C.

e) 7-Chloro-6-fluoro-2,2-dimethyl-4-amino aminochroman hydrochloride is obtained analogously to the procedure indicated in Example 1 b) catalytic hydrogenation of 7-chloro-6-fluoro-2,2-dimethyl-4-chromanone oxime and work-up in the presence of hydrochloric acid.

Two melting points:
1st melting point: 258–260° C. with fresh crystallization of the melt,
2nd melting point>310° C.

f) 7-Chloro-6-fluoro-2,2-dimethyl-4-ethylsulfonylaminochroman is obtained analogously to the procedure indicated in Example 1 c) by reaction of 7-chloro-6-fluoro-2,2-dimethyl-4-aminochroman hydrochloride with ethanesulfonyl chloride in the presence of TEA in THF.

g) 7-Chloro-4-(N-ethysulfonyl-N-methyl)amino-6-fluoro-2,2-dimethyl-chroman is obtained analogously to the procedure indicated in Example 2 by reaction of 7-chloro-6-fluoro-2,2-dimethyl-4-ethylsulfonylaminochroman hydrochloride with sodium hydride and methyl iodide.

Colorless crystalline substance,
melting point 104–107° C.

Example 64

4-(N-Ethylslfony-N-methyl)amino-2,2,6-trimethylchroman

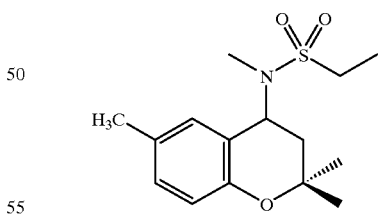

a) 2,2,6-Trimethyl-4-chromanone is obtained analogously to the procedure indicated in Example 18 b) from 5-methyl-2-hydroxyacetophenone and acetone in the presence of pyrrolidine in acetonitrile as solvent.

Amorphous oily product.

b) 2,2,6-Trimethyl-4-chromanone oxime is obtained analogously to the procedure indicated in Example 1 a) from 2,2,6-trimethyl-4-chromanone and hydroxylamine hydrochloride.

Crystalline product, melting point 120–124° C.

c) 4-Amino-2,2,6-trimethyl-4-aminochroman hydrochloride is obtained analogously to the procedure indicated in Example 1 b) by catalytic hydrogenation of 2,2,6-trimethyl-4-chromanone oxime and work-up in the presence of hydrochloric acid.

Two melting points:

1st melting point: 245–258° C. with fresh crystallization of the melt,

2nd melting point>310° C.

d) 4-(Ethysulfonylamino-2,2,6-dimethylchroman is obtained analogously to the procedure indicated in Example 1 c) by reaction of 4-amino-2,2,6-trimethylchroman hydrochloride with ethanesulfonyl chloride in the presence of TEA in THF.

Colorless crystalline product, melting point 114–117° C.

4-(N-Ethylslfony-N-methyl)amino-2,2,6-trimethylchroman is obtained analogously to the procedure indicated in Example 2 by reaction of 4-ethylsulfonylamino-2,2,6-dimethylchroman with sodium hydride and methyl iodide.

Colorless crystalline substance, melting point 107° C.

Example 65

6,7-Dichloro-4-(N-ehtylsulfonyl-N-methyl)amino-2,2-dimethyl-chroman

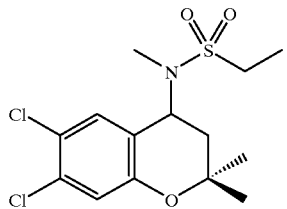

a) 4,5-Dichloro-2-hydroxyacetophenone is obtained analogously to the procedure indicated in Example 63 b) from 3.4-dichlorphenyl acetate and anhydrous, active aluminum chloride.

Colorless to slightly yellowish-colored crystalline substance, melting point 100–103° C.

The 3,4-dichlorphenyl acetate used is obtained as a brown oil from 3,4-dichlorophenol and acetic anhydride analogously to the procedure described in Example 63 a).

b) 6,7-Dichloro-2,2-dimethyl-4-chromanone is obtained analogously to the procedure indicated in Example 18 b) from 4,5-dichloro-2-hydroxyacetophenone and acetone in the presence of pyrrolidine in acetonitrile as solvent.

Amorphous brown oily product.

c) 6,7-Dichloro-2,2-dimethyl-4-chromanone oxime is obtained analogously to the procedure indicated in Example 1 a) from 6,7-dichloro-2,2-dimethyl-4-chromanone and hydroxylamine hydrochloride.

Crystalline product, melting point 115–121° C.

d) 4-Amino-6,7-dichloro-2,2-dimethylchroman hydrochloride is obtained analogously to the procedure indicated in Example 1 b) by catalytic hydrogenation of 6,7-dichloro-2,2-dimethyl-4-chromanone oxime and work-up in the presence of hydrochloric acid.

Two melting points:

1st melting point: 260–262° C. with fresh crystallization of the melt,

2nd melting point>310° C.

e) 6,7-Dichloro-2,2-dimethyl-4-N-ethylsulfonylaminochroman is obtained analogously to the procedure indicated in Example 1c) by reaction of 4-amino-6,7-dichloro-2,2-dimethylchroman hydrochloride and ethanesulfonyl chloride in the presence of TEA in THF.

Colorless crystalline product, melting point 116–120° C.

f) 6,7-Dichloro-4-(N-ethylsulfonyl-N-methyl)amino-2,2-dimethylchroman is obtained analogously to the procedure indicated in Example 2 by reaction of 6.7-dichloro-2,2-dimethyl-4-N-ethylsulfonylaminochroman with sodium hydride and methyl iodide.

Colorless crystalline substance, melting point 102–106° C.

Example 66

4-(N-Ethylsulfonyl-N-methyl)amino-6-fluoro-7-pyrrolidino2,2-dimethylchroman

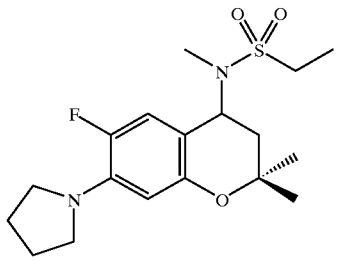

a) 4,5-Difluoro-2-hydroxyacetophenone is obtained analogously to the procedure indicated in Example 63 b) from 3,4-difluorophenyl acetate and anhydrous, active aluminum chloride. Colorless to slightly yellowish-colored crystalline substance, melting point 43–46° C. (crystallization under n-heptane).

The 3,4-difluorophenyl acetate used is obtained as a pale oil from 3,4-difluorophenol and acetic anhydride analogously to the procedure described in Example 63 a).

b) 6-Fluoro-7-pyrrodino-2,2-dimethyl-4-chromanone is obtained analogously to the procedure indicated in Example 18 b) from 4,5-difluoro-2-hydroxyacetophenone and acetone in the presence of 1.1 mol equivalents of pyrrolidine in acetonitrile as solvent, the fluorine atom in the 7-position being exchanged for pyrrolidine in addition to the chromanone ring closure. For further purification, the product can be separated by chromatography on silica gel and an 8:1 mixture of toluene/ethyl acetate. Crystallization under n-heptane.

Colorless to slightly yellow crystalline product, melting point 96–98° C.

c) 6-Fluoro-7-pyrrolidino-2,2-dimethyl-4-chromanone oxime is obtained analogously to the procedure indicated in Example 1 a) from 6-fluoro-7-pyrrolidino-2,2-dimethyl-4-chromanone and hydroxylamine hydrochloride.

Crystalline product, melting point 148–152° C.

d) 6-Fluoro-7-pyrrolidino-2,2-dimethyl-4-aminochroman dihydrochloride is obtained analogously to the procedure indicated in Example 1 b) by catalytic hydrogenation of 6-fluoro-7-pyrrolidino-2,2-dimethyl-4-chromanone oxime and work-up in the presence of hydrochloric acid.

Colorless crystalline product

Melting point: 124–137° C. with decomposition.

e) 6-Fluoro-7-pyrrolidino-2,2-dimethyl-4-N-ethylsulfonylaminochroman is obtained analogously to the procedure indicated in Example 1 c) by reaction of 6-fluoro-7-pyrrolidino-2,2-dimethyl-4-aminochroman dihydrochloride and ethanesulfonyl chloride in the presence of TEA in THF.

Colorless crystalline product, melting point 157–159° C. (from a mixture of diisopropyl ether and methanol).

f) 4-(N-Ethylsulfonyl-N-methyl)amino-6-fluoro-7-pyrrolidino-2,2-dimethylchroman is obtained analogously to the procedure indicated in Example 2 by reaction of 6-fluoro-7-pyrrolidino-2,2-dimethyl-4-N-ethylsulfonylaminochroman with sodium hydride and methyl iodide.

Colorless crystalline substance, melting point 136–138° C.

Example 67

4-(N-Ethylsulfonyl-N-methyl)amino-6-fluorochroman

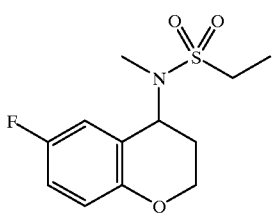

a) 6-Fluoro-4-chromanone oxime is obtained analogously to the procedure indicated in Example 1 a) from 6-fluoro-4-chromanone and hydroxylamine hydrochloride.

Crystalline product, melting point 106–107° C.

b) 6-Fluoro-4-aminochroman hydrochloride is obtained analogously to the procedure indicated in Example 1 b) by catalytic hydrogenation of 6-fluoro-4-chromanone oxime and work-up in the presence of hydrochloric acid.

Melting point: 252° C. (decomposition).

c) 6-Fluoro-4-ethylsulfonylaminochroman is obtained analogously to the procedure indicated in Example 1 c) by reaction of 6-fluoro-4-aminochroman hydrochloride and ethanesulfonyl chloride in the presence of TEA and THF.

Colorless crystalline substance, melting point 107–108° C.

d) 4-(N-Ethylsulfonyl-N-methyl)amino-6-fluorochroman is obtained analogously to the procedure indicated in Example 2 by reaction of 6-fluoro-4-ethylsulfonylaminochroman with sodium hydride and methyl iodide.

Colorless to pale yellow oil.

Example 68

4-(N-Butyl-N-ethylsulfonyl)amino-6-fluorochroman

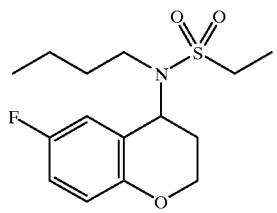

is obtained analogously to the procedure indicated in Example 2 by reaction of 6-fluoro-4-ethylsulfonylaminochroman with sodium hydride and iodobutane.

Colorless to pale yellow oil.

Example 69

4-(N-Ethylsulfonyl-N-ethyl)amino-6-fluoro-2,2-dimethyl-chroman

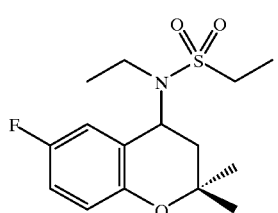

is obtained analogously to the procedure indicated in Example 2 from 4-N-ethysulfonylamino-6-fluoro-2,2-dimethylchroman and ethyl iodide.

Amorphous oily product.

Example 70

4-(N-Ethylsulfonyl-N-propyl)amino-6-fluoro-2,2-dimethyl-chroman

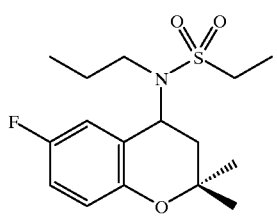

is obtained analogously to the procedure indicated in Example 2 from 4-N-ethylsulfonylamino-6-fluoro-2,2-dimethylchroman and propyl iodide.

Amorphous oily product.

Example 71

4-(N-Butyl-N-ethylsulfonyl)amino-6-fluoro-2,2-dimethyl-chroman

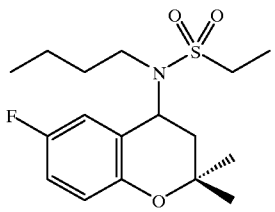

is obtained analogously to the procedure indicated in Example 2 from 4-N-ethylsulfonylamino-6-fluoro-2,2-dimethylchroman and butyl iodide.

Amorphous oily product.

Example 72

4-(N-Ethylsulfonyl-N-(4,4,4-trifluorobutyl)amino-6-fluoro-2,2-dimethylchroman

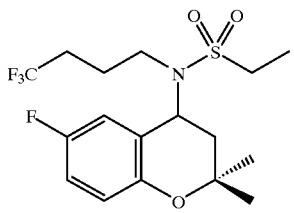

is obtained analogously to the procedure indicated in Example 2 from 4-N-ethylsulfonylamino-6-fluoro-2,2-dimethylchroman and 4,4,4-trifluorobutyl iodide.

Amorphous oily product.

Example 73

4-(N-Ethylsulfonyl-N-hexyl)amino-6-fluoro-2,2-dimethyl-chroman

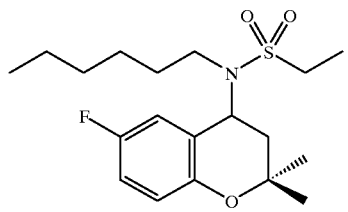

is obtained analogously to the procedure indicated in Example 2 from 4-N-ethylsulfonylamino-6-fluoro-2,2-dimethylchroman and hexyl iodide.

Amorphous oily product.

Example 74

4-(N-Ethylsulfonyl-N-methyl)amino-6-fluoro-2,2-tetramethylenechroman

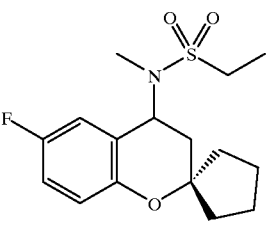

a) 6-Fluoro-2,2-tetramethylene-4-chromanone is obtained analogously to the procedure indicated in Example 18 b) from 5-fluoro-2-hydroxyacetophenone and cyclopentanone in the presence of pyrrolidine in acetonitrile as solvent.

Amorphous brown product b) 6-Fluoro-2,2-tetramethylene-4-chromanone oxime is obtained analogously to the procedure indicated in Example 1 a) from 6-fluoro-2,2-tetramethylene-4-chromanone and hydroxylamine hydrochloride.

Colorless to pale brown-colored crystalline substance, melting point 107–110° C.

c) 4-Amino-6-fluoro-2,2-tetramethylenechroman hydrochloride is obtained analogously to the procedure indicated in Example 1 b) by catalytic hydrogenation of 6-fluoro-2, 2-tetramethylene-4-chromanone oxime and work-up in the presence of hydrochloric acid, melting point 259–261° C. with decomposition.

d) 4-Ethylsulfonylamino-6-fluoro-2,2-tetramethylenechroman is obtained analogously to the procedure indicated in Example 1 c) by reaction of 4-amino-6-fluoro-2,2-tetramethylenechroman hydrochloride and ethanesulfonyl chloride in the presence of TEA in THF.

Colorless crystalline substance, melting point 111–113° C.

e) 4-(N-Ethylsulfonyl-N-methyl)amino-6-fluoro-2,2-tetramethylenechroman is obtained analogously to the procedure indicated in Example 2 from 4-ethylsulfonylamino-6-flouro-2,2-tetramethylenechroman and methyl iodide.

Amorphous oily product.

Example 75

4-[N-Ethylsulfonyl-N-(4,4,4-trifluorobutyl)]amino-6-fluoro2,2-tetramethylenechroman.

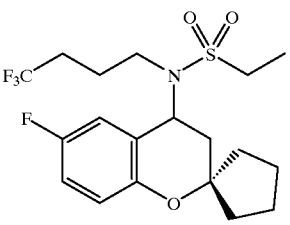

is obtained analogously to the procedure indicated in Example 2 from 4-ethylsulfonylamino-6-fluoro-2,2-tetramethylenechroman and 4,4,4-trifluorobutyl iodide.

Viscous oily amorphous product.

Example 76

4-[N-Ethylsulfonyl-N-(4,4,4-trifluorobutyl)]amino-6-fluoro-2,2-pentamethylenechroman

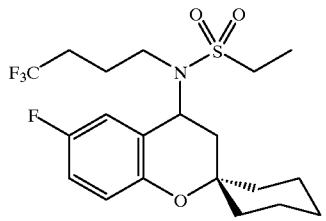

a) 6-Fluoro-2,2-pentamethylene-4-chromanone is obtained analogously to the procedure indicated in Example 18 b) from 5-fluoro-2-hydroxyacetophenone and cyclohexanone in the presence of pyrrolidine in acetonitrile as solvent.

Pale amorphous product.

b) 6-Fluoro-2,2-pentamethylene-4-chromanone oxime is obtained analogously to the procedure indicated in Example 1 a) from 6-fluoro-2,2-pentamethylene-4-chromanone and hydroxylamine hydrochloride.

Viscous amorphous product.

c) 4-Amino-6-fluoro-2,2-pentamethylenechroman hydrochloride is obtained analogously to the procedure indicated in Example 1 b) by catalytic hydrogenation of 6-fluoro-2,2-pentamethylene-4-chromanone oxime and work-up in the presence of hydrochloric acid, melting point: 262–264° C. with decomposition.

d) 4-Ethylsulfonylamino-6-fluoro-2,2-pentamethylenechroman is obtained analogously to the procedure indicated in Example 1 c) by reaction of 4-amino-6-fluoro-2,2-pentamethylenechroman hydrochloride and ethanesulfonyl chloride in the presence of TEA in THF.

Viscous amorphous product.

e) 4-[N-Ethylsulfonyl-N-(4,4,4-trifluorobutyl)]amino-6-fluoro-2,2-pentamethylenechroman is obtained analogously to the procedure indicated in Example 2 from 4-ethylsulfonylamino-5-fluoro-2,2-pentamethylenechroman and 4,4,4-trifluorobutyl iodide.

Amorphous oily product.

Example 77

6-Ethyl-4-(N-Ethylsulfonyl-N-Methyl)Amino-2,2-Dimethyl-Chroman

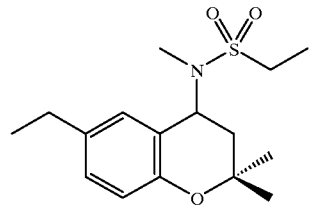

a) 5-Ethyl-2-hydroxyacetophenone is obtained analogously to the procedure indicated in Example 63 b) from 4-ethylphenyl acetate and anhydrous, active aluminum chloride. Slightly yellowish-colored oil.

The 4-ethylphenyl acetate used is obtained as an oil from 4-ethylphenol and acetic anhydride analogously to the procedure described in Example 63 a).

b) 6-Ethyl-2,2-dimethyl-4-chromanone is obtained analogously to the procedure indicated in Example 18 b) from 5-ethyl-2-hydroxyacetophenone and acetone in the presence of pyrrolidine in acetonitrile as solvent.

Pale oily amorphous product.

c) 6-Ethyl-2,2-dimethyl-4-chromanone oxime is obtained analogously to the procedure indicated in Example 1 a) from 6-ethyl-2,2-dimethyl-4-chromanone and hydroxylamine hydrochloride.

Viscous oily amorphous product.

d) 4-Amino-6-ethyl-2,2-dimethylchroman hydrochloride is obtained analogously to the procedure indicated in Example 1 b) by catalytic hydrogenation of 6-ethyl-2,2-dimethyl-4-chromanone oxime and work-up in the presence of hydrochloric acid, melting point: 201–204° C.

e) 6-Ethyl-4-N-ethylsulfonylamino-2,2-dimethylchroman is obtained analogously to the procedure indicated in Example 1 c) by reaction of 4-amino-6-ethyl-2,2-dimethylchroman hydrochloride and ethanesulfonyl chloride in the presence of TEA in THF.

Colorless crystalline substance, melting point 104–108° C.

f) 6-Ethyl-4-(N-ethylsulfonyl-N-methyl)amino-2,2-dimethylchroman is obtained analogously to the procedure indicated in Example 2 from 6-ethyl-4-N-ethylsulfonylamino-2,2-dimethylchroman and methyl iodide.

Colorless, crystalline product, melting point 76–77° C.

Example 78

6-Ethyl-4-[N-Ethylsulfonyl-N-(4,4,4-Trifluorobutyl)]Amino-2,2-Dimethylchroman

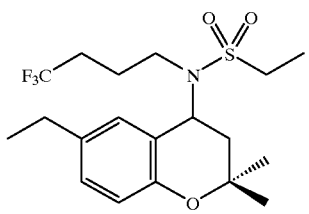

is obtained analogously to the procedure indicated in Example 2 from 6-ethyl-4-N-ethylsulfonylamino-2,2-dimethylchroman and 4,4,4-trifluorobutyl iodide.

Colorless to pale yellow-colored oil.

Example 79

7-Chloro-4-[N-Ethylsulfonyl-N-(4,4,4-Trifluorobutyl)]Amino-6-Fluoro-2,2-Dimethylchroman

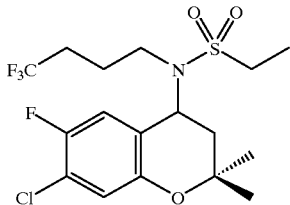

is obtained analogously to the procedure indicated in Example 2 by reaction of 7-chloro-6-fluoro-2,2-dimethyl-4-ethylsulfonylaminochroman with sodium hydride and 4,4,4-triflurobutyl iodide.

Viscous, pale yellow oil.

Example 80

4-[N-Ethylsulfonyl-N-(4,4,4-Triflurobutyl)]Amino-2,2,6-Trimethylchroman

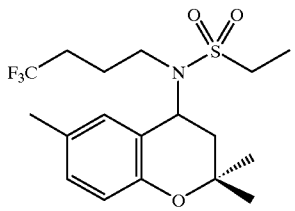

is obtained analogously to the procedure indicated in Example 2 by reaction of 4-ethylsulfonylamino-2,2,6-trimethylchroman with sodium hydride and 4,4,4-trifluorobutyl iodide.

Viscous, pale yellow oil.

Example 81

6,7-Dichloro-4-[N-Ethylsulfonyl-N-(4,4,4-Triflurobutyl)]Amino-2,2-Dimethylchroman

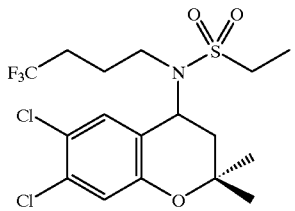

is obtained analogously to the procedure indicated in Example 2 by reaction of 6,7-dichloro-4-N-ethylsulfonylamino-2,2-dimethylchroman with sodium hydride and 4,4,4-trifluorobutyl iodide.

Viscous, pale brown oil.

Example 82

4-(N-Ethylsulfonyl-N-Methyl)Amino-6-Phenyl-2,2-Dimethyl-Chroman

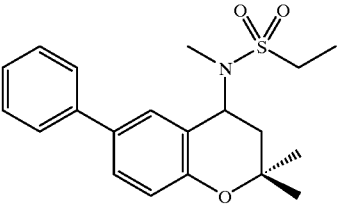

a) 2-Hydroxy-5-phenylacetophenone is obtained analogously to the procedure indicated in Example 63 b) from 4-acetoxybiphenyl and anhydrous, active aluminum chloride. Slightly yellowish-colored oil, which partially crystalizes. The 4-acetoxybiphenyl used is obtained as a colorless crystalline solid from 4-hydroxybiphenyl and acetic anhydride analogously to the procedure described in Example 63 a).

M.p. 84–86° C.

b) 2,2-dimethyl-6-phenyl-4-chromanone is obtained analogously to the procedure indicated in Example 18 b) from 2-hydroxy-5-phenylacetophenone and acetone in the presence of pyrrolidine in acetonitrile as solvent.

Dark oily amorophous product, which partially crystallizes.

c) 2,2-Dimethyl-6-phenyl-4-chromanone oxime is obtained analogously to the procedure indicated in Example 1 a) from 2,2-dimethyl-6-phenyl-4-chromanone and hydroxylamine hydrochloride. Crystalline solid, m.p. 130–134° C.

d) 4-Amino-2,2-dimethyl-6-phenylchroman hydrochloride is obtained analogously to the procedure indicated in Example 1 b) by catalytic hydrogenation of 2,2-dimethyl-6-phenyl-4-chromanone oxime and work-up in the presence of hydrochloric acid, melting point: 213–214° C. (decomposition).

e) 4-N-Ethylsulfonylamino-2,2-dimethyl-6-phenylchroman is obtained analogously to the procedure indicated in Example 1 c) by reaction of 4-amino-2,2-dimethyl-6-phenylchroman hydrochloride and ethanesulfonyl chloride in the presence of TEA in THF.

Colorless crystalline substance, melting point 162–164° C.

f) 4-(N-Ethylsulfonyl-N-methyl)amino-6-phenyl-2,2-dimethylchroman is obtained analogously to the procedure indicated in Example 2 from 4-N-ethylsulfonylamino-2,2-dimethyl-6-phenylchroman and methyl iodide.

Colorless, crystalline product, melting point 184–186° C.

Example 83

4-[N-Ethylsulfonyl-N-(4,4,4-Trifluorobutyl)]Amino-6-Phenyl-2,2-Dimethylchroman

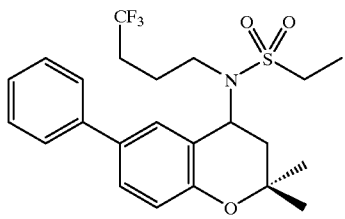

is obtained analogously to the procedure indicated in Example 2 by reaction of 4-N-ethylsulfonylamino-2,2-dimethyl-6-phenylchroman with sodium hydride and 4,4,4-trifluorobutyl iodide.

Colorless to pale yellow crystalline substance, melting point 112–114° C.

Example 84

6,8-Difluoro-4-(N-Ethylsulfonyl-N-Methyl)Amino-2,2-Dimethyl-Chroman

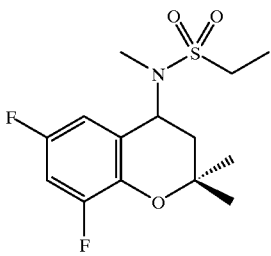

a) 3,5-Difluoro-2-hydroxyacetophenone is obtained analogously to the procedure indicated in Example 63 b) from 2,4-difluorophenyl acetate and anhydrous, active aluminum chloride.

Colorless crystalline solid,
melting point 80–94° C.

The 2,4-difluorophenyl acetate used is obtained as a slightly yellowish-colored liquid from 2,4-difluorophenol and acetic anhydride analogously to the procedure described in Example 63 a).

b) 6,8-Difluoro-2,2-dimethyl-4-chromanone is obtained analogously to the procedure indicated in Example 18 b) from 3,5-difluoro-2-hydroxyacetophenone and acetone in the presence of pyrrolidine in acetonitrile as solvent.

Dark oily amorphous product.

c) 6,8-Difluoro-2,2-dimethyl-4-chromanone oxime is obtained analogously to the procedure indicated in Example 1 a) from 6,8-difluoro-2,2-dimethyl-4-chromanone and hydroxylamine hydrochloride.

Crystalline solid,
m.p. 124–137° C.

d) 4-Amino-6,8-difluoro-2,2-dimethylchroman hydrochloride is obtained analogously to the procedure indicated in Example 1 b) by catalytic hydrogenation of 6,8-difluoro-2,2-dimethyl-4-chromanone oxime and work-up in the presence of hydrochloric acid, melting point: >310° C. (sublimation from 300° C., 1 atm).

e) 4-N-Ethylsulfonylamino-6,8-difluoro-2,2-dimethylchroman is obtained analogously to the procedure indicated in Example 1 c) by reaction of 4-amino-6,8-difluoro-2,2-dimethylchroman hydrochloride and ethanesulfonyl chloride in the presence of TEA in THF.

Colorless crystalline substance.

Melting point 124–127° C.

f) 6,8-Difluoro-4-(N-ethylsulfonyl-N-methyl)amino-2,2-dimethylchroman is obtained analogously to the procedure indicated in Example 2 from 4-N-ethylsulfonylamino-6,8-difluoro-2,2-dimethylchroman and methyl iodide.

Colorless, crystalline product, melting point 84–86° C.

Example 85

6,8-Difluoro-4-[N-Ethylsulfonyl-N-(4,4,4-Trifluorobutyl)]Amino-2,2-Dimethylchroman

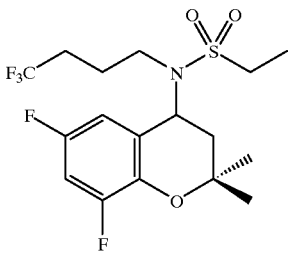

is obtained analogously to the procedure indicated in Example 2 from 4-N-ethylsulfonylamino-6,8-difluoro-2,2-dimethylchroman and 4,4,4-trifluorobutyl iodide, Colorless, crystalline product, melting point 127–129° C.

Example 86

4-[N-Ethylsulfonyl-N-(4,4,4-trifluorobutyl)]Amino-6-Fluoro-7-Pyrrolidino-2,2-Dimethylchroman

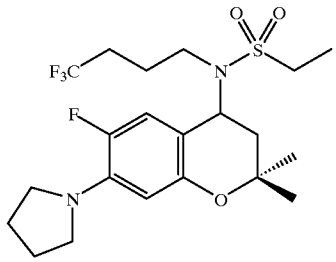

is obtained analogously to the procedure indicated in Example 2 by reaction of 6-fluoro-7-pyrrolidino-2,2-dimethyl-4N-ethylsulfonyl-aminochroman with sodium hydride and 4,4,4-trifluorobutyl iodide.

Colorless crystalline substance, melting point 137–140° C.

Example 87

6-Carboxy-4-(N-ethyl-N-Ethylsulfonyl)Amino-2,2-Dimethylchroman

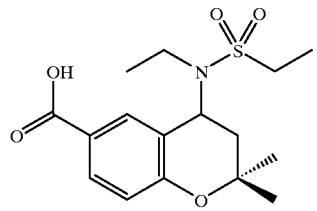

is obtained analogously to the procedure indicated in Example 23 by hydrolysis of 4-(N-ethylsulfonyl-N-ethyl)amino-6-methoxycarbonyl-2,2-dimethylchroman.

Colorless crystalline compound,
melting point 217–220° C.

Example 88

6-Carboxy-4-(N-Ethylsulfonyl-N-Propyl)Amino-2,2-Dimethylchroman

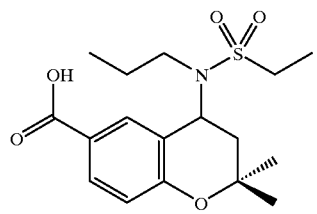

is obtained analogously to the procedure indicated in Example 23 by hydrolysis of 4-(N-ethylsulfonyl-N-propyl)amino-6-methoxycarbonyl-2,2-dimethylchroman.

Colorless crystalline compound,
melting point 165–169° C.

Example 89

6-Carboxy-4-(N-Cyclopropylmethyl-N-Ethylsulfonyl)Amino-2,2-Dimethylchroman

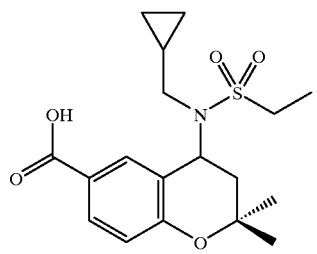

is obtained analogously to the procedure indicated in Example 23 by hydrolysis of 4-(N-cyclopropylmethyl-N-ethylsulfonyl)amino-6-methoxycarbonyl-2,2-dimethylchroman.

Colorless crystalline compound,
melting point 184–188° C.

Example 90

6-Carboxy-4-(N-Ethylsulfonyl-N-Pentyl)Amino-2,2-dimethylchroman

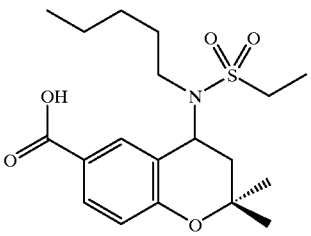

is obtained analogously to the procedure indicated in Example 23 by hydrolysis of 4-(N-ethylsulfonyl-N-pentyl)amino-6-methoxycarbonyl-2,2-dimethylchroman.

Colorless crystalline compound,
melting point 156–158° C.

Example 91

6-Carboxy-4-(N-Ethylsulfonyl-N-Hexyl)Amino-2,2-dimethylchroman

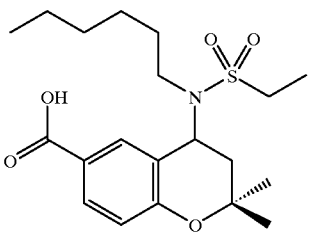

is obtained analogously to the procedure indicated in Example 23 by hydrolysis of 4-(N-ethylsulfonyl-N-hexyl)amino-6-methoxycarbonyl-2,2-dimethylchroman.

Colorless crystalline compound,
melting point 154–158° C.

Example 92

6-Carboxamido-4-(N-Ethyl-N-Ethylsulfonyl)Amino-2,2-dimethylchroman

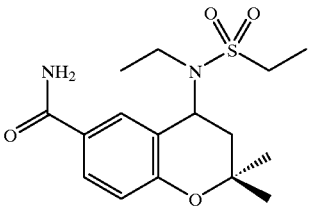

is obtained analogously to the procedure indicated in Example 24 from 6-carboxy-4-(N-ethyl-N-ethylsulfonyl)amino-2,2-dimethylchroman, carbonyldiimidazole and ammonia.

Colorless crystalline substance.
melting point 173–175° C.

Example 93

6-Carboxamido-4-(N-ethylsulfonyl-N-propyl)amino-2,2-dimethylchroman

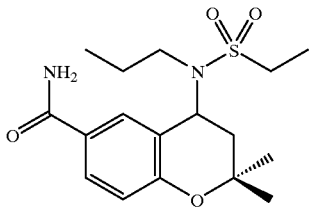

is obtained analogously to the procedure described in Example 24 from 6-carboxy-4-(N-ethylsulfonyl-N-propyl)amino-2,2-dimethylchroman, carbonyldimidazole and ammonia.
Colorless crystalline substance.
Melting point 185–188° C.

Example 94

6-Carboxamido-4-(N-cyclopropylmethyl-N-ethylsulfonyl)amino-2,2-dimethylchroman

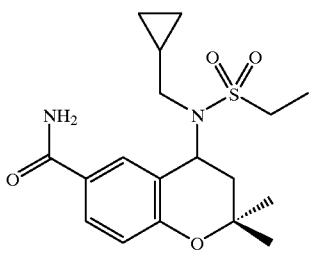

is obtained analogously to the procedure described in Example 24 from 6-carboxy-4-(N-cyclopropylmethyl-N-ethylsulfonyl)amino-2,2-dimethylchroman, carbonyldiimidazole and ammonia.
Colorless crystalline substance.
Melting point 196–199° C.

Example 95

6-Carboxamido-4-(N-ethylsulfonyl-N-pentyl)amino-2,2-dimethylchroman

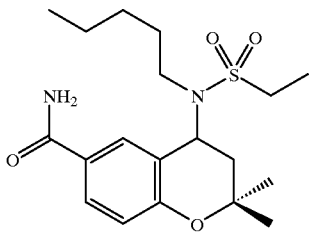

is obtained analogously to the procedure described in Example 24 from 6-carboxy-4-(N-ethylsulfonyl-N-pentyl)amino-2,2-dimethylchroman, carbonyldimidazole and ammonia.
Colorless crystalline substance.
Melting point 168–172° C.

Example 96

6-Carboxamido-4-(N-ethylsulfonyl-N-hexyl)amino-2,2-dimethylchroman

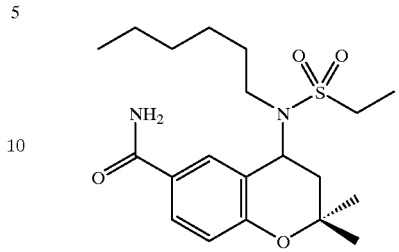

is obtained analogously to the procedure described in Example 24 from 6-carboxy-4-(N-ethylsulfonyl-N-hexyl)amino-2,2-dimethylchroman, carbonyldimidazole and ammonia.
Colorless crystalline substance.
Melting point 148–152° C.

Example 97

6-Cyano-4-(N-ethyl-N-ethylsulfonyl)amino-2,2-dimethyl-chroman

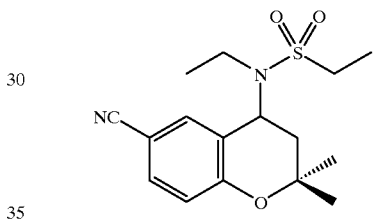

is obtained analogously to the procedure indicated in Example 25 from 6-carboxamido-4-(N-ethyl-N-ethylsulfonyl)amino-2,2-dimethylchroman and subsequent purification by column chromatography on silica gel using a mixture of 10 parts of methylene chloride and 1 part of methanol as eluent.
Colorless to pale yellow crystalline substance.
melting point: 127–130° C.

Example 98

6-Cyano-4-(N-ethylsulfonyl-N-propyl)amino-2,2-dimethyl-chroman

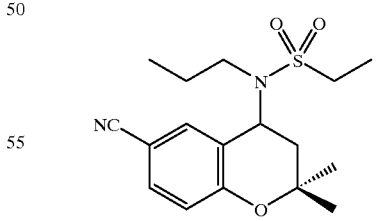

is obtained analogously to the procedure indicated in Example 25 from 6-carboxamido-4-(N-ethylsulfonyl-N-propyl)amino-2,2-dimethylchroman and subsequent purification by column chromatography on silica gel using a mixture of 10 parts of methylene chloride and 1 part of methanol as eluent.
Colorless to pale yellow crystalline substance.
melting point: 127–130° C.

Example 99

6-Cyano-4-(N-cyclopropylmethyl-N-ethylsulfonyl)amino-2,2-dimethylchroman

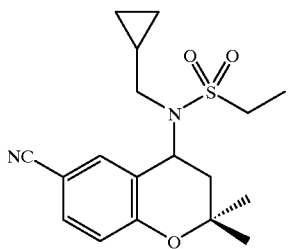

is obtained analogously to the procedure indicated in Example 25 from 6-carboxamido-4-(N-cyclopropylmethyl-N-ethylsulfonyl)amino-2,2-dimethylchroman and subsequent purification by column chromatography on silica gel using a mixture of 10 parts of methylene chloride and 1 part of methanol as eluent.

Colorless to pale yellow crystalline substance.
melting point: 127–130° C.

Example 100

6-Cyano-4-(N-ethylsulfonyl-N-pentyl)amino-2,2-dimethyl-chroman

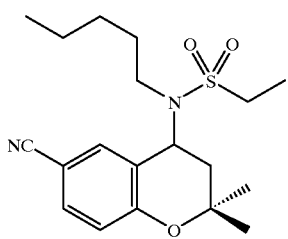

is obtained analogously to the procedure indicated in Example 25 from 6-carboxamido-4-(N-ethylsulfonyl-N-pentyl)amino-2,2-dimethylchroman and subsequent purification by column chromatography on silica gel using a mixture of 10 parts of methylene chloride and 1 part of methanol as eluent.

Viscous oily liquid.

Example 101

6-Cyano-4-(N-ethylsulfonyl-N-hexyl)amino-2,2-dimethylchroman

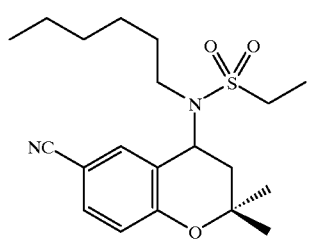

is obtained analogously to the procedure indicated in Example 25 from 6-carboxamido-4-(N-ethylsulfonyl-N-hexyl)amino-2,2-dimethylchroman and subsequent purification by column chromatography on silica gel using a mixture of 10 parts of methylene chloride and 1 part of methanol as eluent.

Viscous oily liquid.

Example 102

4-(N-Ethoxycarbonylmethyl-N-ethylsulfonyl)amino-6-fluoro-2,2-dimethylchroman

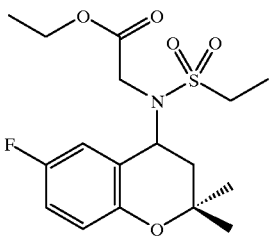

is obtained analogously to the procedure indicated in Example 2 from 4-N-ethylsulfonylamino-6-fluoro-2,2-dimethylchroman and ethyl bromoacetate.

Colorless, crystalline product.
melting point: 112–114° C.

Example 103

4-[N-Ethylsulfonyl-N-methyl]amino-6-fluoro-2,2-pentamethylenechroman

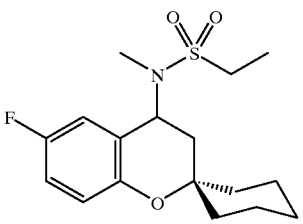

is obtained analogously to the procedure indicated in Example 2 from 4-ethylsulfonylamino-6-fluoro-2,2-pentamethylenechroman and methyl iodide.

Colorless crystalline compound,
melting point 73–74° C.

Example 104

4-(N-Isopropyloxycarbonylmethyl-N-ethylsulfonyl)amino-6-fluoro-2,2-dimethylchroman

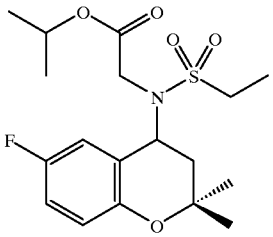

is obtained analogously to the procedure indicated in Example 2 from 4-N-ethylsulfonylamino-6-fluoro-2,2-dimethylchroman and isopropyl bromoacetate.

Colorless to pale yellow liquid.

Example 105

4-(N-Ethylsulfonyl-N-methyl)amino-6-methoxy-2,2-dimethylchroman

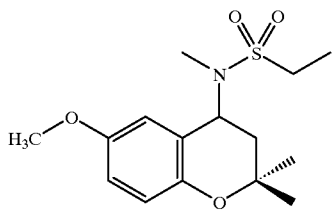

a) 6-Hydroxy-2,2-dimethyl-4-chromanone is obtained analogously to the procedure indicated in Example 18 b) from 2,5-dihydroxyacetophenone and acetone in the presence of pyrrolidine in acetonitrile as solvent.

Crystalline compound, melting point 147–149° C.

b) 6-Methoxy-2,2-dimethyl-4-chromanone a suspension of 0.03 mol of 6-hydroxy-2,2-dimethyl-4-chromanone, 75 ml of acetone and 16.1 g of anhydrous powdered potassium carbonate is treated with an excess of 3.6 ml of methyl iodide and the reaction mixture is heated at 50–55° C. for 20 hours. The solvent is removed by vacuum distillation, the residue is treated with water and the oil which separates is extracted with ethyl acetate. After drying the organic phase over anhydrous sodium sulfate, the solvent is removed by distillation and 6-methoxy-2,2-dimethyl-4-chromanone is obtained as an oily liquid.

c) 6-Methoxy-2,2-dimethyl-4-chromanone oxime is obtained analogously to the procedure indicated in Example 1 a) from 6-methoxy-2,2-dimethyl-4-chromanone and hydroxylamine hydrochloride.

Crystalline solid, m.p. 108–112° C.

d) 4-Amino-6-methoxy-2,2-dimethylchroman hydrochloride is obtained analogously to the procedure indicated in Example 1 b) by catalytic hydrogenation of 6-methoxy-2,2-dimethyl-4-chromanone oxime and work-up in the presence of hydrochloric acid, melting point: 250–251° C.

e) 4-N-Ethylsulfonylamino-6-methoxy-2,2-dimethylchroman is obtained analogously to the procedure indicated in Example 1 c) from 4-amino-6-methoxy-2,2-dimethylchroman hydrochloride and ethansulfonyl chloride in the presence of TEA in THF.

Colorless crystalline substance, melting point 131–133° C.

f) 4-(N-Ethylsulfonyl-N-methyl)amino-6-methoxy-2,2-dimethylchroman is obtained analogously to the procedure indicated in Example 2 from 4-N-ethylsulfonylamino-6-methoxy-2,2-dimethylchroman and methyl iodide.

Colorless, crystalline product, melting point 68–70° C.

Example 106

4N-Ethylsulfonylamino-2,2-dimethyl-6-methylsulfonyl-oxychroman

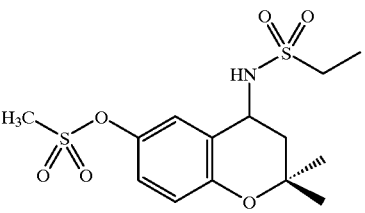

a) 2,2-Dimethyl-6-methylsulfonyloxychromanone a mixture of 0.03 mol of 6-hydroxy-2,2-dimethyl-4-chromanone, 16.1 g of anhydrous powdered potassium carbonate and 10 ml of methanesulfonic acid in 80 ml of anhydrous DMF is heated at 80° C. for 10 hours. The solvent is then removed by distillation under reduced pressure and the residue is stirred, after addition of 150 ml of water, for 2 hours. The crystalline precipitate is filtered, washed several times with water and dried in a stream of air.

Colorless solid, melting point 108–110° C.

b) 2,2-Dimethyl-6-methylsulfonyloxychromanone oxime is obtained analogously to the procedure indicated in Example 1 a) from 2,2-dimethyl-6-methylsulfonyloxychromanone and hydroxylamine hydrochloride.

Crystalline solid, m.p. 166–167° C.

c) 4-Amino-6-methylsulfonyloxy-2,2-dimethylchroman hydrochloride is obtained analogously to the procedure indicated in Example 1 b) by catalytic hydrogenation of 2,2-dimethyl-6-methylsulfonyloxychromanone oxime and work-up in the presence of hydrochloric acid, melting point: 229–231° C.

e) 4-N-Ethylsulfonylamino-2,2-dimethyl-6-methylsulfonyloxychroman is obtained analogously to the procedure indicated in Example 1 c) from 4-amino-6-methylsulfonyloxy-2,2-dimethylchroman hydrochloride and ethanesulfonyl chloride in the present of TEA in THF.

Colorless crystalline substance, melting point 97–100° C.

Example 107

4-(N-Ethylsulfonyl-N-methyl)amino-2,2-dimethyl-6-methylsulfonyloxychroman

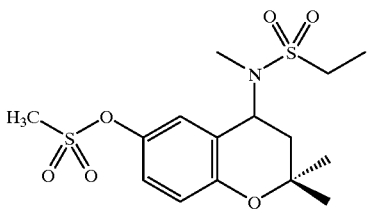

is obtained analogously to the procedure indicated in Example 2 from 4-N-ethylsulfonylamino-2,2-dimethyl-6-methylsulfonyloxychroman and methyl iodide.

Colorless,crystalline product, melting point 137–139° C.

Example 108

4-(N-Methylsulfonyl-N-methyl)amino-2,2,6,7-tetramethylchroman was obtained analogously to the procedure indicated in Example 2 from 4-N-methylsulfonylamino-2,2,6,7-tetramethylchroman and ethyliodide. Colorless crystals, melting point: 119–121° C.

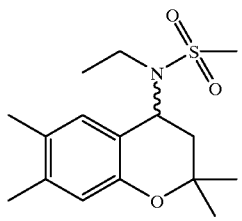

The hydrochloride of 4-Amino-2,2,6,7-tetramethylchroman (melting point >270° C.) was prepared by hydrogenation of 2,2,6,7-tetramethyl-4-chromanone oxime (melting point 162–163° C.). The oxime was generated by known methods as described above from the corresponding 2,2,6,7-tetramethyl-4-chromanone. Conversion of 4-Amino-2,2,6,7-tetramethylchroman with the corresponding alkylsulfonylchlorides as described in example 1 (variant 1) resulted in methylsulfonylamino-2,2,6,7-tetramethylchroman (colorless oil) and ethylsulfonylamino-2,2,6,7-tetramethylchroman (colorless oil) respectively.

Example 109

4-(N-Methylsulfonyl-N-methyl)amino-2,2,6,7-tetramethylchroman

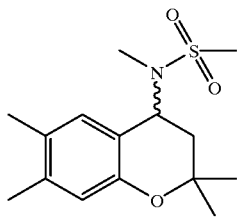

was obtained analogously to the procedure indicated in example 2 from 4-N-methylsulfonylamino-2,2,6,7-tetramethylchroman and methyliodide.

Colorless crystals, melting point: 105–107° C.

Example 110

4-(N-Ethylsulfonyl-N-hexyl)amino-2,2,6,7-tetramethylchroman

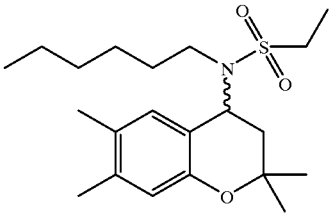

was obtained analogously to the procedure indicated in example 2 from 4-N-ethylsulfonylamino-2,2,6,7-tetramethylchroman and hexyliodide.

Example 111

4-N-Ethylsulfonyl-N-ethyl)amino-2,2,6,7-tetramethylchroman

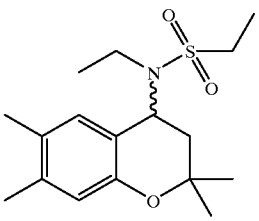

was obtained analogously to the procedure indicated in example 2 from 4-N-ethylsulfonylamino-2,2,6,7-tetramethylchroman and ethyliodide.

Colorless crystals, melting point: 93–95° C.

Example 112

4-(N-Ethylsulfonyl-N-Butyl)amino-2,2,6,7-tetramethylchroman

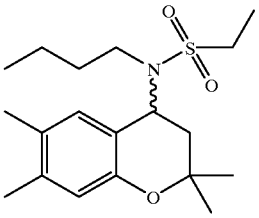

was obtained analogously to the procedure indicated in Example 2 from 4-N-Ethylsulfonylamino-2,2,6,7-tetramethylchroman and Butyl iodide.

Colorless crystals, melting point: 81–83° C.

Example 113

4-(N-ethylsulfonyl-N-methyl)amino-2,2,6,7-tetramethylchroman

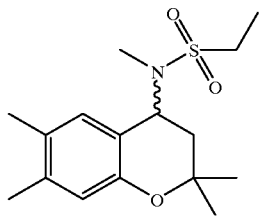

was obtained analogously to the procedure indicated in example 2 from 4-N-ethylsulfonylamino-2,2,6,7-tetramethylchroman and methyliodide.
Colorless crystals, melting point: 132–134° C.

Example 114

4-(N-Ethylsulfonyl-N-butyl)amino-7-methoxy-2,2-dimethylchroman

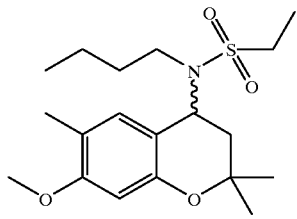

was obtained analogously to the procedure indicated in example 2 from 4-N-ethylsulfonylamino-7-methoxy-2,2-dimethylchroman and butyl iodide.
Colorless oil.

The hydrochloride of 4-amino-7-methoxy-2,2-dimethylchroman (melting point 239–241° C.) was prepared by hydrogenation of 7-methoxy-2,2-dimethyl-4-chromanone oxime (melting point 124–126° C.). The oxime was generated by known methods from the corresponding 7-methoxy-2,2-dimethyl-4-chromanone. Conversion of 4-Amino-7-methoxy-2,2-dimethylchroman with the corresponding alkylsulfonylchlorides as described in example 1 (variant 1) resulted in methylsulfonylamino-7-methoxy-2,2-dimethylchroman (colorless oil) and ethylsulfonylamino-7-methoxy-2,2-dimethylchroman (melting point 111–113° C.) respectively.

Example 115

4-(N-Ethylsulfonyl-N-ethyl)amino-7-methoxy-2,2-dimethylchroman

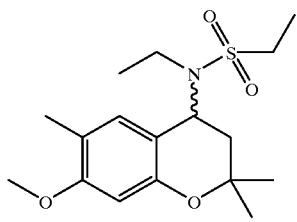

was obtained analogously to the procedure indicated in example 2 from 4-N-Ethylsulfonylamino-7-methoxy-2,2-dimethylchroman and ethyliodide. Colorless oil.

Example 116

4-(N-Ethylsulfonyl-N-methyl)amino-7-methoxy-2,2-dimethylchroman

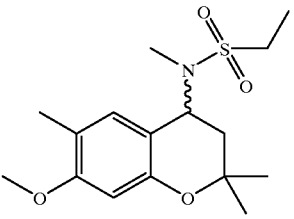

was obtained analogously to the procedure indicated in example 2 from 4-N-ethylsulfonylamino-7-methoxy-2,2-dimethylchroman and methyliodide. Colorless oil.

Example 117

4-(N-Ethylsulfonyl-N-methyl)amino-6-(4,4,4-trifluorobutyl)oxy-2,2-dimethylchroman

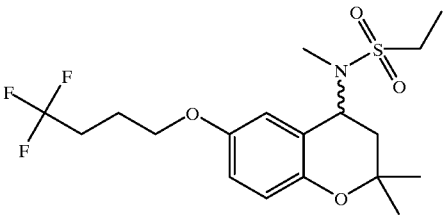

was obtained analogously to the procedure indicated in Example 2 from 4-(N-Ethylsulfonylamino-6-(4,4,4-trifluorobutyl)oxy-2,2-dimethylchroman and methyliodide. Colorless crystalline compound from mixture of n-heptane/diisopropyl ether. Melting point 68–72° C.

4-(N-Ethylsulfonylamino-6-(4,4,4-trifluorobutyl)oxy-2,2-dimethylchroman (melting point 84–90° C.) was obtained in the sequence of synthetic steps indicated above starting from 6-hydroxy-2,2-dimethyl-4-chromanone (obtained from 2-acetoxyhydroquinone and acetone, melting point 147–149° C.) via 6-(4,4,4-trifluorobutyl)oxy-2,2-dimethyl-4-chromanone (obtained from 6-hydroxy-2,2dimethyl-4-chromanone and 4,4,4-trifluorobutyl iodide, melting point 53–55° C.) and 6-(4,4,4-trifluorobutyl)oxy-2,2-dimethyl-4-chromanoneoxime (obtained from 6-(4,4,4-trifluorobutyl)oxy-2,2-dimethyl-4-chromanone and hydroxylamine hydrochloride, melting point 94–97° C.) and 4-amino-6-(4,4,4-trifluorobutyl)oxy-2,2-dimethylchroman (obtained from 6-(4,4,4-trifluorobutyl)oxy-2,2-dimethyl-4-chromanoneoxime and catalytic hydrogenation with Raney nickel, melting point 47–49° C.) and following reaction of 4-amino-6-(4,4,4-trifluorobutyl)oxy-2,2-dimethylchroman and ethanesulfonylchloride.

Example 118

6-(4-Bromophenyl)-4-(N-ethylsulfonyl)-N-methyl)amino-2,2-dimethylchroman

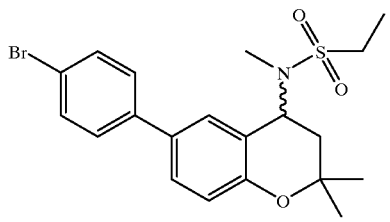

was obtained analogously to the procedure in example 2 from 6-(4-Bromophenyl)-4-N-ethylsulfonylamino-2,2-dimethylchroman and methyliodide.

Melting point 160–170° C.

6-(4-Bromophenyl)-4-N-ethylsulfonylamino-2,2-dimethylchroman (melting point 122–135° C.) was obtained in the sequence of synthetic steps indicated above starting from 3-acetyl-4'bromo-4-hydroxybiphenyl (obtained from 4'-bromo-4-acetoxybiphenyl and aluminum chloride by Friess rearrangement, dark brown oil) via 6-(4-bromophenyl)-2,2-dimethyl-4-chromanone (obtained from 3-acetyl-4'bromo-4-hydoxybiphenyl and acetone, viscous oil) and 6-(4-bromophenyl)-2,2-dimethyl-4-chromanone oxime (obtained brom 6-(4-Bromophenyl)-4-amino-2,2-dimethylchroman hydrochloride (obtained from 6-(4-bromphenyl)-2,2-dimethyl-4-chromanon oxime and catalytic hydrogenation with Raney nickel and treatment with a solution of Hcl in diethylester, melting point 166–170° C.) and following reaction of 4-amino-6-(4-Bromophenyl)-2,2-dimethylchroman hydrochloride and ethanesulfonylchloride in presence of triethlamine.

Example 119

4-(N-Ethylsulfonyl-N-methyl)amino-2,2-dimethyl-6-methoxychroman

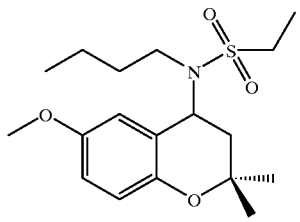

was obtained analogously to the procedure indicated in Example 2 from 4-N-ethylsulfonylamino-2,2-dimethyl-6-methoxychroman and butyl iodide. Colorless crystalline product, melting point 78–80° C.

Example 120

The entantiomers of (÷)-4-(N-Ethylsulfonyl-N-methyl)amino-6-fluoro-2,2-dimethylchroman and (−)-4-(N-Ethylsulfonyl-N-methyl)amino-6-fluoro-2,2-dimethylchroman ([alpha]=24.5°] were obtained by racemic mixture of 4-(N-Ethylsulfonyl-N-methyl)amino-6-fluoro-2,2-dimethylchroman by chiral chromatography (CSP Chiralpak AD 250-4.6, elution solvent: n-Hexane÷Ethanol: 40÷1).

Example 121

The enantiomers of (÷)-4-(N-butyl N-ethylsulfonyl)amino-6-fluoro-2,2-dimethylchroman and (−)-4-(N-abutyl N-ethylsulfonyl)amino-6-fluoro-2,2-dimethylchroman ([alpha]=−53.3°] were obtained were racemic mixture of 4-(N-butyl N-ethylsulfonyl)amino-6-fluoro-2,2-dimethylchroman by chiral chromatography (CSP Chiralpak AD 250-4.6, elution solvent: n-Hexane÷Ethanol: 80÷1).

Example 122

4-(N-Methylsulfonyl-N-isopropyl)amino-2,2,6-trimethylchroman

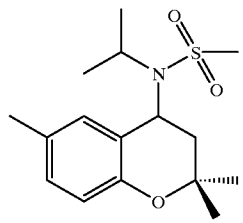

was obtained analogously to the procedure indicated in Example 2 from 4-N-methylsulfonylamino-2,2,6-trimethylchroman and isopropyl iodide. Colorless crystalline product, melting point 140° C.

Example 123

4-[N-Methylsulfonyl-N-(3-methylbutyl)]amino-2,2,6-trimethylchroman

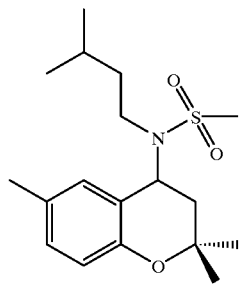

was obtained analogously to the procedure indicated in Example 2 from 4-N-methylsulfonylamino-2,2,6-trimethylchroman and 3-methylbutyl iodide. Viscous oil.

Example 124

4-[N-Ethylsulfonyl-N-(3-ethoxypropyl)amino-2,2,6-trimethylchroman

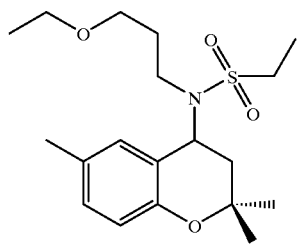

was obtained analogously to the procedure indicated in Example 2 from 4-N-ethylsulfonylamino-2,2,6-trimethylchroman and 3-ethoxypropyl iodide. Viscous oil.

The following examples were prepared from precursors known from the literature analogously to the methods indicated in the description. For the preparation of a few of the compounds, some chemical standard reactions, such as alkylations, amidations, reductions, halogenations etc. were additionally used, which should be evident to the person skilled in the art. The compounds were recrystallized from the solvent indicated in each case. If no solvent is indicated, the melting points indicated are those of the crude products, which could completely be markedly below those of the corresponding pure substances. Compounds without an indicated melting point were isolated as oils.

| Ex. | Structure | M.p. | Recryst. t | from | IC$_{50}$ ($\mu$Mol) |
|---|---|---|---|---|---|
| 125 | 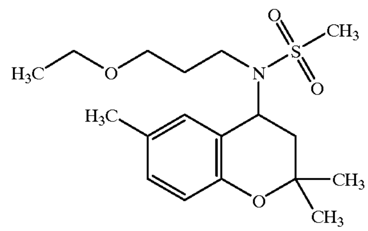 | 66 | 5 | | 0.485 |
| 126 | 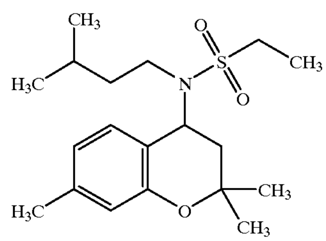 | 110 | 1 | | |
| 127 | 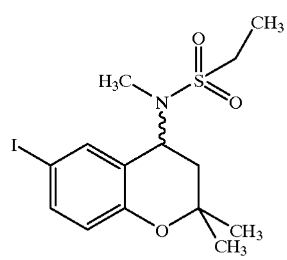 | 92 | 2 | | 29 |
| 128 | 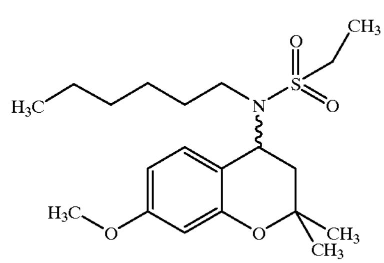 | | | | 3.35 |
| 129 | 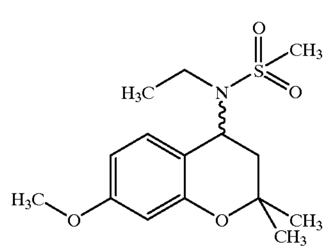 | | | | 15.9 |

-continued

| Ex. | Structure | M.p. | Recryst. from | IC$_{50}$ ($\mu$Mol) |
|---|---|---|---|---|
| 130 | 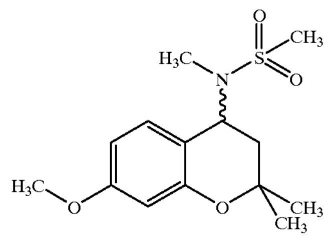 | | | 4.21 |
| 131 | 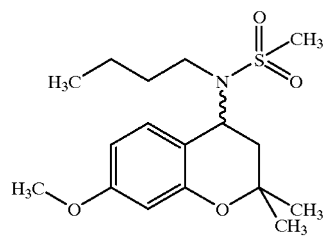 | | | 3.74 |
| 132 | 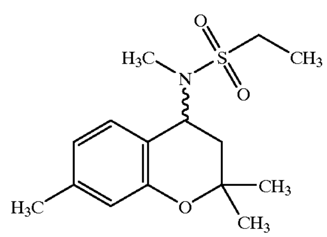 | 119 | 1 | 8.51 |
| 133 | 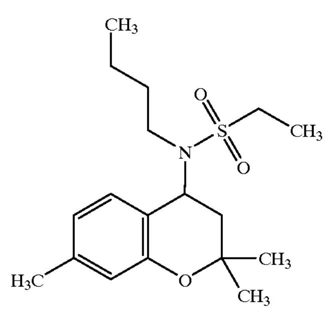 | | | 2.51 |
| 134 | 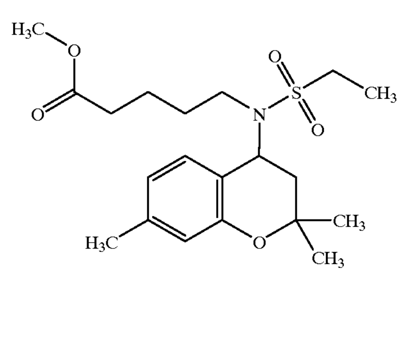 | | | 5.47 |

-continued

| Ex. | Structure | M.p. | Recryst. from t | IC$_{50}$ ($\mu$Mol) |
|---|---|---|---|---|
| 135 | 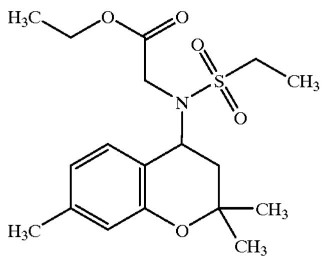 | | | 4.99 |
| 136 | 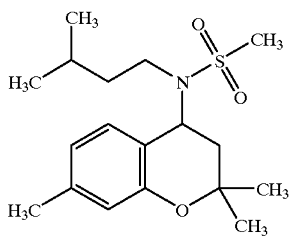 | 94 | 1 | 9.45 |
| 137 | 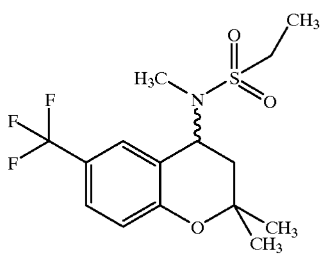 | 101 | 2 | 0.56 |
| 138 | 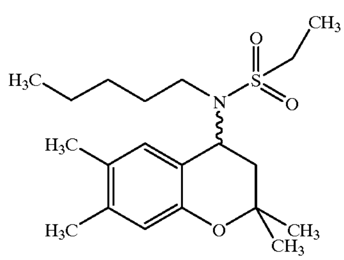 | | | 1.95 |
| 139 | 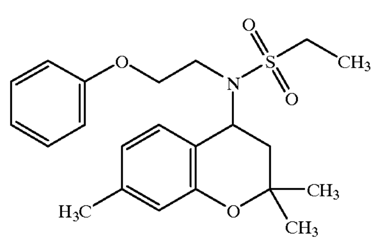 | | | |
| 140 | 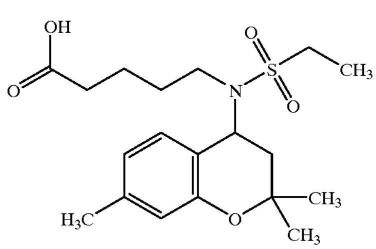 | | | |

-continued

| Ex. | Structure | M.p. | Recryst. t from | IC$_{50}$ ($\mu$Mol) |
|---|---|---|---|---|
| 141 | 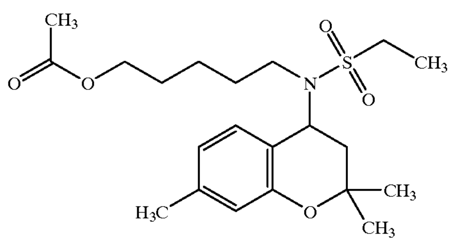 | | | 7.53 |
| 142 | 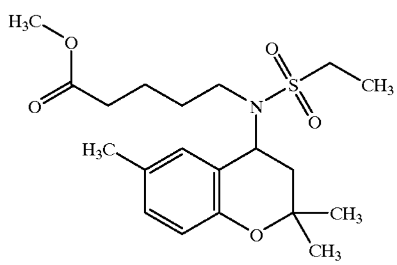 | | | 0.94 |
| 143 | 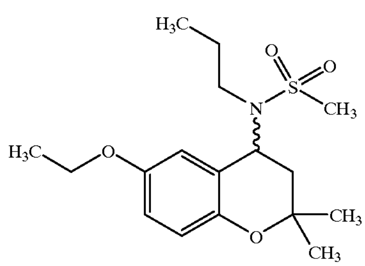 | 117 | 1 water | 0.495 |
| 144 | 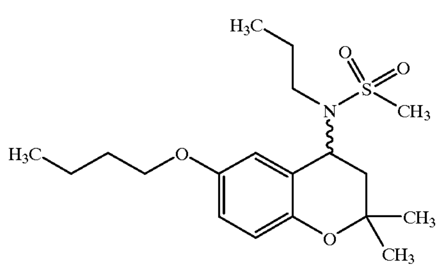 | 85 | 1 water | 0.059 |
| 145 | 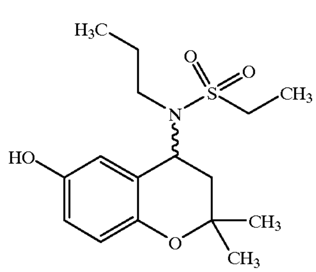 | 174 | 1 petroleum ether | 54.1 |

| Ex. | Structure | M.p. | t | Recryst. from | IC$_{50}$ ($\mu$Mol) |
|---|---|---|---|---|---|
| 146 | 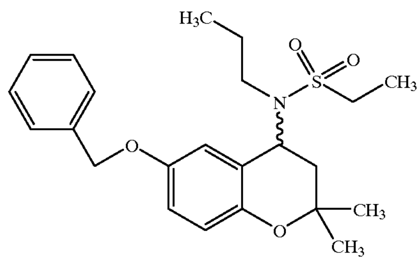 | 102.5 | 0.5 | petroleum ether | 0.093 |
| 147 | 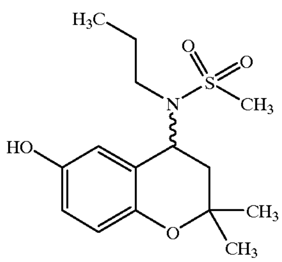 | 147 | 1 | petroleum ether | 29.7 |
| 148 | 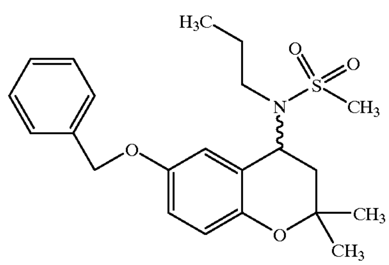 | 94 | 1 | heptane/ethyl acetate | 0.075 |
| 149 | 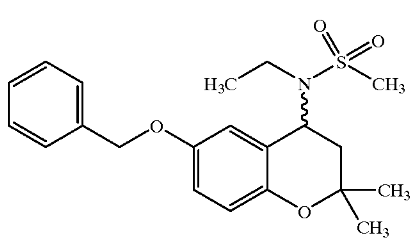 | 105 | 1 | diisopropyl ether/ petroleum ether 1:1 | 0.125 |
| 150 | 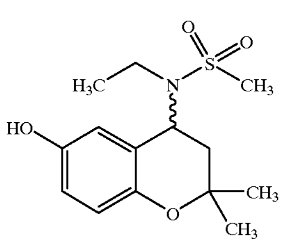 | 159.5 | 1 | diisopropyl ether | 61.5 |

-continued

| Ex. | Structure | M.p. | t | Recryst. from | IC$_{50}$ ($\mu$Mol) |
|---|---|---|---|---|---|
| 151 | 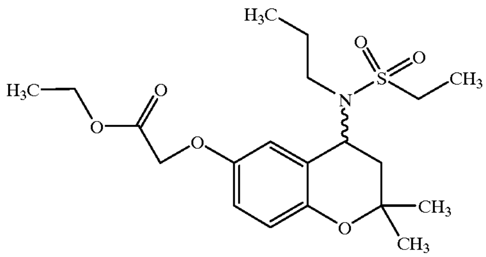 | 53 | 1 | petroleum ether/ diisopropyl ether | |
| 152 | 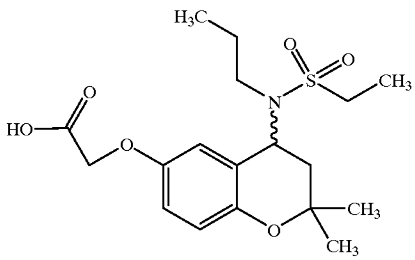 | 172 | 1 | aq. HCl | |
| 153 | 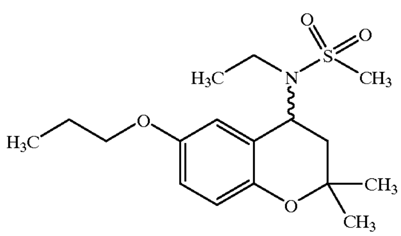 | 59 | 1 | petroleum ether | 0.2 |
| 154 | 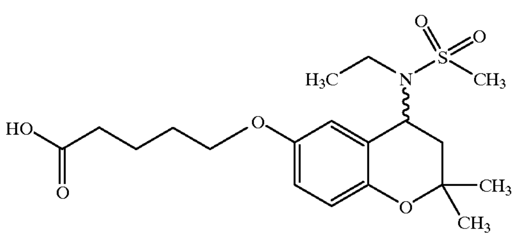 | 163 | 1 | aq. HCl | 30 |
| 155 | 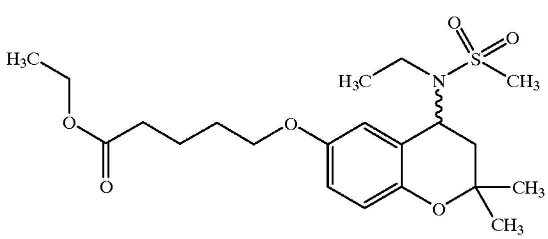 | 56 | 1 | petroleum ether | 0.092 |
| 156 | 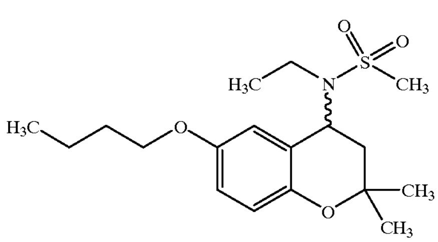 | 115 | 1 | petroleum ether | 0.055 |

| Ex. | Structure | M.p. | t | Recryst. from | IC$_{50}$ (μMol) |
|---|---|---|---|---|---|
| 157 | 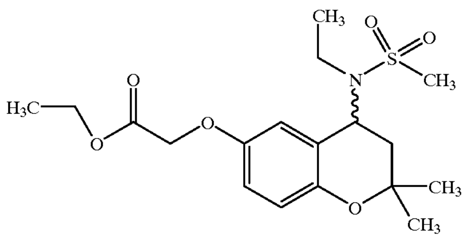 | | | | |
| 158 | 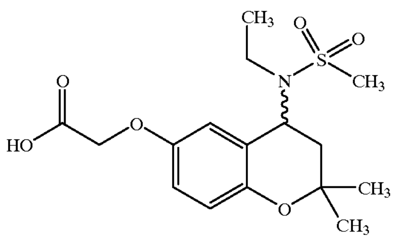 | 157 | 1 | aq. HCl | |
| 159 | 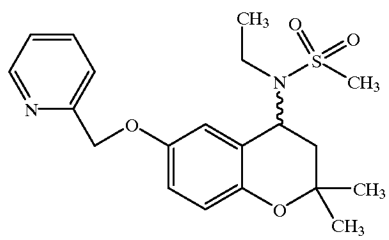 | 88 | 1 | diisopropyl ether | |
| 150 | 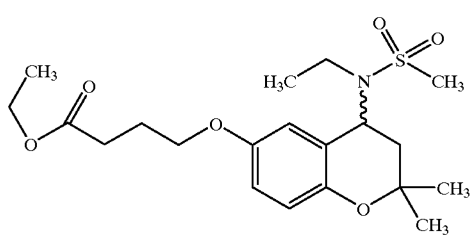 | 41 | 1 | petroleum ether | |
| 151 | 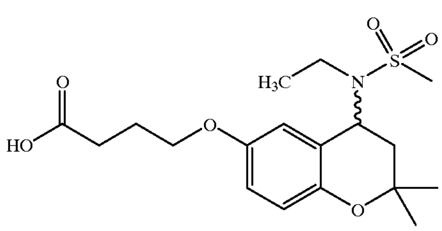 | 111 | 1 | aq. HCl | 5.47 |
| 152 | 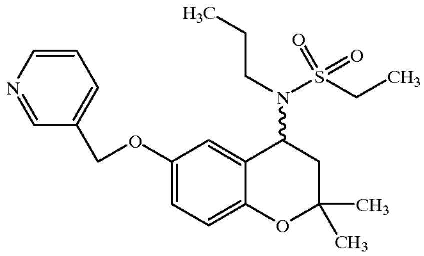 | 95.5 | 0.5 | petroleum ether | 0.55 |

| Ex. | Structure | M.p. | Recryst. from | IC₅₀ (µMol) |
|---|---|---|---|---|
| 153 | 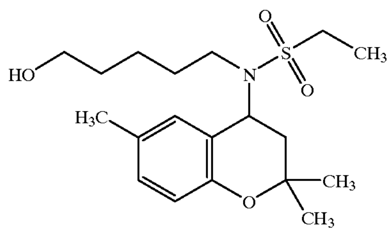 | | | |
| 154 | 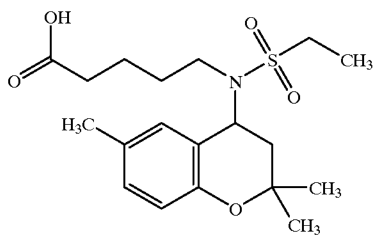 | | | |
| 155 | 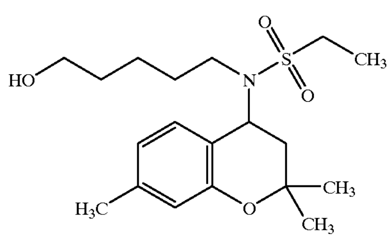 | | | |
| 156 | 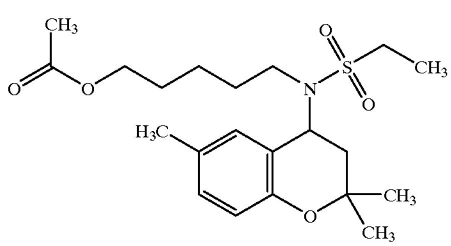 | | | 0.51 |
| 157 | 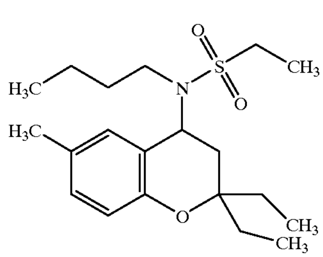 | | | |

-continued

| Ex. | Structure | M.p. | Recryst. t from | IC$_{50}$ ($\mu$Mol) |
|---|---|---|---|---|
| 158 | 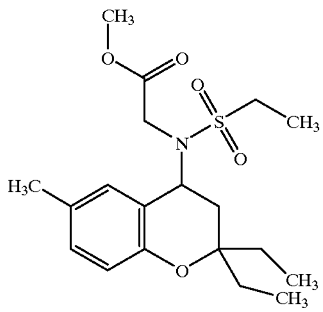 | | | 1.23 |
| 169 | 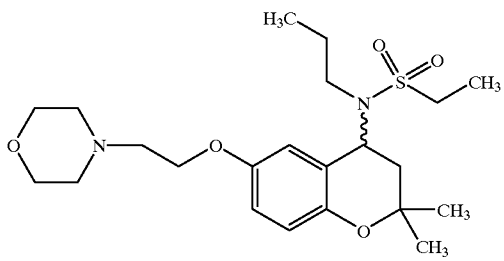 | 128 | 1 diisopropyl ether/ petroleum ether 1:1 | 2.95 |
| 170 | 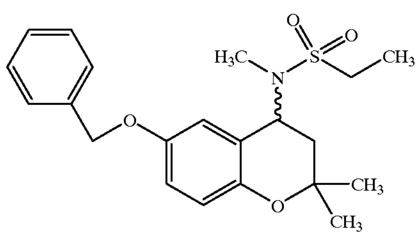 | 92 | 1 petroleum ether/ diisopropyl ether | |
| 171 | 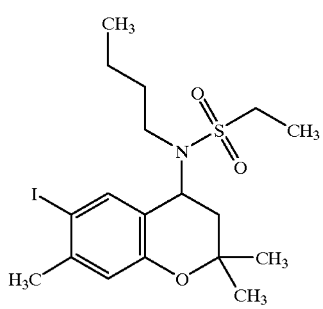 | 119 | 1 | 1.75 |
| 172 | 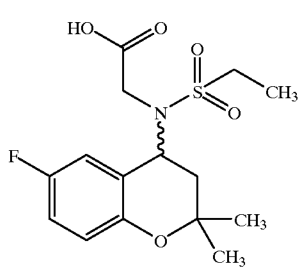 | 155 | 1 | 4.35 |

| Ex. | Structure | M.p. | t | Recryst. from | IC$_{50}$ (μMol) |
|---|---|---|---|---|---|
| 173 | 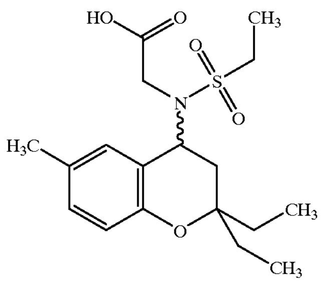 | | | | |
| 174 | 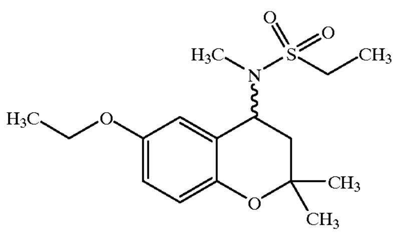 | 118 | 1 | petroleum ether/ diisopropyl ether | 1.44 |
| 175 | 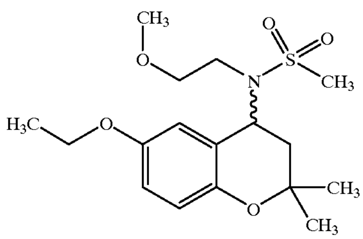 | 95 | 1 | petroleum ether | 2 |
| 176 | 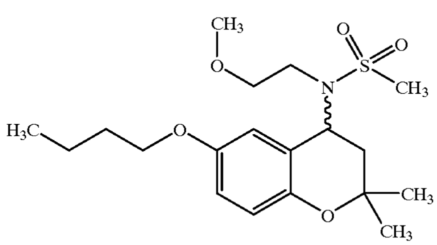 | 300 | | | 0.14 |
| 177 | 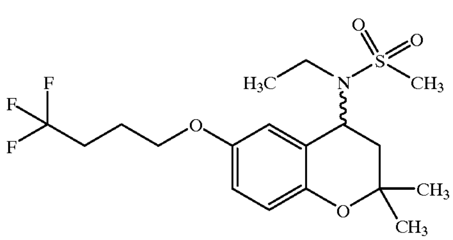 | 101 | 1 | petroleum ether | 0.027 |
| 178 | 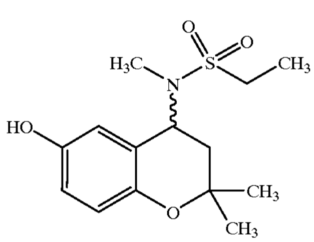 | 161 | 1 | diisopropyl ether | |

-continued

| Ex. | Structure | M.p. | t | Recryst. from | IC$_{50}$ ($\mu$Mol) |
|---|---|---|---|---|---|
| 179 | 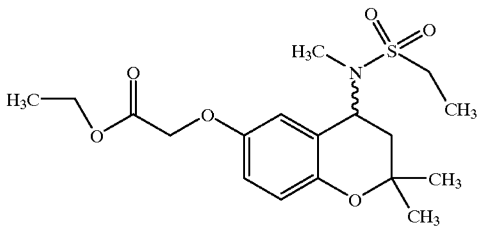 | 93 | 1 | petroleum ether/ diisopropyl ether | 0.72 |
| 180 | 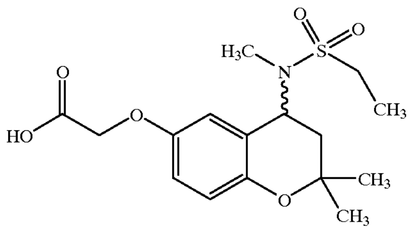 | 143 | 1 | diisopropyl ether | |
| 181 | 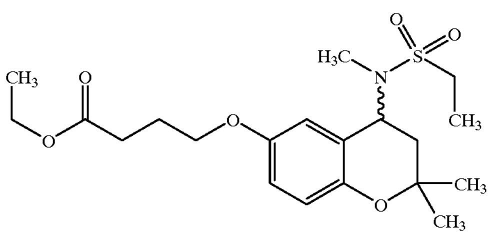 | | | | 0.19 |
| 182 | 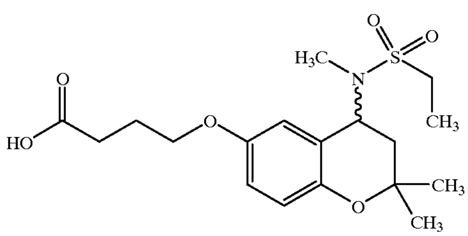 | | | | |
| 183 | 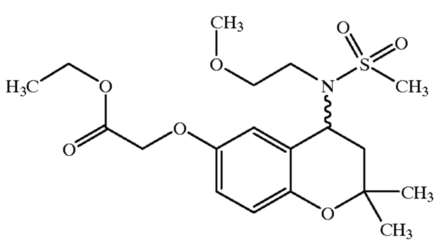 | | | | |
| 184 | 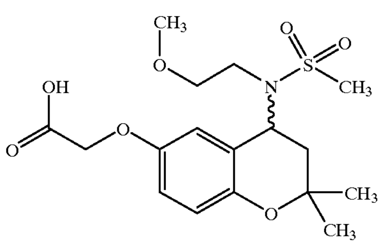 | 106 | 1 | diisopropyl ether | |

-continued

| Ex. | Structure | M.p. | Recryst. from | IC$_{50}$ (µMol) |
|---|---|---|---|---|
| 185 | 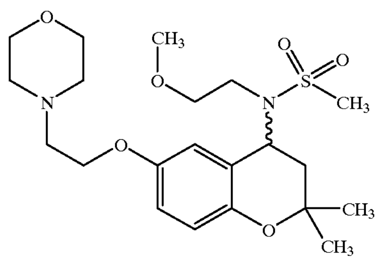 | | | |
| 186 | 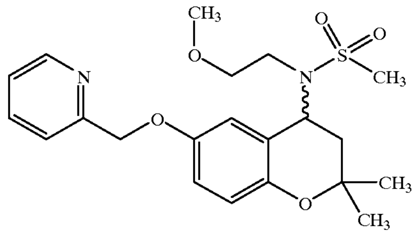 | | | 1.25 |
| 187 | 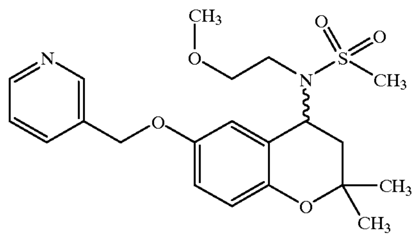 | | | 2.83 |
| 188 | 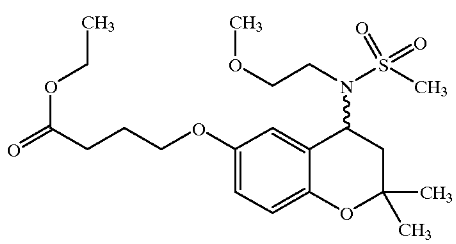 | | | |
| 189 | 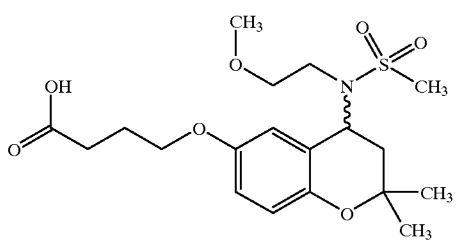 | | | |
| 190 | 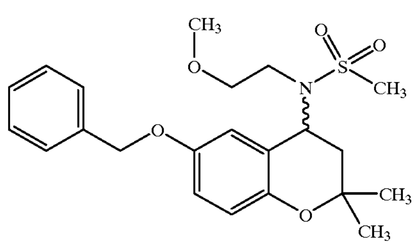 | 69 | 1 petroleum ether | |

-continued

| Ex. | Structure | M.p. | t | Recryst. from | IC$_{50}$ ($\mu$Mol) |
|---|---|---|---|---|---|
| 191 | 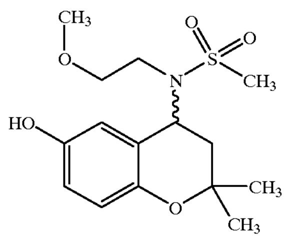 | 116 | 1 | diisopropyl ether | |
| 192 | 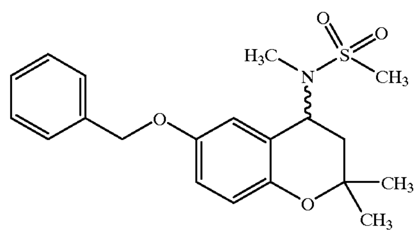 | 115 | 1 | petroleum ether/ diisopropyl ether | |
| 193 | 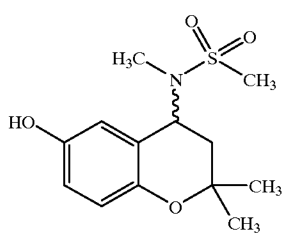 | 150 | 1 | petroleum ether/ diisopropyl ether | |
| 194 | 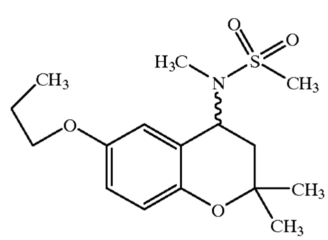 | 126 | 1 | water | 0.32 |
| 195 | 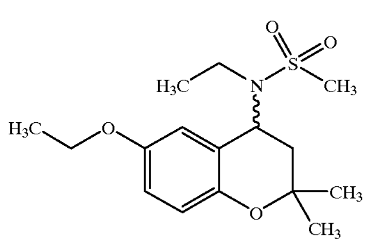 | 89 | 1 | petroleum ether/ diisopropyl ether | 0.92 |

-continued
| Ex. | Structure | M.p. | Recryst. from | IC$_{50}$ ($\mu$Mol) |
|---|---|---|---|---|
| 196 | 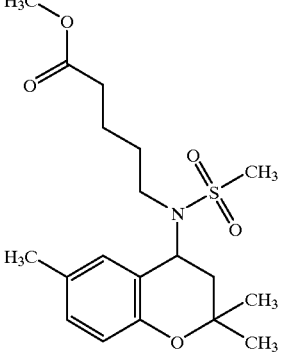 | | | 0.47 |
| 197 | 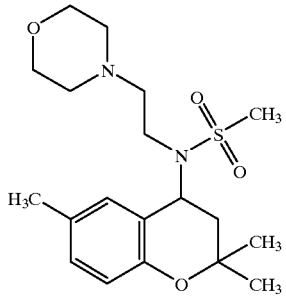 | 93 | 2 | |
| 198 | 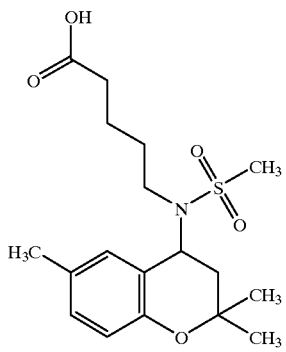 | 105 | 1 | |
| 199 | 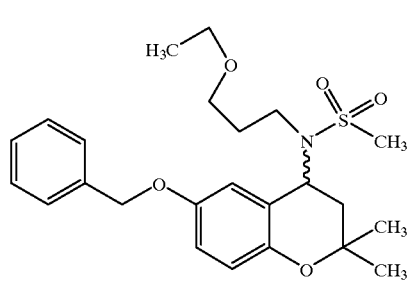 | | | 0.17 |

-continued

| Ex. | Structure | M.p. | t | Recryst. from | IC$_{50}$ ($\mu$Mol) |
|---|---|---|---|---|---|
| 206 | 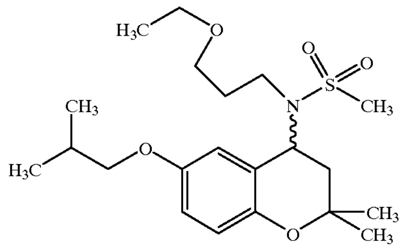 | 46 | 1 | petroleum ether | 0.083 |
| 207 | 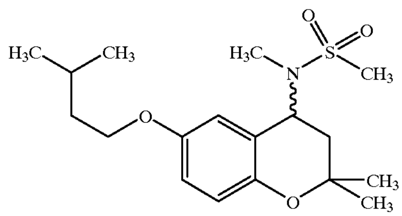 | 83 | 1 | petroleum ether | 0.051 |
| 208 | 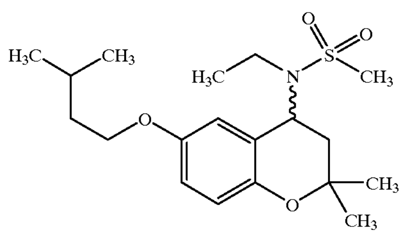 | 101.5 | 0.5 | petroleum ether | 0.07 |
| 209 | 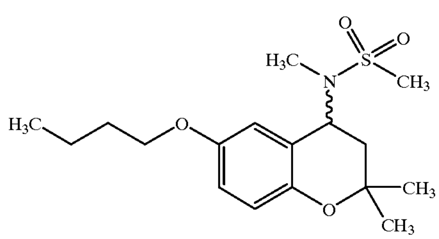 | 135 | 1 | petroleum ether | 0.09 |
| 210 | 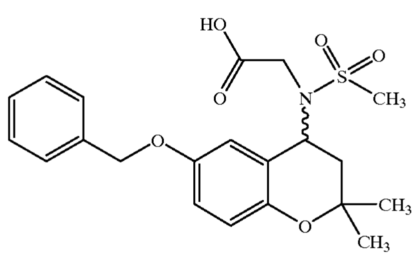 | 178 | 1 | petroleum ether | |

-continued

| Ex. | Structure | M.p. | t | Recryst. from | IC$_{50}$ ($\mu$Mol) |
|---|---|---|---|---|---|
| 211 | 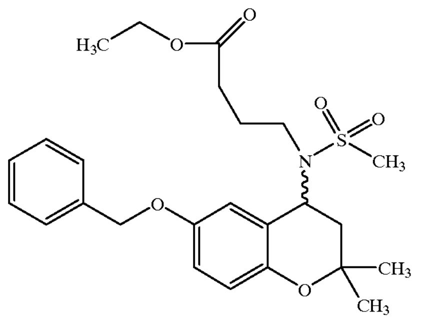 | 84 | 1 | petroleum ether/ diisopropyl ether | 0.33 |
| 212 | 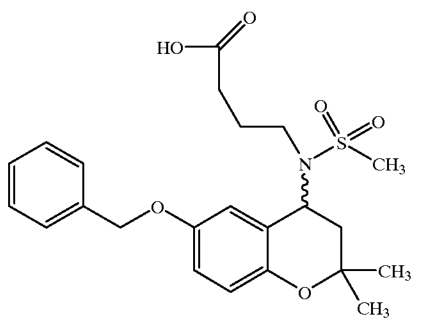 | 129 | 1 | petroleum ether | 11.25 |
| 213 | 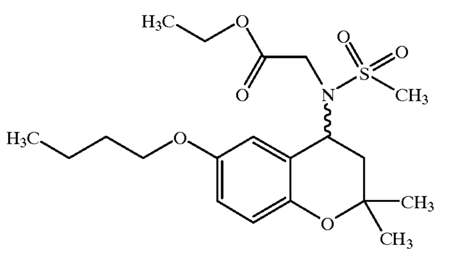 | 122 | 1 | petroleum ether | 0.047 |
| 214 | 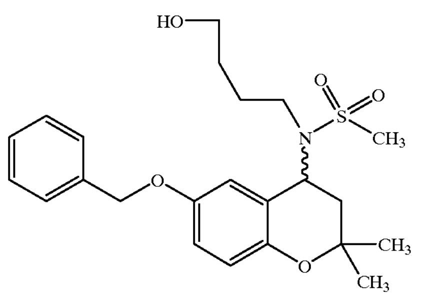 | 114 | 1 | petroleum ether/ diisopropyl ether | — |
| 215 | 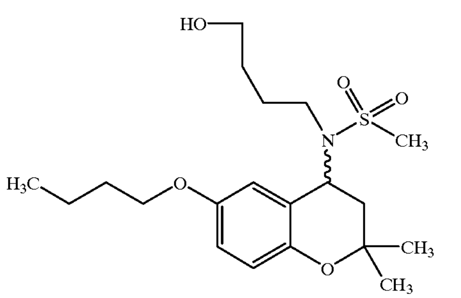 | 74 | 1 | petroleum ether | 1.0 |

-continued

| Ex. | Structure | M.p. | t | Recryst. from | IC$_{50}$ ($\mu$Mol) |
|---|---|---|---|---|---|
| 216 | 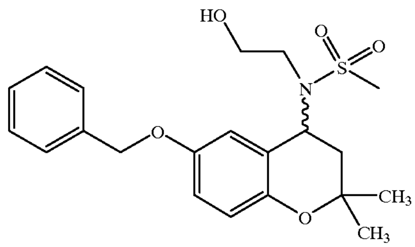 | 79 | 1 | diisopropyl ether | 0.41 |
| 217 | 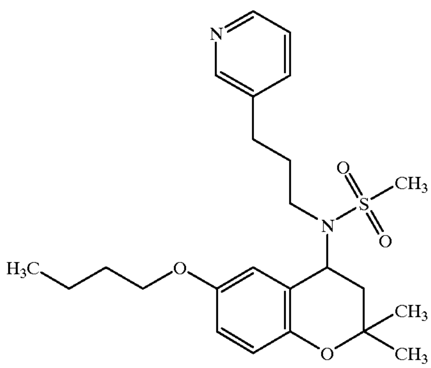 | 95 | 1 | | 0.11 |
| 218 | ClH | 108 | 1 | | 0.18 |
| 219 | 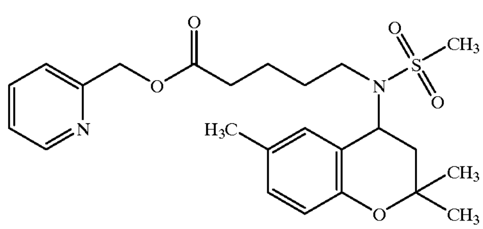 | | | | |
| 220 | 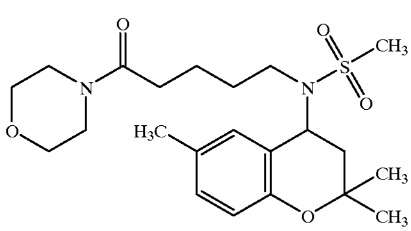 | | | | |

-continued

| Ex. | Structure | M.p. | Recryst. t | Recryst. from | IC$_{50}$ ($\mu$Mol) |
|---|---|---|---|---|---|
| 221 | 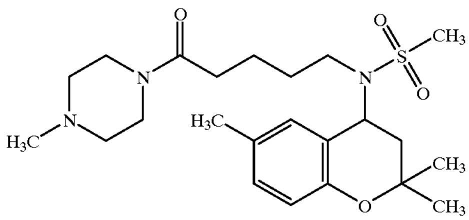 | | | | |
| 222 | 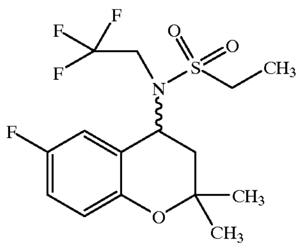 | 91 | 1 | petroleum ether | 1.03 |
| 223 | 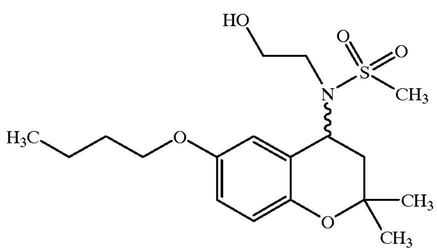 | 107 | 1 | diisopropyl ether | 0.19 |
| 224 | 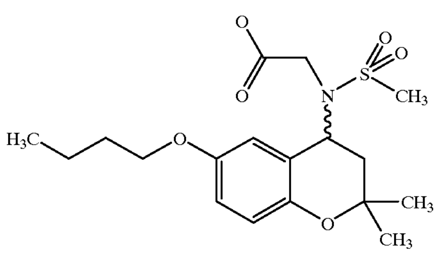 | 104 | 1 | petroleum ether/ diisopropyl ether | 18.37 |
| 225 | 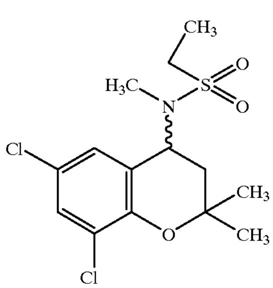 | 33 | 2 | | |

| Ex. | Structure | M.p. | t | Recryst. from | IC$_{50}$ ($\mu$Mol) |
|---|---|---|---|---|---|
| 226 | 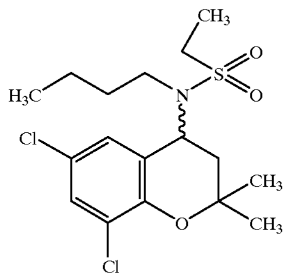 | 105 | 2 | | |
| 227 | 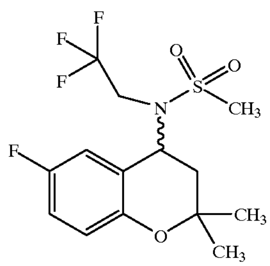 | 104 | 1 | petroleum ether | 1.23 |
| 228 | 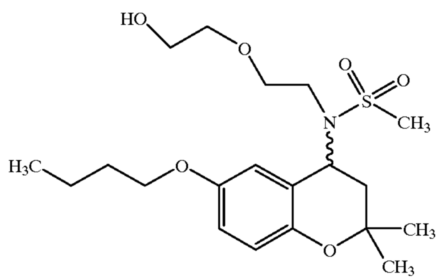 | | | | 2.0 |
| 229 | 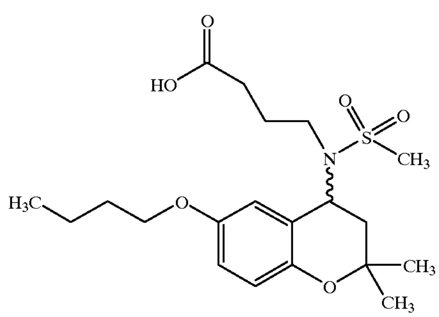 | 119 | 1 | diisopropyl ether | 5.2 |
| 230 | 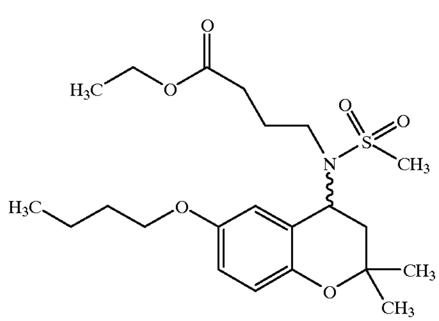 | | | | 0.045 |

-continued

| Ex. | Structure | M.p. | Recryst. t | Recryst. from | IC$_{50}$ ($\mu$Mol) |
|---|---|---|---|---|---|
| 231 | 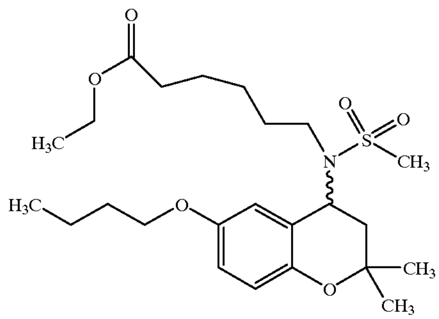 | | | | 0.038 |
| 232 | 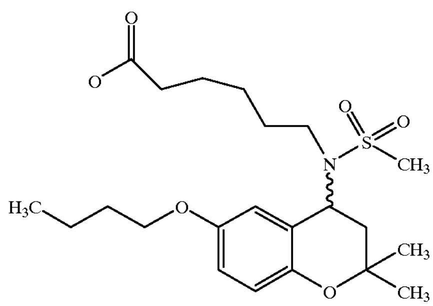 | 94 | 1 | petroleum ether | 18.5 |
| 233 | 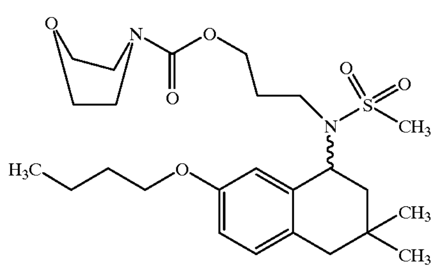 | 79 | 1 | diisopropyl ether | 0.18 |
| 234 | 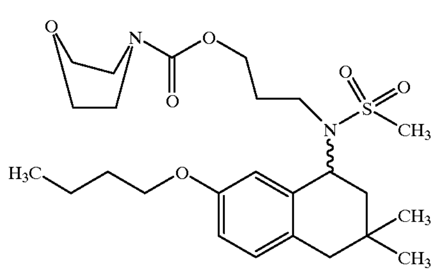 | 72 | | | 1.25 |
| 235 | 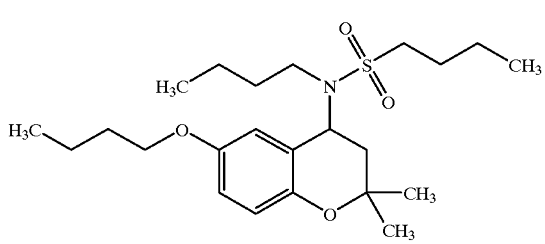 | 50 | | | 5.2 |

-continued

| Ex. | Structure | M.p. | Recryst. t | Recryst. from | IC$_{50}$ ($\mu$Mol) |
|---|---|---|---|---|---|
| 236 | 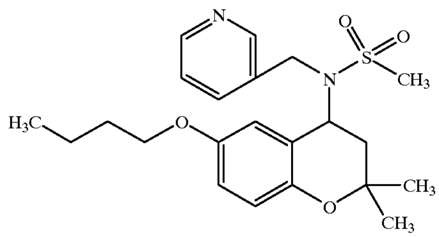 | | | | 1.1 |
| 237 | 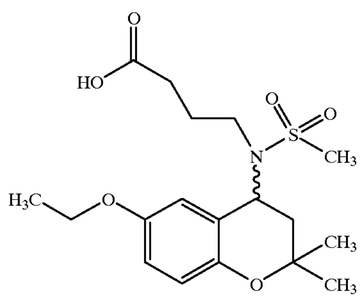 | 139 | 1 | aq. HCV/THF | 10.5 |
| 238 | 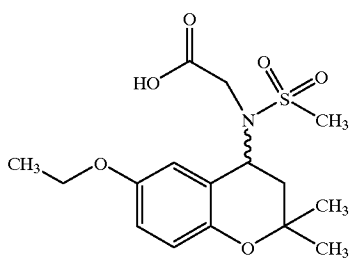 | 159 | 1 | petroleum ether | |
| 239 | 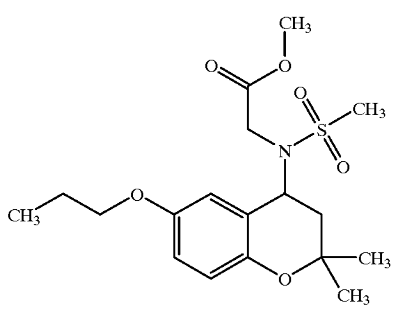 | 123 | 1 | | 0.05 |
| 240 | 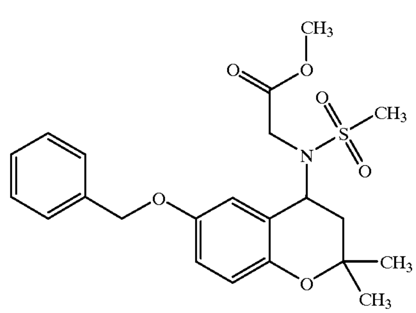 | 114.5 | 0.5 | | 0.05 |

-continued

| Ex. | Structure | M.p. | Recryst. t from | IC$_{50}$ ($\mu$Mol) |
|---|---|---|---|---|
| 241 | 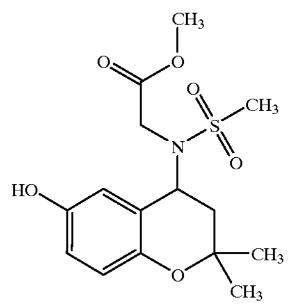 | 174 | 1 | |
| 242 | 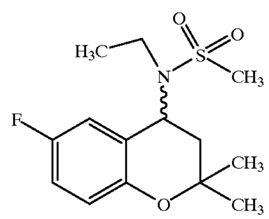 | 77 | 1 | 0.75 |
| 243 | 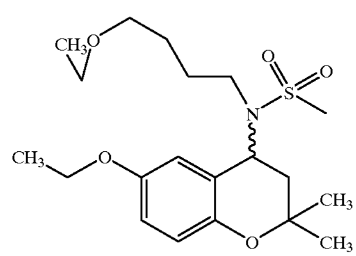 | | | 0.35 |
| 244 | 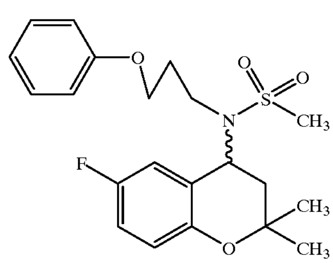 | 117 | 1 diisopropyl ether/ petroleum ether | 0.1 |
| 245 | 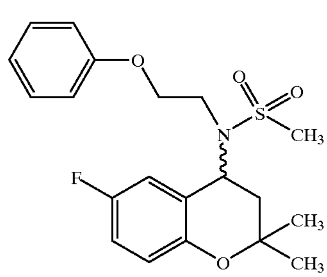 | 101 | 1 diisopropyl ether/ petroleum ether | 0.3 |

| Ex. | Structure | M.p. | Recryst. t from | IC$_{50}$ (µMol) |
|---|---|---|---|---|
| 246 | 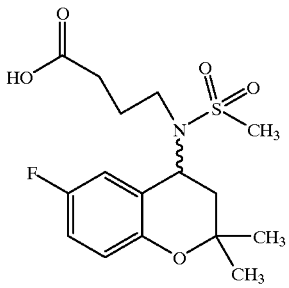 | 145.5 | 1.5 diisopropyl ether | |
| 247 | 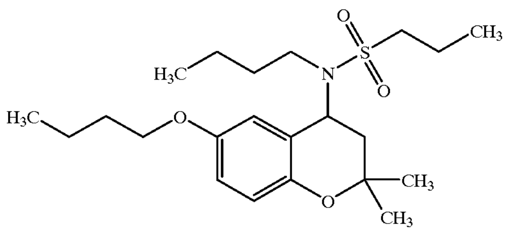 | | | 3.3 |
| 248 | 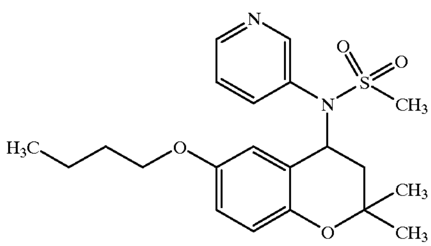 | 111 | | |
| 249 | 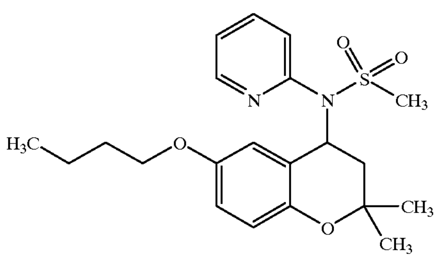 | | | 0.81 |
| 250 | 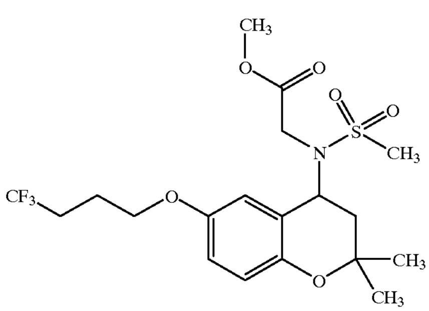 | 103 | 1 | |

Pharmacological investigations;

I$_{sX}$ channels from man, rat or guinea-pig were expressed in *Xenopus oocytes*. For this purpose, oocytes from *Xenopus laevis* were first isolated and defolliculated. The oocytes were then injected with I$_{sX}$ encoding RNA synthesized in vitro. After 2–8 days of I$_{sX}$ protein expression, I$_{sX}$ currents were measured using the two microelectrode voltage clamp technique, I$_{sX}$ channels were in this case generally activated using voltage jumps to −10 mV lasting 15 s and the bath was rinsed through with a control solution of the following composition (mM): NaCl 96, KCl 2, CaCl$_2$ 1.8 , MgCl$_2$ 1, HEPES 5 (titrated with NaOH to pH 7.5). These experiments were carried out at room temperature. The software employed for raising data and analysis was: Geneclamp amplifier (Axon instruments, Foster City, USA) and MacLab D/A converter and software (AD Instruments, Castle Hill, Australia). Chromanols were tested by adding them to the control solution at different concentrations. The effects of the chromanols were calculated as percentage inhibition of the $I_{sK}$ control flux. The data were then extrapolated using the Hill equation in order to determine the $IC_{50}$ for the respective substances. The data are given as average values with standard deviation (S.E.M.). n is the number of experiments carried out. Statistical significance was determined by means of the paired Student's t-test.

References:

Busch A E, Kopp H-G, Waldagger S, Samarzija I. S üβbrich H, Raber G, Kunzelmann K, Ruppersberg J P and Lang F (1995) Inhibition of both exogenously expressed $I_{sX}$ and endogenous K$^+$ channels in *Xenopus oocytes* by isosorbide dinitrate. J Physiol 491: 735–741

Takumi T, Ohkubo H and Nakanishi S (1989) Cloning of a membrane protein that induces a slow voltage-gated potassium current. Science 242:1042–1046 Varnum M D, Busch A E, Bond C T, Maylie J and Adelman J P (1993) The minK channel inserted the cardiac potassium current and mediates species-specific responses to protein kinase C [Proc Natl Acad Sci USA 90:11528–11532].

| Compound | Example No. | $I_{sK}$ $IC_{50}$ [µmol/l] |
|---|---|---|
| 6-Cyan-4-[N-ethylsulfonyl-N-(4,4,4, trifluorobutyl)]amino-2,2-dimethylchroman | 33 | 0.42 |
| 4-(N-Butyl-N-ethylsulfonyl)amino-5-cyan-2,2-dimethylchroman | 38 | 0.75 |
| trans-6-Cyan-4-(N-ethylsulfonyl-N-methylamino)-3-hydroxy-2,2-dimethylchroman | 293B[1] | 6.9 ± 0.4 |
| trans-6-cyano-4-(N-methylsulfonyl-N-methylamino)-3-hydroxy-2,2-dimethylchroman | 374B[1] | 19.2 ± 1.2 |
| trans-6-Cyano-4-[N-(dimethylamino)sulfonyl-N-methylamino]-3-hydroxy-2,2-dimethylchroman | 377B[1] | 14.6 ± 0.5 |
| trans-6-Cyano-4-[N-(1-butylsulfonyl)-N-methylamino]-3-hydroxy-2,2-dimethylchroman | 350B[1] | 58.8 ± 1.8 |

[1]E. Lohrmann, I. Burhoff, R. B. Nitschke, H. J. Lang, D. Mania, H. C. Englert, M. Hropot, R. Warth, W. Rohm, M. Bleich, R. Greger, Pilügers-Arch - Eur. J. Physiol (1995) 429: 517–530.

Inhibition of gastric acid secretion, antiulcer action:

Method: High pressure perfusion of the rat stomach was carried out according to the description of Berglindh and Obrink (1) and using some modifications as reported elsewhere (2). Rabbits (male and female, 2–3 kg) were killed painlessly under anesthesia by cervical dislocation and the stomach was perfused as reported in the literature (1). The mucosa of the stomach fundus was removed using a scraper and cut into small pieces by means of scissors. The mucosal fragments thus obtained were treated with 1 mg/ml of collagenase in a medium consisting of 100 mM NaCl, 5 mM KCl, 0.5 mM NaH$_2$PO$_4$, 1 mM Na$_2$HPO$_4$, 1 mM CaCl$_2$, 1.5 mM MgCl$_2$, 20 mM NaHCO$_3$, 20 mM HEPES, 2 mg/ml of glucose and 1 mg/ml of rabbit albumin for 30–45 min at 37° C., the pH of the mixtures being adjusted to 7.4 using tris buffer. The glandular tubes (gastric glands) were filtered through a nylon mesh to remove large fragments and rinsed 3 times with incubation medium. The glandular tubes were then suspended in the medium at a concentration of 2–4 mg of dry weight/ml.

As a measure of the capability of the gastric glandular tubes to form acid, the accumulation of $^{14}$C-aminopyrine ($^{14}$C-AP) was determined (3). To do this, samples of 1 ml of glandular tube suspension were incubated with $^{14}$C-AP (1 µM, 200,000 cpm) and the compound to be tested and treated for 20–30 min at 37° C. in a shaking water bath. Histamine (100 µM), dbcAMP (0.3 to 1 mM) or carbachol (100 µM) were then added, followed by a second incubation period of 30–45 min. The incubation was then concluded by centrifuging the samples for half a minute. The supernatant liquid was removed and the pellets obtained were dissolved in 1 ml of NaOH. Samples of the pellets and of the liquid supernatant were measured in a scintillation counter. The AP ratio of the intraglandular and extraglandular radioactivity was calculated according to Sack and Spenney (4). All determinations were carried out in triplicate.

Result: 6-Cyano-4-(n-ethylsulfonyl-N-methyl)amino-2,2-dimethyl-3-chromanol caused a concentration-dependent inhibition of stimulated AP accumulation with $IC_{50}$ values of 20 µM after histamine and dcbAMP stimulation, and of 5 µM after stimulation with carbachol.

References:

1. Berghlind, T., Obrink, K. J. A method for preparing isolated glands from the rabbit gastric mucosa, Acta Physiol. Scan. 96, 150–159 (1976)

2. Herling, A. W., Becht, M., Kelker, W., Ljungstrom, M., Bickel, M., Inhibition of $^{14}$C-aminopyrine accumulation in isolated rabbit gastric glands by the H$_2$-receptor antagonist HOE 760 (TZU-0460). Agents and Actions 20: 35–39 (1987)

3. Berghlind, T., Helander, H. F., Obrink, K. J., effect of secretagogues on oxygen consumption, aminopyrine accumulation and morphology in isolated gastric glands. Acta Physiol. Scand. 97 401–414 (1976)

4. Sack, J., Spenney, J. G., Aminopyrine accumulation by mammalian gastric glands: an analysis of the technique. Am. J. Physiol. 243: G 313–G 319 (1982).

What is claimed is:

1. A chroman of formula I:

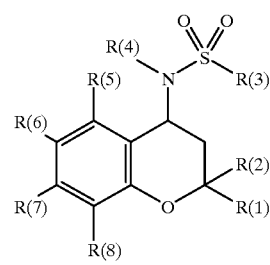

wherein:

R(1) and R(2) each independently of one another is hydrogen $C_pF_{2p+1}$, having 1, 2, 3, 4, 5 or 6 carbon atoms, or phenyl, which is unsubstituted or substituted by 1 or 2 substituents selected from F, Cl, Br, I, —CF$_3$, methyl, methoxy, sulfamoyl, methylsulfonylamino or methylsulfonyl;

p is 1, 2, or 3; or

R(1) and R(2) together are an alkylene chain having 2, 3, 4, 5, 6, 7, 8, 9, or 10 carbon atoms;

R(3) is R(9)—C$_n$H$_{2n}$[NR(11)]$_m$—;

R(9) is hydrogen or cycloalkyl having 3, 4, 5, 6, 7, or 8 carbon atoms;

n is zero, 1, 2, 3, 4, 5, 6, 7, 8, 9, or 10;

m is zero or 1;

R(11) is hydrogen or alkyl having 1, 2, 3, 4, 5, or 6 carbon atoms; or

R(11), together with R(9), is an alkylene group having 1, 2, 3, 4, 5, 6, 7, or 8 carbon atoms;
where one $CH_2$ group of the group $C_nH_{2n}$ is optionally replaced by —O—, —$SO_q$—, or —NR(10)—;
q is zero, 1, or 2;
R(10) is hydrogen, methyl, or ethyl;
R(4) is R(12)—$C_rH_{2r}$—;
R(12) is hydrogen, cycloalkyl having 3, 4, 5, 6, 7, or 8 carbon atoms, piperidyl, 1-pyrrolidinyl, N-morpholino, N-methylpiperazino, —$C_pF_{2p+1}$ pyridyl, thienyl, imidazolyl, or phenyl, which is unsubstituted or substituted by 1 or 2 substituents selected from F, Cl, Br, I, —$CF_3$m methyl, methoxy, sulfamoyl, methylsulfonyl or methylsulfonylamino;
r is 1, 2, 3, 4, 5, 6, 7, 8, 9, 10, 11, 12, 13, 14, 15, 16 ,17, 18, 19, or 20;
where once $CH_2$ group of the group $C_2H_{2r}$ can be replaced by —O—, —C=C—, —C≡C—, —CO—, —CO—O—, —$SO_q$— or —NR(10)—;
q is zero, 1 or 2;
R(10) is hydrogen, methyl, or ethyl;
R(5), R(6), R(7), and R(8) each independently of one another is hydrogen, F, Cl, Br, I, alkyl having 1, 2, 3, or 4 carbon atoms, cycloalkyl having 3, 4, 5, 6, 7, or 8 carbon atoms, —CN, —$CF_3$, —$C_2F_5$, —$C_3F_7$, —$N_3$, —$NO_2$, —CONR(13)R(14), —COOR(15), R(16)—$C_sH_{2s}$—Y—, or phenyl, which is unsubstituted or substituted by 1 or 2 substituents selected from F, Cl, Br, I, —$CF_3$, methyl, methoxy, sulfamoyl or methylsulfonyl;
R(13) and R(14) each independently of one another is hydrogen or alkyl having 1, 2 or 3 carbon atoms;
R(15) is hydrogen, methyl, ethyl, phenyl, or —$C_uH_{2u}$—NR(13)R(14);
u is 2 or 3;
R(16) is hydrogen, cycloalkyl having 3, 4, 5, 6, 7, or 8 carbon atoms, —COOR(15), thienyl, imidazolyl, pyridyl, quinolyl, isoquinolyl, piperidyl, 1-pyrrolidinyl, N-morpholino, N-methylpiperazino, —$C_tF_{2t+1}$, or phenyl, which is unsubstituted or substituted by 1 or 2 substituents selected from F, Cl, Br, I, —$CH_3$, methyl, methoxy, sulfamoyl or methylsulfonyl;
s is zero, 1, 2, 3, 4, 5 or 6;
t is 1, 2 or 3;
Y is —$SO_q$—, —CO—, —$SO_2$—NR(10)—, —O—, NR(10)—, or —CO—NR(10);
wherein R(6) is other than —$OCF_3$ or —$OC_2F_5$; or a physiologically tolerable salt thereof.

2. A chroman according to claim 1, wherein:
R(1) and R(2) each independently of one another is hydrogen, —$CF_3$, alkyl having 1, 2, or 3 carbon atoms, jointly an alkylene chain having 4 or 5 carbon atoms, or phenyl, which is unsubstituted or substituted by 1 or 2 substituents selected from F, Cl, Br, I, —$CF_3$, methyl, methoxy, sulfamoyl, or methylsulfonyl;
R(3) is R(9)—$C_nH_{2n}$[NR(11)]$_m$—;
R(9) is hydrogen;
n is zero, 1, 2, 3, 4, 5, or 6;
m is zero is 1;
R(11) is hydrogen or alkyl having 1, 2, 3, or 4 carbon atoms;
R(4) is R(12)—$C_rH_{2r}$—;
R(12) is hydrogen, cycloalkyl having 5, 6, 7, or 8 carbon atoms, —$CF_3$, pyridyl, or phenyl, which is unsubstituted or substituted by 1 or 2 substituents selected from F, Cl, —$CF_3$, sulfamoyl, or methylfulfonyl;
r is 1, 2, 3, 4, 5, 6, 7, 8, 9, or 10;
where one $CH_2$ group of the group $C_2H_{2r}$ is optionally replaced by —O—, —CO—, —CO—O—, or —$SO_q$—;
q is zero, 1 or 2;
R(5), R(6), R(7), and R(8) each independently of one another is hydrogen, F, Cl, Br, I, alkyl having 1 or 2 carbon atoms, —CN, —$CF_3$, —$NO_2$, —CONR(13)R(14), —COOR(15), R(16)—$C_sH_{2s}$—Y—, or phenyl, which is unsubstituted or substituted by a substituent selected from F, Cl, or —$CF_3$;
R(13) and R(14) each independently of one another is hydrogen or alkyl having 1, 2, or 3 carbon atoms;
R(15) is methyl, ethyl, phenyl, or —$C_uH_{2u}$—NR(13)R(14);
u is 2 or 3;
R(16) is hydrogen, cycloalkyl having 5 or 6 carbon atoms, —$C_tF_{2t+1}$, or phenyl, which is unsubstituted or substituted by a substituent selected from F, Cl, Br, —$CF_3$, methyl, methoxy, sulfamoyl, or methylsulfonyl;
t is 1, 2, or 3;
s is zero, 1, 2, 3, or 4;
Y is —$SO_q$—, —CO—, —$SO_2$—NR(10)—, —NR(10)—, or —CO—NR(10);
q is zero, 1, or 2;
R(10) is hydrogen or methyl;
wherein R(6) is other than —$OCF_3$ or —$OC_2F_5$; or a physiologically tolerable salt thereof.

3. A chroman according to claim 1, wherein:
R(1) and R(2) each independently of one another is —$CF_3$, methyl, or phenyl, which is unsubstituted or substituted by 1 or 2 substituents selected from F, Cl, Br, I, $CF_3$methyl, methoxy, sulfamoyl, or methylsulfonyl;
R(3) is alkyl having 1, 2, 3, or 4 carbon atoms, dimethylamino, or diethylamino;
R(4) is R(12)—$C_rH_{2r}$—;
R(12) is hydrogen, cycloalkyl having 5 or 6 carbon atoms, or —$CF_3$;
r is 1, 2, 3, 4, 5, 6, 7, or 8;
where one $CH_2$ group of the group $C_rH_{2r}$ is optionally replaced by —O—, —CO—, —CO—O—, or —$SO_q$—;
q is zero, 1 or 2;
R(5), R(6), R(7) and R(8) each independently of one another is hydrogen, F, Cl, Br, I, alkyl having 1 or 2 carbon atoms, —CN, —$NO_2$, —COOR(15), R(16)—$C_sH_{2s}$—Y—, or phenyl,
which is unsubstituted or substituted by a substituent selected from F or Cl;
R(15) is methyl, ethyl, phenyl, or —$C_uH_{2u}$—NR(13)R(14);
u is 2 or 3;
R(13) and R(14) each independently of one another is hydrogen or alkyl having 1, 2, or 3 carbon atoms;
R(16) is hydrogen, —$CF_3$, or phenyl,
s is zero, 1, 2, 3, or 4;
Y is —$SO_q$—, —CO—, —$SO_2$—NR(10)—, —O—, —NR(10)—, or —CO—NR(10);
q is zero, 1 or 2;
R(10) is hydrogen or methyl;
wherein r(6) is other than —$OCF_3$; or a physiologically tolerable salt thereof.

4. A chroman according to claim 1 wherein the chroman is 4-(N-ethylsulfonyl-N-methyl)amino-6-fluoro-2,2-dimethylchroman.

5. A chroman according to claim 1 wherein the chroman is 6-cyano-4-(N-ethylsulfonyl-N-methyl)amino-2,2-dimethylchroman.

6. A chroman according to claim 1 wherein the chroman is 4-(N-ethylsulfonyl-N-methyl)amino-6-methoxycarbonyl-2,2-dimethyl-chroman.

7. A chroman according to claim 1 wherein the chroman is 6-cyano-4-[N-ethylsulfonyl-N-(4,4,4-trifluorobutyl)]amino-2,2-dimethyl-chroman.

8. A chroman according to claim 1 wherein the chroman is 4-(N-butyl-N-ethylsulfonyl)amino-6-cyano-2,2-dimethylchroman.

9. A chroman according to claim 1 wherein the chroman is 4-(N-ethylsulfonyl-N-methyl)amino-2,2,6-trimethylchroman.

10. A chroman according to claim 1 wherein the chroman is 7-chloro-4-(N-ethylsulfonyl-N-methyl)amino-6-fluoro-2,2-dimethylchroman.

11. A chroman according to claim 1 wherein the chroman is 6,7-dichloro-4-(N-ethylsulfonyl-N-methyl)amino-2,2-dimethylchroman.

12. A chroman according to claim 1 wherein the chroman is 4-(N-butyl-N-ethylsulfonyl)amino-6-fluoro-2,2-dimethylchroman.

13. A chroman according to claim 1 wherein the chroman is 4-(N-ethylsulfonyl-N-methyl)amino-6-fluoro-2,2-tetramethylenechroman.

14. A chroman according to claim 1 wherein the chroman is 4-[ethylsulfonyl-N-(4,4,4-trifluorobutyl)]amino-6-fluoro-2,2-dimethyl-chroman.

15. A chroman according to claim 1 wherein the chroman is 4-(N-ethylsulfonyl-N-hexyl)amino-6-fluoro-2,2-dimethylchroman.

16. A chroman according to claim 1 wherein the chroman is 6-ethyl-4-[N-ethylsulfonyl-N-(4,4,4-trifluorobutyl)]amino-2,2-dimethyl-chroman.

17. A process for preparing a chroman according to claim 1, comprising reacting a compound of formula II:

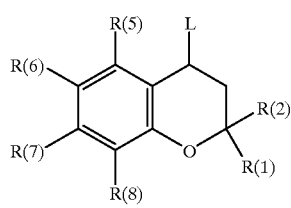

II in which R(1), R(2), R(5), R(6), R(7) and R(8) have the meanings indicated in claim 1, and L is selected from Cl, Br, I, MeSO₂—O—, a p-toluenesulfonyloxy radical, or other nucleofugic leaving group customary for an alkylation; with a sulfonamide or its salt of formula III:

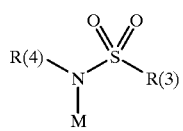

III wherein R(3) and R(4) have the meanings indicated in claim 1, and M is hydrogen or a metal atom.

18. A process for preparing a chroman according to claim 1, comprising reacting a compound of formula IV:

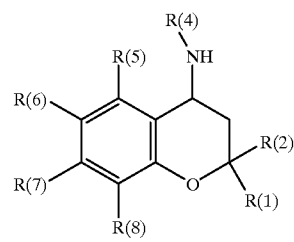

IV in which R(1), R(2), R(4), R(5), R(6), R(7), and R(8) have the meanings indicated in claim 1, with a sulfonic acid derivative of formula V:

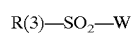

V wherein R(3) has the meaning indicated in claim 1, and W is a nucleofugic leaving group, such as fluorine, bromine, 1-imidazolyl, or chlorine.

19. A process for preparing a chroman according to claim 1, comprising reacting a compound of formula VI:

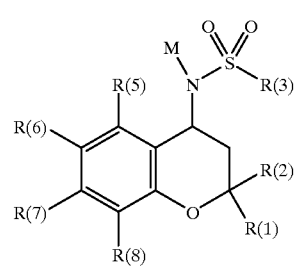

VI in which R(1), R(2), R(5), R(6), R(7), R(8) and M have the meanings indicated in claim 1, with an alkylating agent of formula VII:

VII in an alkylation reaction, in which R(4), with the exception of hydrogen, and L is selected from Cl, Br, I, MeSO₂—O—, a p-toluenesulfonyloxy radical, or other nucleofugic leaving group customary for alkylation.

20. A process for preparing a chroman according to claim 1, comprising electrophilically substituting a compound of formula I:

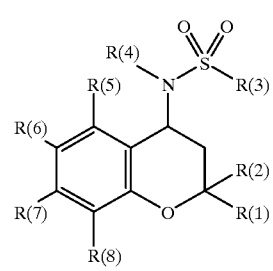

I in which R(1) to R(4) have the meanings indicated in claim 1, in at least one position R(5) to R(8), wherein said position is hydrogen.

21. A method of treating or preventing conditions wherein K⁺ channels opened by cyclic adenosine monophosphate (cAMP) are implicated, comprising administering to a patient in need thereof an amount effective to block said K⁺ channels of a chroman according to claim 1.

22. A pharmaceutical formulation, comprising an efficacious amount of a chroman according to claim 1 and a pharmaceutically tolerable excipient.

23. A method of treating or preventing a condition wherein K⁺ channels opened by cyclic adenosine monophosphate (cAMP) is implicated, comprising administering to a patient in need thereof an amount effective to block said K⁺ channels of a compound of formula Ia:

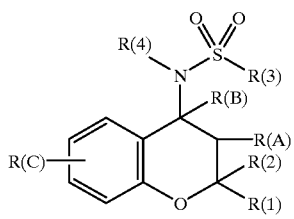

wherein:
R(A) is hydrogen, —OH, —O(CO)-alkyl having 1, 2, 3, or 4 carbon atoms or —O—SO₂-alkyl having 1, 2, 3, or 4 carbon atoms;
R(B) is hydrogen; or
R(A) and R(B) together are a bond;
R(1) and R(4) are as indicated in claim 1;
R(C) is —CN, acyl having 1, 2, 3, 4, 5, or 6 carbon atoms, F, Cl, Br, I, —NO₂, or alkyl having 1, 2, 3, 4, 5, or 6 carbon atoms.

24. The method according to claim 23 wherein the condition wherein K⁺ channels opened by cyclic adenosine monophosphate (cAMP) are implicated is gastric acid secretion.

25. The method according to claim 23 wherein the implicated condition comprises ulcers of the stomach and of the intestinal region.

26. The method according to claim 23 wherein the implicated condition comprises reflux esophagitis.

27. The method according to claim 23 wherein the implicated condition comprises all types of arrhythmias, including ventricular and supraventricular arrhythmias.

28. The method according to claim 23 wherein the implicated condition comprises reentry arrhythmias.

29. The method according to claim 23 wherein the compound is 6-cyano-4-(N-ethylsulfonyl-N-methyl)amino-2,2-dimethyl-3-chromanol.

30. A method of blocking the K⁺ channel which is opened by cyclic adenosine monophosphate comprising administering to a patient in need thereof an effective amount of at least one chroman according to claim 1.

31. A method of inhibiting gastric acid secretion comprising administering to a patient in need thereof an effective amount of at least one chroman according to claim 1.

32. A method for treating ulcers of the stomach and of the intestinal region comprising administering to a patient in need thereof an effective amount of at least one chroman according to claim 1.

33. A method according to claim 32 wherein the intestinal region comprises the duodenum.

34. A method of treating reflux esophagitis, comprising administering to a patient in need thereof an effective amount of at least one chroman according to claim 1.

35. A method of treating diarrheal illnesses, comprising administering to a patient in need thereof an effective amount of at least one chroman according to claim 1.

36. A method of treating all types of arrhythmias, including ventricular and supraventricular arrhythmias, comprising administering to a patient in need thereof an effective amount of at least one chroman according to claim 1.

37. A method of treating reentry arrhythmias and for preventing sudden heart death as a result of ventricular fibrillation, comprising administering to a patient in need thereof an effective amount of at least one chroman according to claim 1.

38. The process as claimed in claim 17, wherein the metal is selected from lithium, sodium or potassium.

* * * * *

UNITED STATES PATENT AND TRADEMARK OFFICE
CERTIFICATE OF CORRECTION

PATENT NO. : 6,191,164 B1  Page 1 of 1
DATED : February 20, 2001
INVENTOR(S) : Hans Jochen Lang et al.

It is certified that error appears in the above-identified patent and that said Letters Patent is hereby corrected as shown below:

Column 112,
Line 52, after "hydrogen", insert a comma.
Line 52, before "having", insert -- alkyl --.

Column 113,
Line 10, after "–$C_pF_{2p+1}$", insert a comma.
Line 13, after "–$CF_3$m" should read -- –$CF_3$, --.
Line 43, "–$CH_3$" should read -- –$CF_3$ --.
Line 62, "zero is 1" should read -- zero or 1 --.

Column 114,
Line 2, "methylfulfonyl" should read -- methylsulfonyl --.
Line 4, "$C_2H_{2r}$" should read -- $C_rH_{2r}$ --.
Line 25, after "–$SO_2$–NR(10)–," insert -- –O–, --.
Line 36, "$CF_3$methyl," should read -- $CF_3$, methyl, --.
Line 66, "r(6)" should read -- R(6) --.

Column 115,
Line 31, "4-[ethylsulfonyl" should read -- 4-[N-ethylsulfonyl --.

Column 117,
Line 31, "R(1) and R(4)" should read -- R(1) to R (4) --.

Signed and Sealed this

Eighteenth Day of June, 2002

*Attest:*

*Attesting Officer*

JAMES E. ROGAN
*Director of the United States Patent and Trademark Office*